United States Patent [19]
Grow

[11] Patent Number: 5,866,430
[45] Date of Patent: Feb. 2, 1999

[54] RAMAN OPTRODE PROCESSES AND DEVICES FOR DETECTION OF CHEMICALS AND MICROORGANISMS

[76] Inventor: Ann E. Grow, 5882 Highplace Dr., San Diego, Calif. 92120

[21] Appl. No.: 864,015

[22] Filed: May 27, 1997

Related U.S. Application Data

[60] Provisional application No. 60/019,742 Jun. 13, 1996.
[51] Int. Cl.[6] ........................... G01N 21/65; G01N 33/02
[52] U.S. Cl. .................................. 436/172; 436/20
[58] Field of Search ................................ 436/172, 20

[56] References Cited

U.S. PATENT DOCUMENTS

| | | | |
|---|---|---|---|
| 4,411,989 | 10/1983 | Grow | 435/20 |
| 4,674,878 | 6/1987 | Vo-Dinh | 356/301 |
| 5,266,498 | 11/1993 | Tarcha et al. | 436/525 |

OTHER PUBLICATIONS

Howarth (1973) Theory of Spectroscopy An Elementary Introduction, Halsted Press, New York, pp. 143–161.

*Primary Examiner*—John P. Weber
*Attorney, Agent, or Firm*—Beehler & Pavitt

[57] ABSTRACT

A methodology and devices for detecting or monitoring or identifying chemical or microbial analytes are described. The methodology comprises four basic steps: (1) The gas or liquid medium to be monitored or analyzed is brought into contact with a bioconcentrator which is used to bind with or collect and concentrate one or more analytes. (2) The bioconcentrator-analyte complex is then exposed to radiation of one or more predetermined wavelengths to produce Raman scattering spectral bands. (3) At least a portion of the Raman spectral bands are collected and processed by a Raman spectrometer to convert the same into an electrical signal. And (4) the electrical signal is processed to detect and identify, qualitatively and/or quantitatively, the analyte(s). The methodology of this invention may also comprise Raman reactive capacity analysis of the bioconcentrator itself, simultaneously with or independently from the detection of the analyte, to determine the potential ability of the bioconcentrator to complex with analytes; the results of this latter analysis may be used to affect or alter or modify the methodology involved in detection and analysis of the analytes. Also the invention is accomplished by a Raman Optrode comprising: a bioconcentrator capable of binding with the analyte(s); a mechanism or procedure or device for bringing the gas or liquid sample into contact with the bioconcentrator; a light source suitable for generating Raman scattering; a Raman spectrometer capable of collecting and processing the Raman scattering spectral information and translating it into an electrical signal; and electronic hardware and software for analyzing the electrical signal and translating the signal into information on the presence, identity and/or quantity of the bound analytes. Various forms of bioconcentrators are described, as well as a variety of analytes which may be detected, monitored, or identified by this invention, and a variety of devices which can be fabricated based on this invention.

24 Claims, 8 Drawing Sheets

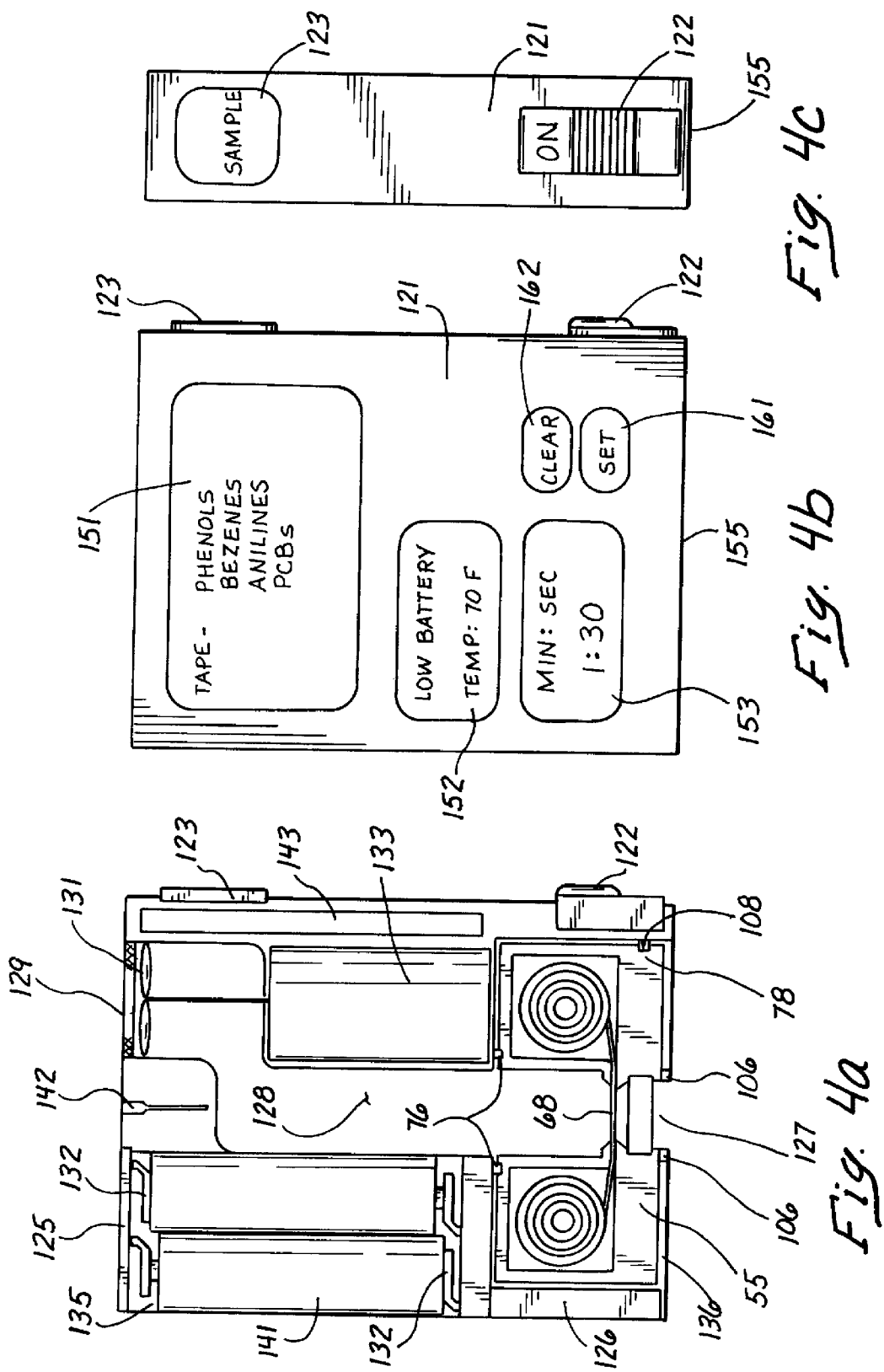

Fig. 6a
Fig. 6b
Fig. 6c
Fig. 6d

RAMAN OPTRODE PROCESSES AND DEVICES FOR DETECTION OF CHEMICALS AND MICROORGANISMS

RELATED APPLICATIONS

This application is a replacement of provisional application 60/019,742, filed on Jun. 13, 1996.

BACKGROUND OF THE INVENTION

This invention relates to a process and apparatus for the analysis of various materials and more particularly to a process and device for the detection and identification, qualitatively and/or quantitatively, of analytes such as environmental pollutants, drugs, explosives, toxins, pathogens, biological sample constituents, and chemical and biological warfare agents. The analyte is isolated, collected, and concentrated by a bioconcentrator and is then analyzed using Raman spectroscopy technology.

DESCRIPTION OF THE PRIOR ART

Detection and identification of analytes in environmental and biological matrices has traditionally required the use of wet chemistry analytical procedures. These procedures often involve elaborate, time consuming, and labor intensive sample collection, preparation, analysis, and data interpretation steps that require a highly trained technician and sophisticated, expensive instrumentation.

In some instances, it has been possible to adapt laboratory analytical instrumentation for use as dedicated monitoring equipment designed to perform sample collection and analysis automatically, reducing the amount of labor and the time required to obtain results. For example, infrared (IR) spectroscopy can sometimes be used to monitor stack gas emissions for pollutants. When light is propagated through a uniform material, part of the light is absorbed and part transmitted by the material; IR spectroscopic techniques measure light absorption/transmission in the IR window due to molecular vibrations. As the molecular structure changes, so does the IR spectrum, i.e., the IR spectrum is a "fingerprint" of the material, unique to its chemical composition; if the chemical composition changes, then so does the fingerprint IR spectrum. Therefore, if the composition of the stack gas changes, the change can be detected by monitoring some portion of the IR spectrum. However, the more complex or variable the content of a material, the more difficult it is to accurately determine the causes for the changes in the fingerprint, due to the spectra of many different chemicals overlapping with each other. Hence, even fingerprint instruments such as IR spectrometers cannot be used for many detection applications, especially those requiring the detection of trace levels of analytes in complex samples. Further, IR spectroscopy is usually incompatible with the direct detection of analytes dissolved or suspended in aqueous media.

While part of the light propagated through a uniform material is absorbed and transmitted by the material, part is also scattered by a variety of processes. Like IR, one of the scattering processes, i.e., Raman scattering, is also due to molecular vibrations. However, unlike IR, which describes vibrational frequencies together with information concerning the absorption intensity, Raman yields information about the scattering cross section. IR and Raman rely upon fundamentally different physical processes. IR relies upon a change in the dipole moment of the absorbing species during a vibrational cycle. Since asymmetric species have larger dipole moments than more symmetric species, strong IR spectral features arise from polarized groups and antisymmetric vibrations of symmetric groups.

Raman scattering intensity depends upon the degree of modulation of the polarizability of the scattering species during a vibrational cycle, i.e., Raman frequencies arise from changes in the electronic polarizability associated with nuclear vibrational displacements. Thus symmetric vibrational modes of symmetric species and groups which contain polarizable atoms such as sulfur tend to scatter strongly. The three-dimensional structure and the intramolecular-intermolecular interactions of a molecule determine the frequencies and forms of its normal modes of vibration. Therefore, by analyzing the frequencies, intensities, and polarization states observed in the Raman effect, molecular structure can be determined. Raman spectroscopy, based on such analyses, is a less well-known analytical technique that is as powerful as IR in generating unique fingerprint information, but due to the significant differences between the two, not only produces significantly different information, but also has the advantages of being compatible with aqueous samples as well as nonaqueous liquids, and of being capable of analyzing solids or surfaces without any sample preparation. It is known, for example, that by analyzing the frequencies, intensities, and polarization states observed in the Raman effect, the molecular structure of chemicals even as complex as biological macromolecules can be determined. Protein conformational changes, charge effects, bond distortions, and chemical rearrangement can be studied in the region from 200 to 2000 $cm^{-1}$, and some can be studied in the range from 100 to 4000 $cm^{-1}$. Similarly, Raman has been used to study phosphodiester backbone geometries of DNA and RNA; and is now even being used to elucidate the chemistry and conformation of biological macromolecules and complexes in situ in membranes, individual living cells, and tissues. Because of its compatibility with aqueous solutions, Raman spectroscopy is one of the few techniques that can be used to study the chemistry of biologicals in their native (i.e., solubilized) form.

A Raman spectrum is generated by illuminating a sample with a single, specific wavelength of light. Raman scattering is best studied when produced by a narrow intense beam of monochromatic radiation and observed at right angles to the beam, so that the intensity of the exciting beam does not overwhelm the much less intense Raman scattered radiation. Hence, lasers are used almost exclusively to excite Raman scattering. The Raman spectrum, i.e., the scattered wavelengths and their relative intensities, are substance-specific, characteristic of to the sample's molecular structure. Because the Raman spectral fingerprint is unique to a given compound, Raman may be used to identify "unknown" samples by comparison of the wavelength-shifted scattered light from the sample with Raman spectral signatures from "known" substances. Recently, Raman scattering spectroscopy has been investigated for use in water monitoring systems. Since only a small percentage of the propagating light is Raman scattered, normal Raman scattering (NRS) spectroscopy produces a relatively weak signal, and, hence, any analytical procedure or monitor based on NRS has relatively poor sensitivity. However, two different phenomena may be exploited to gain additional sensitivity during Raman analysis, i.e., resonance Raman scattering (RRS) and surface enhanced Raman scattering (SERS).

NRS is produced when the frequency of the exciting light is far away from an electronic absorption band of the analyte molecule. In RRS, however, the excitation frequency approaches or coincides with an electronic absorption frequency of the molecule. (The portion of the molecule that resonates is often referred to as a "chromophore", since most laser lights excite resonance in the visible portion of the spectrum.) Under such resonance conditions, the lines due to the vibrational modes of the chromophore or adjacent groups of atoms are selectively and significantly enhanced, usually to the point that the enhanced lines are the only lines observed in the Raman spectrum; it is known that RRS techniques enhance the Raman signal by factors of $10^3$ to $10^6$. RRS has one additional advantage over NRS, i.e., because only the lines from the chromophore are seen, the RRS spectrum is much more simple and has far fewer lines than the NRS spectrum. For example, biological materials exhibit exceptional chemical complexity, and their Raman spectra are correspondingly complex. RRS has proved useful for simplifying these complex spectra and thereby probing the active sites and chemical reactions of biological materials, and assigning Raman lines to functional groups and bonds within the biological macromolecule or complex.

In the late 1970s, researchers discovered that a monolayer of a compound adsorbed on a roughened, thin layer of metal exhibits a Raman signal which is enhanced as much as $10^9$ times the NRS signal. This phenomenon has been called "surface enhanced Raman scattering (SERS)". Most studies conducted on SERS in the 1980s were targeted at examining the chemical and physical bases for the surface enhancement phenomenon. For example, it is now known that the surface enhancement effect is limited to molecules or moieties in direct contact with, or in extremely close proximity to, the roughened metal surface. This can be an advantage, in that signals from the surrounding bulk medium will be too weak to be detected, making it easier to analyze the adsorbed molecules. However, portions of extremely large molecules such as many proteins will be too far from the metal surface for any significant enhancement of their Raman signals to occur. For example, it has been shown that the distance from the electrode over which surface and resonance enhancements extend in SERRS of adsorbed macromolecules is approximately 16 nm; signals from amino acids bound directly to the surface of the electrode or within five or six residues from the surface are more strongly enhanced than the signals from other residues within a protein molecule. Therefore, by using a roughened metal electrode and altering the potential of the electrode, it is possible to alter the orientation of macromolecules in such a way as to maximize the enhancement of signals belonging to selected moieties within the macromolecule. Hence, it is possible to use electrode potential as well as resonance techniques to selectively study groups or residues within a large, complex macromolecule such as a biological.

Further, it is now known that RRS, when used in conjunction with surface enhancement [surface enhanced resonance Raman scattering (SERRS)], can enhance sensitivities as much as $10^{11}$ to $10^{13}$ times the NRS signal, i.e., full spectra can be generated with fewer than $10^7$ molecules. SERRS can therefore be one of the most sensitive technologies available for possible use in detection processes and devices; hence, researchers have started to investigate the practical application of SERS and SERRS, i.e., by depositing a sample of a material to be analyzed directly on a roughened metal surface in order to generate a stronger Raman spectral signal for analysis of trace components. For example, U.S. Pat. No. 4,674,878 "Practical Substrate and Apparatus for Static and Continuous Monitoring by Surface Enhanced Raman Spectroscopy", T. Vo-Dinh, describes an apparatus and methodology which utilizes SERS for trace analysis of organic compounds.

However, Raman spectroscopy, even with such a strongly enhanced SERS or SERRS signal, suffers from the same limitations as IR spectroscopy, i.e., it must be used with samples or materials which are relatively pure; which are relatively constant in composition, varying primarily in the presence/absence of the analyte; which have a relatively high concentration of the analyte; or which have been processed to isolate the analyte from other sample constituents, e.g., through the use of chromatography techniques. Otherwise, the fingerprint signal from the analyte will be obscured by the fingerprints of all of the more numerous or concentrated species in the sample, thereby yielding poor sensitivity and specificity, and numerous false responses. Considerable effort and redesign are required to adapt such processes or instrumentation for use in new environments or with new media or sample compositions. For example, when SERS is used for trace analysis, the signals from all compounds in any sample applied to the metal surface are enhanced; hence, while smaller sample volumes may be used, the complex, overlapping signals generated by this approach make it impossible to detect or identify trace levels of analytes. Because RRS selectively enhances only the signals from chromophoric molecules, attempts have been made to gain specificity through the judicious selection of the laser excitation wavelength. However, pre-resonance effects can enhance the signals of more concentrated species in the sample to the point that even the strongly enhanced RRS signal from the trace analyte, present in much lower concentrations, will still be overwhelmed by the combined weaker signals from the more numerous species. Most sample matrices are of sufficient complexity that RRS alone can rarely, if ever, achieve sufficient specificity for monitoring trace analytes. Very recently, therefore, studies have been initiated to identify coatings such as polymers or crown ethers that could be used to capture analytes specifically, pulling the analyte out of solution and bringing it, and only it, onto contact with the SERS-active coating, leaving the other sample constituents in the bulk medium where they are too far away from the surface for their signals to be enhanced by the SERS effect. However, the coatings identified to date have failed to offer the specificity needed for most analysis, detection, or monitoring applications.

The most widely used and/or studied procedures for the detection and identification of microorganisms fall under one of two broad categories. (1) Analyses of living microbes involve cell culturing in various nutrient and/or dye media, pre-enrichment steps, and other wet chemistry techniques, often coupled with visual microscopic examination. Alternatively, (2) the sample may be treated to disrupt any cellular material, the freed nucleic acid content digested by a mixture of enzymes, the nucleic acid fragments processed by chromatographic techniques (e.g., Western or Southern blots, etc.) and then reacted with probes that are tagged, e.g., with radioisotope, fluorescent, or enzyme labels, and the labels then detected. Such analyses require up to several days to complete.

Some researchers have suggested that vibrational spectroscopies, such as infrared or Raman, can be used to identify microorganisms. Vibrational spectra of bacteria, for example, are fingerprint-like patterns which are highly reproducible and typical for different bacteria. Since intact cells are involved, the spectra are the integrated 'images' of the total chemical composition (proteins, membranes, cell wall, nucleic acids, etc.) of the cell. Owing to the multitude of cellular constituents, superimposed spectral bands are observed throughout the entire spectral range, i.e., the spectra show broad and complex contours rather than distinct peaks. Much of the information about the individual cellular constituents is 'hidden' beneath the shape of the spectrum; although some bands can be assigned to distinct functional groups or chemical substructures, the vast majority cannot. Therefore, conventional spectrum identification algorithms cannot be used to classify bacterial spectra. Other types of algorithms, however, such as pattern recognition techniques have been used. For example, a German company has introduced a Fourier-transform IR (FTIR) prototype that exploits pattern recognition algorithms to identify more than 300 diverse gram-positive and gram-negative bacteria, differentiating down to the species, and usually to the strain and/or serogroup/serotype, level, on the basis of their vibrational spectra alone. Nevertheless, IR cannot be used as the sole mechanism for detection and identification of microorganisms in complex samples (e.g., for the identification of pathogens in environmental samples or clinical specimens), for several reasons. First, the algorithms required to sort through a reference library composed of a single reference spectrum each from hundreds of thousands of different bacterial species, plus all the thousands upon thousands of species of algae, yeasts, and molds, spores, viruses, and pollens—not to mention myriad other particulate contaminants—to ensure specific identification of a given unknown are extremely cumbersome; and the effort and cost required to develop such a data base is prohibitive. Furthermore, the problem is even more complex than that. Many species are comprised of multiple strains, some pathogenic and some not, but all exhibiting different spectra. Therefore, many reference spectra are required for most microbial species. In addition, while the spectra taken from different aliquots of identical bacterial suspensions are essentially identical, variability in the spectra increase when a given strain is grown under different conditions; and so for each bacterial strain, multiple reference spectra are needed. Accordingly, it has taken many years to develop the German FTIR; and its use is predicated on culturing isolated bacteria Linder a very specific set of conditions to ensure that the cellular constituents will match those of the microbes used to develop the reference spectra. Second, a pathogen detector will not have the luxury of analyzing pure cultures; it must be capable of detecting the pathogen's signature in a mixture of all signals of all possible sample constituents in any possible concentration in any possible combination. This requirement substantially complicates the algorithms even further. In fact, pattern recognition algorithms are very poorly suited for analyzing mixtures, since they are not quantitative. The German system is designed to analyze only pure colonies cultured from individual cells. Third, to achieve reasonably rapid response times, the detector must provide sufficient sensitivity that culturing is not required. Even with microprobe technology, the German FTIR requires microcolonies 40–80 $\mu$m in diameter (a 40 $\mu$m spot corresponds to ~$10^4$ bacterial cells). Although the biomass requirements are minimal, they still translate into an incubation period of 6–8 hours for aerobes, and even longer for slow-growing anaerobes. Since viruses are not readily cultured, they cannot be detected by the FTIR approach at all. And, fourth, IR analysis is not compatible with water; even the minimal amount of water inside a bacterial cell is sufficient to mask key IR windows needed for specific identification. Hence, the German protocol includes a drying step.

It has been suggested that, since Raman provides the same high degree of rich spectral information as IR, Raman could serve as the sole basis for bacterial identification and/or as a supplementary method coupled with IR analysis. The use of Raman would overcome problems with interference from water. Nevertheless, Raman, like IR, cannot be used for the detection and identification of microbes in complex samples for the self-same reasons that IR cannot be used. Like IR, studies conducted to date on Raman identification of microorganisms have utilized purified cultures of microorganisms grown under a strictly controlled set of laboratory conditions. It has also been suggested that resonance Raman techniques can be used to selectively probe different taxonomic markers within the microorganisms, to provide additional detail on the identity of the organism and gain additional specificity. For example, at 242, 251, and 257 nm excitation, signals from nucleosides, nucleic acids, quinones, and dipicolinate are selectively enhanced. At 231 and 222 nm excitation, spectra reflect protein aromatic amino acid and proline peaks almost exclusively. However, these studies have highlighted another problem inherent in the use of Raman for identification of microorganisms. Some bacterial cell constituents vary widely in relative content during different points in the growth cycle or due to different environmental conditions. For example, since RNA content is a function of growth rate, spectra excited early in a culture's growth cycle show much more intense nucleic acid peaks than those excited from older cultures. Similarly, sporulation, brought on by certain culture conditions, can markedly affect the bacterial cell's RRS spectrum at select wavelengths; signals from the dipicolinate in endospore cores dominate the spectra of sporulating *B. subtilis* at 242, 251, and 257 nm excitation, for example. The more variation found in the spectra of a given species, the more model spectra that must be included in the reference library, and the more complicated the pattern recognition algorithms. Furthermore, many laser wavelengths that might be of interest for probing useful taxonomic markers cannot be used with this approach, since the wavelengths induce intense fluorescence, which overwhelms the much weaker Raman signals. No solutions to these problems have been proposed. Identification of microorganisms by either Raman or IR still requires the culturing of pure colonies followed by labor-intensive analysis of very cumbersome databases, the entire process requiring several days to accomplish.

Many researchers believe that biosensors might be capable of achieving the specificity needed for direct detection of trace components in complex matrices. Biosensors differ from all other devices and processes in that they utilize a biological component such as enzymes, antibodies, or receptors. In a biosensor, the biological component binds with the analyte and, in so doing, produces a "biological signal". The biological component is coupled with a transducer which is capable of detecting this "biological signal" and translating it into an electrical signal, which can then be used to generate outputs such as alarms and the like. In theory, the exceptional specificity which biological components demonstrate in binding an analyte can produce a biosensor device with the same degree of specificity.

Unfortunately, however, prior art biosensors utilize a "nonspecific" transducer that monitors an "indirect signal". In other words, the transducer does not detect a signal directly associated with or caused by the analyte itself, but, rather, a signal caused by biological activity, e.g., enzyme catalysis of a substrate, the opening or closing of a receptor channel to permit or prevent passage of ions, or the competition between the analyte and a tagged or labeled molecule for binding at an antibody's active site. In each case, the nonspecific transducer monitors some characteristic of an added reagent or secondary compound or material; it does not measure or detect any aspect or characteristic of or unique to the analyte itself. In fact, the transducers detect signals that are so nonspecific, many sample constituents can generate the same signal, or may alter the level of the signal produced by the biological activity. The nonspecific transducer cannot tell the difference, and will give a false response due to these nonspecific interferences.

Take, for example, enzyme-based biosensors which are designed to detect analytes that inhibit enzyme activity. In these devices, the transducer measures a change in signal due to an enzyme substrate being consumed, an enzyme reaction product being formed, or even a change in some additional reagent caused by the consumption of substrate or the formation of a reaction product, such as a change in the color of a dye due to a change in pH due to substrate consumption or reaction product formation. If an inhibitor, i.e., the analyte, is present, it occupies the enzyme's active site, preventing the enzyme from catalyzing its substrate, which in turn prevents the change in pH and therefore prevents the change in color. The nonspecific transducer "sees" that the color did not change, and "assumes" this means that the analyte is present. However, the analyte itself does not cause the change in color, nor does the analyte bound to the enzyme change the color. At the same time, other sample constituents totally unrelated to the analyte can change the pH, thereby changing the color; can buffer the solution, thereby preventing a change in pH and subsequent change in color; can hydrolyze the substrate or the reaction product, causing or preventing a change in color; or can even be colored themselves. The transducer cannot tell the difference, as it only measures the color.

Receptor-based biosensors are similarly susceptible to nonspecific interferences. In these devices, the analyte might, for example, bind to a channel receptor causing its channel to open or close, thereby affecting the flow of ions through the channel. Biosensors based on receptors detect changes in the ion flow, not the analyte. The transducer measures, for example, capacitance. A pinhole in the membrane around the receptor can generate exactly the same signal as an opened receptor channel, causing the nonspecific transducer to respond as if the analyte had bound to the receptor.

Similarly, antibody-based biosensors (immunosensors) are also susceptible to nonspecific interferences. Immunosensors usually establish competition between the analyte and a labeled analog for the binding site on the antibody, with the transducer detecting the label, not the analyte. The label may be, for example, a fluorophore, and the transducer a fluorescence detector. If analyte is present, a smaller amount of the labeled analog can bind to the antibody, and the transducer will "see" a lower level of fluorescence. The transducer, then, equates low fluorescence with high analyte concentrations. However, many compounds are naturally fluorescent; when these adsorb onto any surface in the vicinity of the antibody, the transducer will detect fluorescence and interpret this as absence of analyte when analyte may, in fact, be present. Alternatively, many compounds quench fluorescence; if these bind or adsorb near the antibody, they will prevent the transducer from detecting the fluorescent tag, "fooling" the transducer into responding as if analyte were present when it is not.

Similar nonspecific interferences plague all biosensors based on nonspecific transducers, affecting the sensitivity, specificity, and false alarm rate of the biosensor device.

In addition to nonspecific interferences, specific interferences, i.e., sample constituents that are chemically similar to the analyte, may also cause problems for nonspecific transduction biosensors. Most biological components bind or interact with a number of structurally similar compounds, not just one analyte. For example, the enzyme cholinesterase, widely studied and used for the detection of nerve agents, may be inhibited by some three hundred different organophosphorus and carbamate compounds, not just the three nerve agents of interest. Any inhibitor will affect the enzyme's activity, thereby affecting the signal detected by the transducer. No matter which inhibitor is present, the signal the transducer detects is the same; only the intensity of the signal or the rate at which the intensity of the signal changes may differ. Therefore, while a nonspecific transducer can determine that one or more inhibitors are present, it cannot determine which inhibitor, or even how many different inhibitors, may be in the sample. Similarly, several different toxins may affect the opening and closing of a receptor channel; a capacitance transducer can determine that the flow has been affected, but cannot determine which toxin or mixture of toxins was responsible. Likewise, antibodies may "cross react" with more than one antigen or hapten; an immunofluorescence biosensor cannot tell which antigen or hapten is present, or even whether multiple cross-reactive species are in the sample.

Because conventional biosensor technologies cannot specifically identify the compound, it is impossible to design a biosensor that can detect and identify more than one analyte without the use of a different transducer as well as a different biological component for each analyte; and it is impossible to design a biosensor that can quantify more than one analyte without the use of a different transducer and biological for each. Hence, as the number of analytes that must be identified and/or quantified in a given sample or material increases, so does the size and complexity of the biosensor device.

Most biosensor processes and devices require that the analyte be in aqueous solution when the biological component is exposed to the analyte; and the biological component is continuously in solution or solvated. Therefore, if the biosensor is to be used to detect airborne vapors or aerosols, the sample air must first be scrubbed into an aqueous collection fluid, and this fluid then introduced to the biological component. Liquid scrubbing adds to the complexity and cost of any automated system, and requires that the system be used near an adequate supply of water. In addition, the shelf life or operating life of the biosensor device may be limited, because the biological component is often less stable when solvated than when dry.

Another major drawback to conventional biosensor technologies is due to the relative fragility of the biological component. Many biological components, especially proteins such as enzymes and antibodies and complexes such as receptors, are readily denatured (i.e., degraded or inactivated) by a variety of mechanisms, including heat, changes in pH, mechanical perturbation, or the presence of non-aqueous solvents, surfactants, or proteases. Many biosensors rely on simple adsorption as the means to immobilize the biological component; an adsorbed biological component can leach off a surface when the surface is submerged in water for any period of time. With any of the biosensor technologies identified, studied, or patented to date, it is impossible to determine whether biosensor response has been affected by any of these mechanisms; that is, it is impossible to tell whether the biological component has been leached off, has been thermally or chemically or biologically denatured, or has had its binding kinetics altered by a localized change in pH or the presence or absence of co-factors, etc. Undetected loss of biological activity leads to false responses.

In addition, when conventional biosensors are produced in quantity, it is usually difficult, if not impossible, to determine whether the immobilization of the biological component has been completed successfully (i.e., whether the correct amount of the biological has been immobilized, whether the immobilized preparation is fully or only partially reactive, and/or whether the biological is in the correct orientation) without conducting destructive tests. Similarly, the reactivity of biological components which have been stored for any period of time cannot be evaluated or determined without conducting destructive tests. Therefore, the only way to evaluate lots of manufactured or stored biosensor products is to conduct random sampling on each batch of immobilized biological that is produced or stored, and to conduct destructive tests on this limited number of immobilized biological items.

In fact, when biologicals are processed in any way, e.g., synthesized, extracted, purified, lyophilized, crystallized, and/or immobilized, part or all of the biological activity may be lost or destroyed. Hence, it is necessary to measure the biological activity of the resulting preparation, sometimes at each step in a multi-step process. Some of the conventional biological activity assays involve spectroscopic techniques, such as immunoassays in which the binding of a fluorescent tag is monitored, or enzyme assays in which the formation of a colored reaction product is measured by UV-visible absorbance. Other biological activity assays involve, for example, radioactive tags. Almost all of the conventional approaches for measuring biological activity are destructive, i.e., an aliquot of each lot of the preparation is subjected to a test that either consumes or contaminates the biological in the aliquot. For example, to determine the biological activity of an immobilized enzyme preparation, a substrate is added to an aliquot of the immobilized enzyme, and the rate at which the substrate is transformed into a reaction product is determined; to determine the binding capacity of an antibody preparation, a tagged or labeled antigen is added to an aliquot of the antibody, and the amount of label which binds to the antibody is measured. Many other far more laborious techniques are also used to assess the status of a biological at various stages during the manufacture of biological products, including amino acid sequencing, chromatography, SDS-polyacrylamide gel electrophoresis, etc. All of these procedures are time-consuming and require highly trained technicians.

Antibodies are becoming increasingly popular for use in biosensors due to their high specificity and affinity, the ability to raise an antibody against most analytes of interest, and the ability to produce monoclonal antibodies (MoAbs) with uniform physical and chemical characteristics in bulk relatively easily and inexpensively. However, the high affinity of an antibody for the analyte is a major disadvantage as well as an advantage. Most immunosensors utilize a competitive binding scheme, wherein the analyte (e.g., cocaine) competes with a tagged analog (e.g., fluorescently-labeled cocaine) for the antibody binding sites. Once either ligand becomes bound to the active sites of the antibody, the antibody cannot be re-used. For each and every sample analyzed, both the antibody and the tagged analog are used up and must be discarded and replaced.

Continual replacement of antibodies and reagents is not only expensive, but also complicates operation of the biosensor as well as the supply logistics. Therefore, considerable effort is being expended on finding effective, practical ways in which to remove the bound analyte and/or labeled analog, so that the antibodies can be re-used. The approaches currently under investigation can be divided into two broad categories, one based on antibody regeneration and the other on antibody binding reversibility.

It has been known for quite some time that antibodies can be regenerated by dissociating the immune complex and rinsing the ligand away with a chaotropic reagent. A chaotropic reagent induces a significant conformational change in the antibody, the ligand, or both, by causing drastic changes in the antibody's local environment. Since optimal antibody activity generally occurs in the pH 6–8 range, chaotropic reagents which alter the pH or ionic strength of the medium will "unzip" the antibody's variable Fab regions. Effective chaotropic reagents include guanidine hydrochloride, potassium thiocyanate, HCl, ethylene glycol, sodium dodecyl sulfate/urea, and propionic acid. After the ligand is released and has been washed away, the antibody is returned to its original conformation by renaturing at neutral pH. More recent studies have focused on the possible use of temperature perturbation to regenerate the antibody; or on reducing the contribution of the hydrophobic effect to ligand binding by decreasing the polarity of the bulk solvent. Both of these latter approaches also cause significant conformational changes in the antibody; and after they have been used, the antibody must be renatured by reversing the treatment, i.e., cooling or increasing the solvent polarity. Unfortunately, a significant amount of the antibody's binding capacity may be lost with each dissociation/renaturing cycle, no matter which approach is used. Usually, enough of the capacity is destroyed that the antibody preparation must be discarded and replaced every 6–10 cycles. Furthermore, the loss in capacity tends to vary unpredictably from cycle to cycle. Since prior art biosensors are unable to determine how much effect each cycle has had on the antibody capacity, regeneration processes cannot be used for any applications requiring accuracy or precision in the quantification of the analytes.

An alternative to regeneration is based on the reversibility of antibody binding. It is known that when the binding sites of immobilized antibodies are first pre-saturated with labeled ligand, and then a sample containing the analyte is subsequently introduced, the labeled analog is "displaced" by the analyte. In one displacement approach, called "bioaffinity", the pre-saturated antibody is enclosed within a semi-permeable membrane, i.e., a membrane that is permeable to the low molecular weight analyte molecules, but not to the higher molecular weight labeled analogs. When a sample containing unlabeled analyte is introduced, the analyte diffuses through the membrane and displaces the labeled analog from the antibody binding sites. The displaced label is retained in the vicinity of the antibody by the membrane; so if the concentration of the analyte subsequently goes down, the labeled analog competes for the antibody binding sites more effectively, and as the bound analyte is gradually displaced, it diffuses through the membrane, thereby lowering the concentration even further until all analyte is gone and all analog is bound. The transducer may monitor a signal from either the label which remains bound or the label which is displaced. The bioaffinity approach offers several attractive features. For example, neither the antibody nor the labeled ligand is used up during analysis, thereby greatly reducing consumables, simplifying calibration requirements, and making it possible to design a "real-time" monitor, if desired. However, the time required for the analyte to diffuse through the membrane increases both the response time and the recovery time. In addition, because of the need for a semi-permeable membrane, bioaffinity devices are suitable only for detection of relatively low molecular weight analytes. Finally, bioaffinity sensors are susceptible to the same host of nonspecific and specific interferences as any other immunosensor approach.

More recently, a new reversible antibody technology has been invented, in which the labeled analog is attached to the antibody via a flexible chemical link. In the absence of analyte, the analog moiety occupies the antibody's active site. When a sample containing analyte is introduced, the analyte displaces the analog, much as it does in bioaffinity sensors, and, as in bioaffinity sensors, the analog never escapes from the system. However, unlike the bioaffinity sensor, the analog is retained in the vicinity of the antibody not by a membrane, but by the flexible link. If the concentration of analyte in the surrounding medium goes down, the "captive" analog can once again compete effectively for the antibody binding sites, reversing the analyte binding without any partial or temporary antibody denaturation, and thereby restoring the sensor to baseline without any negative impact on antibody capacity. This new approach, called the "Reversible Competitive Recognition Unit (RCRU)" (U.S. Pat. No. 5,156,972, Oct. 20, 1992, "Analyte Specific Chemical Sensor with a Ligand and an Analogue Bound on the Sensing Surface", D. Issachar), has been proposed for use in a variety of nonspecific transduction immunosensors, e.g., immunofluorescence techniques. It also appears that the RCRU concept might be utilized with other types of biological components, such as other types of proteins, lectins, antibody fragments, polypeptides, synthetic peptides, and receptors. Therefore, it should be possible to design RCRU-based biosensors for the specific detection of a wide range of analytes, including very low-molecular-weight haptens which could not be detected with the use of antibodies, and, because there is no semi-permeable membrane, the detection of high-molecular-weight analytes as well. However, while the RCRU approach eliminates some of the limitations associated with bioaffinity sensors, e.g., response and recovery times and molecular weight limitations, and also expands the number of different analytes which may be detected, the RCRU approach still suffers from the problems associated with the impact of nonspecific and specific interferences on the nonspecific transduction of the prior art.

Almost any device or process intended for the detection of very dilute analyte concentrations—whether based on conventional instrumentation such as IR or Raman spectroscopy, or on the newer biosensor techniques—must be coupled with a sampling system or process capable of concentrating the analyte with respect to sample volume. For example, solid sorbent systems such as activated charcoal, tenax, or a quartz fiber bundle, or liquid scrubbing systems may be used to concentrate vapor samples. When a solid sorbent is used, large volumes of air are first pulled through the solid sorbent, permitting the analyte to adsorb onto the surfaces of the sorbent. The sampling air is then turned off, and small volumes of heated gas are driven through the solid sorbent to desorb the analyte and flush the concentrated analyte molecules through a sample transfer line to the detector. However, such sampling systems or processes have many drawbacks of their own. Those same qualities which make the solid sorbent surfaces efficient at collecting the analyte molecules during adsorption also make the surfaces retain the analytes during desorption; and the "sticky" molecules which are successfully driven off tend to resorb onto the walls of the sample transfer line, never reaching the transducer. This leads to decreased overall sensitivity. In addition, because surface adsorption is a relatively nonspecific mechanism, many other sample constituents are concentrated and transported to the transducer in addition to the analytes, increasing the background "noise" and contributing to false alarms and a further decrease in sensitivity. Interferents can become permanently attached, gradually poisoning the surface and preventing the analyte from adsorbing; and only frequent calibration with analyte standards can detect this particular problem. Liquid scrubbers are messy, require consumables—such as water— and have a tendency to overflow in hot, humid climates. Like solid sorbents, liquid scrubbers are nonspecific, i.e., they will collect and concentrate hundreds of other compounds in addition to the analyte, thereby raising the background signal or noise, and reducing the sensitivity that could otherwise be achieved with a clean sample. Both solid sorbents and liquid scrubbers are batch samplers, which means that the detector will not be able to respond any more quickly to high analyte concentrations than to low. Both can produce "ghosts," i.e., residual analyte left in the sampler or transfer line by high concentrations of analyte collected in one sampling cycle, which is then flushed out in following sampling cycles, producing false alarms. High-volume samplers of either design tend to be large and to require a considerable amount of power for operation.

It is thus apparent that a need exists for a methodology and apparatus which provides a direct analysis and specific identification of multiple analytes without extensive sample preparation.

It is also apparent that a need exists for an improved process and apparatus based on Raman spectroscopy in which the analyte is specifically collected, concentrated, and isolated from other sample constituents for reliable analysis of trace analytes.

It is also apparent that a need exists for an improved process and apparatus based on biosensor technology in which the analyte itself is detected and specifically identified, rather than a "biological signal" or secondary signal being monitored, for reliable analysis and/or specific identification and/or quantification of trace analytes.

It is also apparent that a need exists for an improved process and apparatus based on biosensor technology in which the biological component itself is directly monitored, to prevent false responses due to the biological being denatured, inactivated, poisoned, or leached.

It is also apparent a need also exists for a methodology and apparatus which provides a direct, nondestructive analysis of biological preparations, such as imniobilized biological products, to optimize manufacturing and to detect product degradation during storage.

It is also apparent that a need also exists for a specific sample concentration approach in which the analyte and only the analyte is collected and concentrated, and thereby separated from other sample constituents prior to analysis.

BRIEF DESCRIPTION OF THE INVENTION

It has now been found that the unique correlation between Raman spectral information and the structure and chemistry of biological materials, coupled with the impact of binding between a ligand and a biological macromolecule on the three-dimensional structure and the intramolecular-intermolecular interactions of the biological material and of the ligand itself, as reflected in the resulting impact on the frequencies and forms of the normal modes of vibration of both materials as observable in the Raman spectra of the biological and the ligand, can be used as the basis for a highly specific process or device to detect the presence of analytes. It has now been found that, to detect a given analyte, it is possible to use a biological for which said analyte is a ligand, i.e., a biological capable of binding said analyte at its active site and thereby forming a biological-analyte (biological-ligand) complex. With the proper selection of said biological, coupled with the judicious selection of Raman spectroscopy techniques and instrumentation, changes in the Raman spectrum of said biological material induced by the presence of said analyte can be used to determine that the analyte is present. In fact, it has now been found that by analyzing the frequencies, intensities, and polarization states observed in the Raman effect, each of a plurality of analytes (i.e., ligands) that may interact with a single, given biological material can be individually and specifically identified. Despite the exceptional size and complexity of many biologicals, and the resulting complexity of their spectra, a given analyte may have a striking impact on the Raman spectrum of a given biological. That impact is highly reproducible, and is completely unique to the analyte that becomes bound to the active site of the biological. Even when the plurality of analytes (and cross-reactive potential interferents) capable of binding to the biological are very small in size, the binding of each analyte will result in a biological-analyte complex of unique chemistry and, hence, a unique Raman spectrum. It has now been found that this attribute may be used in a variety of ways in the detection and identification of analytes. For example, a baseline spectrum of the biological may be obtained. Then, as the biological is brought into contact with a material to be analyzed (i.e., containing the analyte), the Raman spectrum is monitored and compared against the baseline spectrum. Changes in the baseline spectrum mean that one or more materials capable of binding with the biological are present. If it is known that the material may differ only by the presence or amount of a single analyte, then the changed spectrum of the biological indicates the analyte must be present. For specific identification (and, in particular, for use with materials that may vary widely in composition), reference spectra may be obtained before the analysis is initiated. These reference spectra may include, for example, the spectra of a plurality of biological-analyte complexes. The biological is then exposed to the material to be analyzed, and its spectrum monitored as before. If a change in the spectrum is observed, that new spectrum is compared against the library of reference spectra. If the new spectrum matches one of the reference spectra, then a specific biological-analyte complex must, by definition, have been formed and, hence, a specific analyte must have been present in the material.

The presence of the analyte in the active site will result in new lines being present in the Raman spectrum due simply to the presence of the new chemical moiety, i.e., the analyte itself (or analyte residue, in the case of, for example, enzyme-inhibitor complexes). The wavelengths associated with such lines may be monitored and, when the lines appear, the presence and/or identity of the analyte may be inferred. In addition, it has been found that bonds formed between the biological and the analyte (or analyte residue, in the case of, for example, enzyme-inhibitor complexes) will be reflected by the formation of new lines in the Raman spectrum which may be used in the detection and analysis of said analyte. Further, it has now been found that Raman lines associated with bonds or moieties within the biological itself can be uniquely affected by binding with a given analyte and, hence, Raman lines within the biological may be monitored to detect and identify analytes. Similarly, it has been found that a given biological will have an impact on the Raman spectrum of the analyte or analyte residue bound to the biological, and that Raman lines associated with bonds or moieties within a bound analyte moiety may be monitored instead of, or in addition to, lines associated with bonds or moieties in the unbound analyte, the biological, or between the biological and analyte.

Individual cells such as microorganisms, blood cells, and infected tissue cells may be considered to be exceptionally large and complex chemicals and, as such, in possession of completely unique Raman spectra. It has also now been found that, with the judicious selection of biologicals capable of binding such cells and the Raman techniques and instrumentation, Raman spectral analysis of a biological-cell complex may be used to detect the presence of and to uniquely identify the cell bound within the complex. As with less complex analytes, Raman spectral lines associated with the biological, lines associated with bonds between the biological and the cell, and/or lines associated with the cell itself may be used in the detection and identification process. It has also now been found that Raman spectral analysis of the biological-analyte complex may be used to identify other types of microorganisms such as viruses, spores, and pollens, which are not usually considered to comprise "cells".

It is known that the intensity of Raman scattering is proportional to the number of molecules irradiated. It has now been found that Raman spectroscopic techniques can be used to make quantitative measurements of analytes that have interacted with the biologicals, whether the portion of the Raman spectrum that is being monitored is associated with bonds within the analyte, bonds between the analyte and the biological, or bonds entirely within the biological material itself.

It is known that samples may be examined in any physical state by Raman spectroscopic techniques; spectra can be obtained from pure liquids, solutions, crystals, polycrystalline powders, fibers, and surface films. It has now been discovered that analytes will interact with and be bound by biological materials whether the biological material is solvated, partially hydrated, or essentially dry; and in so doing, will cause the same types of alterations to the biologicals' baseline Raman spectra when the biological is essentially dry as when interacting with fully solvated biologicals. Accordingly, it has now been found that essentially dry or partially hydrated biologicals may be used in the direct detection and analysis of airborne vapors or particulates, as well as solvated biologicals being used in the direct detection and analysis of dissolved or suspended analytes.

Selection of the biological and the Raman techniques and instrumentation to be used or a given analysis depend on the analyte(s), the material to be analyzed, and the information desired. It has been shown that a wide range of techniques and instrumentation may be used effectively to gain the desired specificity and sensitivity, including, for example, RRS and microprobe techniques. It has also now been found that biological materials retain their binding activity when suitably immobilized, and will interact with and bind analytes while in this immobilized state, and will exhibit the same types of changes in the baseline Raman spectrum when the biological-analyte complex is formed with an immobilized biological as when the biological materials are in solution or suspension. Further, it has now been discovered that when the biological is suitably immobilized on metal surfaces, the biological and biological-analyte complexes will exhibit intensified Raman signals due to the surface-enhancement phenomena. Accordingly, SERS and SERRS techniques may be used to gain additional sensitivity and specificity in the detection and identification of analytes bound to and captured by biological materials.

It has also been found that SERS techniques can be utilized to greatly simplify the identification of microbial analytes. As discussed above, RRS can be a very powerful tool for probing select molecules within a microorganism, and thereby gaining specificity. Yet many laser wavelengths cannot be used for microbial analysis because they induce fluorescence so intense it overwhelms even the strong RRS signal. It has now been found that, by using SERS to quench fluorescence, a far wider range of wavelengths can be used to induce resonance in a far wider range of cell structures and components, while simultaneously enhancing the RRS signal. At the very least, SERS can enable the generation of strong, fluorescence-free Raman signals from pathogens excited in the visible region, where lasers are small, low-power, readily available, rugged, and inexpensive. Second, as discussed above, some bacterial cell constituents vary widely in relative content during different points in the growth cycle or due to different environmental conditions. Such variability is observed primarily in the spectral contributions from the cytoplasm constituents rather than those from the cell wall or membrane; if the spectral signals are a combination of contributions from both the cell surface markers and the variable cytoplasm constituents, the spectra can be dependent on the stage of growth/environmental conditions, whereas if the spectral information is limited to contributions from the cell surface markers, much of the variability can be eliminated. It has now been found that, since the SERS effect is limited to molecules in extremely close proximity to the roughened metal surface, SERS will probe cell surface structures selectively. For example, it has now been found that a 251 nm excitation can be used to produce a surface-enhanced resonance Raman scattering (SERRS) spectrum from quinones without inducing resonance in dipicolinate; and excitation at 222 and/or 218 nm can be used to produce a SERRS spectrum from protein without introducing confusion from the RNA content. By eliminating spectral contributions from variable cell cytoplasm constituents, the present invention eliminates one source of potentially false responses and simplifies the database that is needed for reliable identification of microorganisms in complex mixtures or samples.

In addition, it has now been found that a roughened electrode may be used as the SERS-active surface, and that alterations in the electrode potential may be used to adjust the orientation of the biological and/or biological-analyte complex, thereby adjusting the moieties in the closest proximity to the surface and thereby adjusting the degree of enhancement of the signals from moieties within the biological and/or biological-analyte complexes. Accordingly, an electrode may be used to enhance both the sensitivity and the specificity of the analyte detection and analysis process, either by setting the potential to maximize the enhancement of selected Raman bands unique to the presence and/or identity of the analyte, or by cycling the potential and generating multiple spectra (i.e., a spectrum produced at each of several electrode potentials) for comparison against a library of reference spectra generated at the various electrode potentials.

Finally, it is known that, as with biological-analyte complexes, the fully reactive, thermally or chemically denatured, and immobilized forms of a given biological are essentially different chemicals, having different three-dimensional structures and intramolecular interactions; hence, the fully reactive, thermally or chemically denatured, and immobilized forms of a given biological have different and unique Raman spectra. It is known that Raman spectroscopy is very useful for examining conformational changes that occur as a result of denaturation, chemical modification, lyophilization, and crystallization. However, no direct correlation has previously been drawn between a biological's conformation and the biological's potential for binding or complexing with a ligand (hereinafter called "reactive capacity"); instead, all prior art for the evaluation of the ability of a biological to complex with a ligand has been based on actual measurement of complex formation, i.e., through destructive biological activity assays, as discussed above. However, it has now been shown that there is indeed a direct correlation between the Raman spectrum of a biological and its reactive capacity, and that said reactive capacity analysis is a useful nondestructive mechanism both for predicting the potential biological activity of a biological and for determining causative factors contributing toward altered potential biological activity. In fact, reactive capacity analysis may be considered to be a four-step process for the detection of an "analyte", i.e., the causative factor. First, the biological is brought into contact with the "analyte". The "analyte" may be, for example, heat or chemicals that are capable of "complexing" with the biological, i.e., capable of interacting with the biological in such a way that chemical changes characteristic of denatured biological, altered oxidation state, altered aggregation state, altered peptide backbone structure, etc., are induced. As with chemical or microbial analytes, these chemical changes in the biological are reflected in the Raman spectrum of the biological, and are characteristic of and unique to the "biological-analyte complex", i.e., characteristic of and unique to the thermally or chemically denatured biological or the oxidized or reduced biological, etc. Hence, through the generation of Raman spectral information from the biological of interest and subsequent comparison of that information with a library of model reference spectra of biologicals of known biological activity (i.e., partially or completely denatured biologicals whose biological activity was subsequently measured using conventional activity assays), it is possible to identify the "analyte" that formed the "complex" (i.e., the factor that partially or fully denatured the biological), and thereby predict the potential biological activity of the sample material.

Further, it has now been found that it is possible to detect and quantify each of a plurality of such "complexes", i.e., a plurality of discrete forms of a given biological in a mixture. As with chemical and microbial analytes, factors that denature or alter the state of a biological yield a form of the biological that has a unique spectrum. Even when several different forms of the same biological are present, they may be individually identified and even quantified through their Raman spectra. Hence, even if the conditions in a material are such that some of the biological is completely denatured and some retains full biological activity, Raman reactive capacity analysis may be used to determine the amount of each form that is present and, hence, the overall reactive capacity (i.e., the overall potential biological activity) of the mixture.

Therefore, Raman spectroscopic tools may be used to nondestructively monitor the biological components themselves in a biosensor process or device, during the detection and analysis of analytes performed in accordance with this invention, to determine whether the biologicals are fully reactive and capable of binding their analytes. For example, reference spectra may be obtained not only from the biological-analyte complex, but also from the various forms of the biological exhibiting altered reactive capacities. Then, as the baseline Raman spectrum is being monitored during the analysis of a material (e.g., during continuous monitoring of air), any changes observed in the baseline spectrum may be compared not only against reference spectra of the various biological-analyte complexes, but also against reference spectra of the various forms of the biological. If the baseline spectrum changes into a spectrum corresponding to that of denatured or partially denatured or otherwise less reactive form of the biological, then the information may be used to mitigate the impact of the change in biological activity, e.g., adjust the sampling rate, modify the mathematical manipulations used to quantify the analyte, or even replace the biological. Hence, in accordance with this invention, the Raman reactive capacity analysis of the biological itself may be used to rectify one of the most serious problems encountered with prior art biosensors, i.e., the relative fragility of the biological components.

Further, it is known that the microenvironment surrounding biologicals, especially immobilized biologicals, may be very different from the environment of the bulk medium, i.e., the surrounding solution or air. Hence, it has now been found that by monitoring the Raman scattering spectrum of a biological and performing reactive capacity analyses, it is possible to gain far more information about the status of the biological, i.e., about its microenvironment and the impact of that microenvironment on the biological, than can be achieved, for example, by monitoring the pH, temperature, or the ionic concentration of the bulk medium. Accordingly, it has now been found that Raman reactive capacity analysis may be used to identify (and to mitigate) undesirable environmental factors adversely impacting biological activity. For example, Raman reactive capacity analysis might detect a form of the biological characteristic of decreased biological activity due to high pH while a material is being monitored for an analyte; some acid or a buffer might be added to adjust the pH to a level suitable for optimal biological activity.

It should be noted that Raman reactive capacity analysis techniques in accordance with this invention may be used at other times and in other ways than during the detection of a chemical or microbial analyte. For example, it might be used during manufacture and storage of biological preparations, including synthesized, extracted, purified, lyophilized, crystallized, and/or immobilized preparations, whether or not said biologicals are intended for later use in a biosensor, and whether or not said biosensor utilizes a Raman transducer. For example, immobilized enzyme preparations may be analyzed to predict their ability to synthesize a given reaction product. (In this example, the "analyte" is the process used to immobilize the biological.) The library of model reference spectra is prepared from a number of different immobilized preparations whose biological activity has been determined using conventional enzyme activity assay techniques. The immobilized preparation to be analyzed is exposed to radiation at a suitable wavelength, its resulting Raman spectrum collected and processed, and the measured spectrum of the preparation then compared against the library of model reference spectra to determine the reactive capacity of the preparation. This reactive capacity analysis may be used, for example, to screen batches of preparations to identify those that have been improperly processed, or to detect biological preparations that have become degraded during storage. Similarly, reactive capacity analysis may be used to monitor extraction, purification, chemical modification, synthesis or biosynthesis, lyophilization, and crystallization procedures (in situ, if desired) to optimize the yield, screen batches to identify those that have been improperly processed, detect preparations that have become degraded during storage, and so forth.

Finally, it has been discovered that this invention is not limited to a narrow category of biologicals. Prior art biosensor techniques are often restricted to a single type of biological component. For example, most fluorescence biosensor techniques can only be used with antibodies; they cannot be used with enzymes, receptors, or nucleic acids. Most electrode biosensor techniques can only be used with a particular category of enzymes; they cannot be used with other types of enzymes, or with antibodies or nucleic acids or receptors; and so forth. However, it has now been shown that Raman scattering spectral analysis for the detection and identification of an analyte complexed with a biological may be used with virtually any biological, including proteins and protein complexes, nucleic acid materials, acceptors and receptors, peptides, lectins, saccharides, carbohydrates, lipids and lipid complexes, other biological macromolecules and complexes, ligands such as antigens, haptens, inhibitors, agonists, and antagonists, and even membranes, organelles, cells, and tissues, as will be described. Similarly, it has now been discovered that Raman reactive capacity analyses (i.e., predicting their potential ability to form complexes with ligands from Raman spectral information) may be performed on this wide range of biologicals.

Briefly, then, the present invention is a process and an apparatus for the direct detection and identification, qualitatively and/or quantitatively, of one or more analytes, involving four steps. In the first step, an analyte is brought into contact with a suitable "bioconcentrator" (i.e., a biological component used in accordance with this invention), in such a fashion that some of the analyte may become bound to or complexed with the bioconcentrator. In the second step, the bioconcentrator-analyte complex is exposed to radiation of one or more predetermined wavelengths to produce Raman scattering spectral bands. In the third step, at least a portion of the Raman scattering spectral bands are collected and processed by a Raman spectrometer, and converted into an electrical signal. Finally, in the fourth step, the electrical signal is analyzed by comparison against one or more electrical signals of baseline spectra to detect and/or identify, qualitatively and/or quantitatively, the analyte. The baseline may be, for example, a spectrum taken of the biological just before it is brought into contact with the material to be analyzed. The baseline may also be a library of model reference spectra, i.e., spectral information previously generated with known bioconcentrator-analyte complexes and then suitably stored in memory for purposes of comparison.

The same four steps of the present invention may also be used in the reactive capacity analysis of the bioconcentrator, or other types of biologicals. In this case, the "analyte" with which the biological "complexes" may be, for example, heat or chemicals capable of denaturing the biological, environmental factors capable of altering the oxidation state or spin state or aggregation state of the biological or its peptide backbone structure, and so forth. The baseline may be, as before, a spectrum taken of the biological just prior to being brought into contact with the "analyte". The library may contain model reference spectra of fully active and partially or completely denatured or otherwise degraded bioconcentrator. When the bioconcentrator itself is analyzed, the results of the reactive capacity analysis may be used to affect or alter or optimize the processes targeted toward detection and analysis of the analytes in which the bioconcentrator is involved, in accordance with this invention. When Raman reactive capacity analysis is performed on other types of biologicals, the resulting information may be used to adjust or optimize a process in which the biological is involved, e.g., extraction or chemical modification or purification of the biological itself.

Because a biological component, e.g., the bioconcentrator, is involved, this invention may be considered to belong to the technology known as biosensor technology. Because Raman scattering spectroscopy is an optical technology and the term "optrode" has been used for biosensors based on optical transduction, this invention is now referred to as "Raman Optrode" technology. Alternatively, however, because the basic steps and even the underlying processes and phenomena involved in this invention differ significantly from prior art biosensor technologies, the present invention may be envisioned instead to be a highly specific sampling process or device for use with detection or analysis or monitoring processes or devices based on Raman spectrometry. Hence, the biological component as used in this invention is now called a "bioconcentrator" in recognition that it functions, essentially, to specifically collect and concentrate the analyte, in an approach that is a significant improvement over other sample concentration processes or devices such as solid sorbents or liquid scrubbers.

There are many forms which the process or device of this Raman Optrode invention may take. For example, it should be noted that the step in which the bioconcentrator binds with the analyte and steps in which the Raman spectrometer and electronics generate and analyze the spectral information may be done independently, and may even be performed at different times, hours or days apart, and/or at different locations. For example, the bioconcentrator may be used to bind with or collect and concentrate the analyte in one location, said bioconcentrator-analyte complex then being transported to a second location where the Raman spectrum analysis and analyte detection/identification is performed. However, the bioconcentrator and the Raman spectrometer and electronics certainly may be integrated into a single device, with analyte collection and signal transduction and analysis performed simultaneously and even, if desired, fully automatically. A Raman Optrode device designed in accordance with this invention may have sufficient electronics and software that said device can operate unattended, generate alarms automatically when analyte is detected, produce a visual display and/or hard copy printout which presents information on the identity and quantity of the analytes which have been detected, automatically replace any "spent" bioconcentrator (i.e., bioconcentrator whose reactive capacity has been significantly reduced by any mechanism, including, for example, analyte binding, cross-reactive interferent binding, denaturation, etc.), and/or send information to a computer for further processing (e.g., process control functions).

The bioconcentrator of the present invention may be any of a wide variety of molecules, macromolecules, complexes, and fragments, including but not limited to enzymes, antibodies, antibody fragments, other biologically active proteins such as hemeproteins, peptides (including synthetic peptides), other biological molecules such as glycosphingolipids, lectins, lipids, phospholipids, nucleic acids, or pathogen adhesion factors, complexes such as receptors, or receptor subunits, or membranes, organelles, or cells, or tissues or complexes containing these components. In addition, especially if the analyte itself is a biological such as an enzyme, antibody, receptor, nucleic acid, or the like, the bioconcentrator may be any of a wide variety of ligands which normally bind to such biological analytes, said "ligand bioconcentrator" being selected from a list including but not limited to enzyme substrates, co-factors, or inhibitors, antigens, antigen analogs, or haptens, agonists or antagonists, sugars, and the like. The bioconcentrator may be selected on the basis of a number of practical criteria, notably the type and number of analytes to be detected; the bioconcentrator's ability to bind or capture the analyte(s) with the desired specificity and affinity, its stability, its availability, and its Raman scattering spectral characteristics; and the costs of manufacturing the bioconcentrator component.

It should be noted that this invention, with the judicious selection of bioconcentrator(s), may be used to detect virtually any chemical analyte including molecules ranging in size, molecular weight, and complexity from single atom ions to proteins and nucleic acids to biological complexes such as receptors and organelles. It should further be noted that this invention is not limited to the detection and identification of chemical compounds or complexes, but also can be used to detect and identify microorganisms such as viruses, bacteria, rickettsias, fungi, pollen, spores, algae, diatoms, etc., and other types of living organisms or cells, e.g., diseased or infected cells, different types of blood cells, and the like. It should also be noted that the invention may be used to detect and identify subcellular components and structures. It should further be noted that this invention may be used to detect nonviable organisms and different between "living" and "non-living" organisms; and to detect and differentiate between toxic and non-toxic forms of chemicals or biological macromolecules, e.g., between toxins and their toxoids.

It should also be noted that this invention may be used to directly detect and/or identify and/or quantify analytes which either are in liquid media (either aqueous or nonaqueous and dispersed or dissolved or carried therein) or are airborne (i.e., are vapors, aerosols, or particulates). Moreover, the bioconcentrator does not have to be solubilized or solvated during exposure to an airborne analyte or during subsequent transduction. Dry or partially hydrated biological components may be exposed directly to air samples, and will react directly with airborne analyte vapors, aerosols, or particulates. However, the bioconcentrator certainly may be in solution or immobilized on a surface which is coated with or submerged in liquid during use; and the Raman Optrode invention does cover processes and devices in which samples are in solution, or are scrubbed into solution, prior to binding with the bioconcentrator.

It should further be noted that the bioconcentrator may or may not be immobilized on a substrate during either the binding step or the Raman spectrum generation/analysis steps. The term "substrate" has a broad definition in the context that the bioconcentrator is immobilized, i.e., its free movement through a medium is restricted, even if said bioconcentrator is not supported on a solid or porous supporting surface, e.g., through incorporation into or entrapment by a matrix such as a protein or polymer film or porous material which limits the movement of the bioconcentrator. The bioconcentrator does not have to be immobilized in accordance with this invention, but may instead be solubilized or solvated in a liquid medium; or may be in solid form itself, e.g., crystallized or powdered, when exposed to and binding with the analyte and/or when subsequently exposed to the exciting light for generation of the Raman scattering spectrum. The bioconcentrator may remain as a solvated or solubilized biological or as a powdered or crystalline material, without immobilization at any point in the collection/detection/monitoring/analysis process. However, the bioconcentrator certainly may be immobilized on a solid or porous supporting surface or within a film or porous medium throughout the analyte binding and Raman analysis steps. Alternatively, the bioconcentrator may first be exposed to the analyte while in a free (i.e., not immobilized) form and subsequently immobilized (e.g., adsorbed onto or captured within a solid support or surface or porous material or film or medium) for the Raman spectrum generation and analysis steps.

If immobilized, the bioconcentrator may be immobilized by any of a wide variety of mechanisms as are known by those versed in the art, including, for example, adsorption, cross-linking, adsorption coupled with cross-linking, covalent bonding, entrapment, etc., and may be immobilized on a surface or within a membrane, including a membrane formed entirely and solely of the biological component itself. If immobilized on a substrate, the surface on which (or film or material within which) the bioconcentrator is immobilized may be of virtually any material with which the bioconcentrator, analyte(s), and sample(s) are physically and chemically compatible, and may be in any of a wide variety of configurations, such as badges, tickets, dipsticks, small spots on paper, plastic, polymer, cloth, or other material, optical fibers or crystals, small beads, glass slides, tubes, metal films, paper or plastic tapes, and so forth. The surface or film or material to be used for a given application, and its configuration, will be dictated by the sampling procedure considered optimal for said application.

The bioconcentrator may be a single biological component, and the Raman Optrode process or device dedicated to the detection of a single analyte. Alternatively, the bioconcentrator may be a single biological component capable of complexing with a plurality of analytes, and the Raman Optrode used to detect and identify at least some of the compounds or microorganisms capable of complexing with the bioconcentrator. In yet another alternative, the bioconcentrator may be a mixture of a plurality of biological components, each capable of complexing with one or more different analytes, thereby making it possible to detect, analyze, and monitor a large number of analytes and/or multiple analytes with widely diverse physical and chemical characteristics. The Raman Optrode may also have a sampling system or subsystem in which one or more bioconcentrators are immobilized on one or more areas of, for example, a solid support or within a membrane; the Raman spectrometer instrumentation can be designed to collect individual spectra from various locations within these different areas, either simultaneously or sequentially, thereby also making it possible to detect and analyze the plurality of analytes capable of binding with the different bioconcentrators at the different locations.

Any light source suitable for generating the desired Raman spectral information may be used, including but not limited to one or more lasers operating in the deep UV, near UV, visible, and/or near-infrared spectral ranges, as well as other suitable light sources. If resonance Raman techniques are to be used, a light source may be selected that will excite resonance in bonds within the bioconcentrator, in bonds within the analyte, or in new bonds that form between the bioconcentrator and the analyte in the complex. The bioconcentrator may be exposed to irradiation from the exciting light during and throughout exposure to the sample or sample stream, either continuously or at periodic intervals, thereby permitting rapid or continuous detection and analysis or "real time" monitoring of the sample or medium or environment. Alternatively, the bioconcentrator may be exposed to the sample first, and then later coupled with or inserted into or scanned by a Raman spectrometer device for subsequent analysis.

The Raman Optrode process or device may utilize a single exciting wavelength from a single light source. Alternatively, more than one exciting light wavelength, produced by one or more light sources, can be used in a process or device in accordance with this invention. For example, two or more laser wavelengths, each capable of inducing resonance in different bonds within the bioconcentrator-analyte complex, may be used sequentially to generate RRS spectra, said spectra being sequentially collected and processed and analyzed to produce a "three-dimensional spectrum". As another example, an NRS spectrum may be produced at one wavelength to monitor the status of the bioconcentrator itself, while resonance may be induced in the complexed analyte moiety at another wavelength for sensitive RRS detection of a given analyte. However, a single wavelength certainly may be used, if desired.

Any suitable form or configuration of Raman spectroscopy or Raman spectroscopic technique as are known to those versed in the art may be used in accordance with this invention during the Raman analysis step, including but not limited to normal Raman scattering (NRS), resonance Raman scattering (RRS), surface enhanced Raman scattering (SERS), surface enhanced resonance Raman scattering (SERRS), SERS or SERRS coupled with an electrode, Coherent Anti-Stokes Raman Spectroscopy (CARS), stimulated gain (SRG), inverse Raman spectroscopy (IRS), Molecular Optical Laser Examiner (MOLE) or Raman microprobe or Raman microscopy or confocal Raman microspectrometry, three-dimensional (3-D) or scanning Raman, Raman saturation spectroscopy, time resolved resonance Raman, Raman decoupling spectroscopy, UV-Raman microscopy, and/or hyper-Raman scattering. Similarly, the Raman spectrometer hardware and components utilized during the Raman analysis step may be selected from a list including, but not limited to, band-pass filter systems, filter-grating or prism-grating dispersive systems, multichannel systems, scanning multichannel systems, or multiplexing spectrometers such as Hadamard transform or Fourier transform or stationary transform systems, acousto-optic or integrated optic acousto-optic systems, imaging systems, or microprobe or microscopy systems, or fiber optic systems, etc., depending on constraints imposed by the desired parameters for the method or process or apparatus or device, including, for example, the desired sensitivity, specificity, accuracy, precision, and response time, the laser wavelengths to be used and the resulting wavebands to be monitored, the number of bioconcentrators to be used and the number of analytes to be detected, the desired size, weight, and ruggedness of the system, target procurement and/or operating costs, etc. In each case, the Raman spectrometer system or subsystem receives as its input the emitted radiation from the bioconcentrator or bioconcentrator-analyte complex or biological, processes it, and focuses the output to impinge on a detector or detectors capable of translating the optical signal into an electronic signal. A preferred form may be a multiplexing or multi-channel design, as these Raman spectrometer designs may provide a superior response time and sensitivity. Another preferred form may be an imaging design, as these Raman spectrometer designs enable the use of an array of bioconcentrators for the simultaneous detection and identification of many different analytes. For ultra-trace analyte detection, a preferred form may also include the use of microprobe or microspectrometry techniques and equipment, whether or not incorporated into an imaging Raman spectrometer system. Nevertheless, for other applications, a much simpler and less costly approach may be preferable. For example, if a single analyte is of interest and the sample to be analyzed is relatively clean and consistent in its composition, such that only one or a few wavebands must be monitored, a band-pass filter may be the design of choice. A band-pass or optical filter design might be used, for example, in a Raman Optrode for the detection of nitrogen mustard breaking through a charcoal filter, using DNA as the bioconcentrator and monitoring the spectral lines at 1492 and 1530 cm$^{-1}$.

Once the Raman spectrometer has processed the light signals into electronic signals, the electronic signals are then compared with a baseline spectrum generated prior to bringing the material into contact with the bioconcentrator, or with a library of reference Raman spectra that were prepared in advance and stored in the Raman Optrode's memory for the purposes of such a comparison, or both. In accordance with this invention, the library may include, for example, spectra from the fully reactive bioconcentrator, degraded or denatured bioconcentrator, various bioconcentrator-analyte complexes (which may be at various bioconcentrator/analyte concentration ratios for quantitative analysis), and/or bioconcentrator-interferent complexes. The spectral comparison is used as the basis for detecting and/or identifying and/or quantifying any analyte bound to the bioconcentrator, and/or for determining any partial or complete denaturation, poisoning, or change in the state of the bioconcentrator or biological itself.

It should be noted that the spectral comparison/analysis may involve the generation of difference spectra, or the comparison of first or second or third or fourth derivative spectra, or selected wavelength monitoring, or other types of manipulations and calculations suitable for the application at hand as are known by those versed in the art. In a preferred form, difference spectra are used, as these are generally more sensitive to small changes in spectra than other forms of analyses. When different Raman conformation markers overlapped to the point they cannot be instrumentally resolved from one another, manipulations such as, e.g., deconvolution, Fourier deconvolution, maximum entropy, or Monte Carlo methods may be used to enhance the separation of such bands or simulate a resolved spectrum. Spectral analyses in accordance with this invention may be performed using any suitable algorithms or combination of algorithms such as are known to those versed in the art (including but not limited to, for example, similarity, correlation, and distance measurements, library search methods such as probabilistic based matching, adequate peak search, and principal component analysis, nonlinear artificial neural network approaches, fuzzy logic, or data fusion, linear, classical least squares, principal components regression, partial least squares, multivariate analysis or patch multivariate analysis, or standard additions techniques, etc.)

For Raman Optrode processes and devices which are intended to provide precise quantitative information, a variety of calibration procedures may be used. For example, external "standards" may be used, with the intensity of one or more spectral bands within the standards being compared with the intensity of one or more lines within the Raman spectrum of the bioconcentrator-analyte complex. Split reference beams or reference cells may also be used, particularly in Raman spectrometer designs that utilize two detectors for this purpose. Some part of the bioconcentrator may be protected so that it is not exposed to the sample/analyte, and one or more lines in the spectrum of the protected bioconcentrator used for comparison with one or more lines in the spectrum of the bioconcentrator which is exposed. In yet another approach, one or more wavelengths in the spectrum of the bioconcentrator which are known to remain unchanged during sampling and analysis can be compared with one or more lines which are known to change upon binding with the analyte or upon denaturation or poisoning. In addition, lines within the spectrum of the bioconcentrator and/or bioconcentrator-analyte complex can be compared with lines in the spectrum of an internal standard added to the sample and/or co-immobilized with the bioconcentrator for that specific purpose, in accordance with this invention.

Similarly, for Raman Optrode reactive capacity analyses intended to provide precise quantitative information, a variety of calibration procedures may be used. For example, external "standards" may be used, with the intensity of one or more spectral bands within the standards being compared with the intensity of one or more lines within the measured Raman spectrum of the biological. Split reference beams or reference cells may also be used, particularly in Raman spectrometer designs that utilize two detectors for this purpose. One or more wavelengths in the spectrum of the biological which are known to remain unchanged during analysis can be compared with one or more lines which are known to change upon denaturation, changes in oxidation or spin or aggregation state, changes in the peptide backbone structure, etc. In addition, lines within the measured spectrum of the biological can be compared with lines in the spectrum of an internal standard added to the sample and/or co-immobilized with the biological (if the preparation is an immobilized preparation) for that specific purpose, in accordance with this invention.

It should also be noted that the Raman Optrode may be used to detect molecules containing unusual or uncommon isotopes at one or more positions in the analyte structure, i.e., the Raman Optrode is capable of distinguishing between the labeled and unlabeled molecules, in addition to distinguishing between different chemical species. These isotopes may be radioisotopes, "stable labels" such as deuterium or carbon-13, or a combination thereof. As with analysis of different chemicals, Raman Optrode analysis of different isotopically-labeled species may be quantitative as well as qualitative. Hence, the Raman Optrode technique may be used as a quick and simple means for analyzing the purity of synthesized labeled preparations. Raman Optrode techniques can also be used for ensuring that labels have been inserted at the correct positions in the molecule.

Finally, it should be noted that a "complete" Raman spectrum does not have to be obtained, although it may be. Raman Optrode processes and devices may be designed to generate, monitor, or analyze a "full" spectrum, one or more partial spectra, a handful of spectral bands, or a single spectral line, depending on the application intended for the Raman Optrode process or device, and the amount of information which is desired. Further, said processes and devices may monitor (a) new lines or bands due to the addition of the spectrum of the analyte; (b) changes in the baseline spectrum of the bioconcentrator itself which are caused by binding between the analyte and the active site of the bioconcentrator (e.g., changes in the spectrum caused by changes in the three-dimensional conformation or intramolecular interactions of the bioconcentrator); (c) new spectral bands caused by Raman scattering from new bonds or moieties formed when the analyte binds with the bioconcentrator; (d) changes in the spectrum of the analyte itself caused by binding with the bioconcentrator; or (e) some combination thereof.

As already discussed, this invention includes any process or device in which a biological material or component thereof is analyzed using Raman reactive capacity analysis techniques, i.e., when the "analyte" to be detected is a factor capable of interacting with the biological and thereby causing the biological to be partially or completely denatured, or its oxidation or aggregation or spin state to be altered, or the peptide backbone structure to be changed, or the biological to be immobilized, etc. As with chemical or microbial analytes, Raman reactive capacity analysis may be performed on biologicals that are dry, powdered, crystalline, particulate, partially or completely hydrated or solubilized, suspended, or dissolved. In addition, the analyses may be performed on a single biological or a plurality of biologicals, and on a wide variety of biologicals. Further, Raman reactive capacity analysis may be performed when the biological has interacted with more than one factor capable of affecting its state or potential biological activity; and the degree of interaction, i.e., how much of the biological exists in each of the resulting forms, can be quantitatively measured.

In accordance with this invention, Raman Optrode devices or processes may be designed so that any otherwise adverse impact on Raman Optrode response due to a change in the reactive capacity of the bioconcentrator is automatically rectified. A spectral analysis may result in an alarm in the event the bioconcentrator preparation is shown to be improperly manufactured, or to have degraded with storage, or to have become denatured or spent or leached from a surface during use. In addition, a Raman Optrode may be designed to automatically adjust its sampling rate if spectral analyses indicate an altered reactive capacity during the detection of chemical or microbial analytes; automatically perform mathematical manipulations to adjust quantitative analytical results in the event that binding kinetics have been altered, i.e., to account for changes in bioconcentrator reactive capacity due to partial denaturation or partial inhibition or competitive binding or fluctuations in pH; automatically replace a given lot or portion of bioconcentrator in the event the reactive capacity falls below an acceptable minimum; and/or alter the microenvironment surrounding the bioconcentrator, e.g., by adjusting pH or ionic concentration. This aspect of the invention has a major impact on improving the Raman Optrode's false alarm rate and reliability; and also simplifies and improves manufacture, production, and storage procedures.

Similarly, the Raman reactive capacity analysis of any biological material, whether a Raman Optrode bioconcentrator or a biological prepared for another application (e.g., a biological intended for use in other types of biosensors, or use in other types of detection processes involving biological components, or other types of biological preparations intended for other types of applications such as pharmaceuticals and biotechnology products), may be used to monitor the biological during production and/or storage and/or use and to adjust or alter production or storage or use conditions to mitigate any adverse impact. The biological may be a biosynthesized material or an extract, or a dried, purified, lyophilized, crystallized, or immobilized preparation. For example, Raman reactive capacity analysis can be performed automatically on a biological in a completed biosensor device as part of the final "check-out" as the device comes off the production line, and any defective devices rejected; or can be done at one or more points in the manufacturing process, to determine whether the manufacturing process is proceeding satisfactorily, to detect adverse conditions and instigate measures to alter or mitigate them, to detect end points in given steps in the manufacturing process, and to improve overall yield and/or reduce costs. If desired, Raman reactive capacity analysis processes or devices in accordance with this invention may be used to provide input to a process control device to automate and/or optimize the production of biologicals.

The Raman Optrode invention is superior to all of the prior art, whether conventional wet chemistry techniques, prior art Raman spectrometer devices or processes, or prior art biosensors, for a variety of reasons.

In comparison with conventional wet chemistry analyses, for example, the Raman Optrode invention is superior in that it requires far fewer resources (i.e., less training, fewer steps, fewer reagents and chemicals, less equipment, and less time required to complete the analysis) for the detection and identification of trace levels of analytes in gases or liquids. Because the present invention can provide exceptional specificity (contributed by the bioconcentrator binding specificity, the Raman spectral fingerprint, and, if used, Raman techniques that confer additional specificity such as RRS and/or SERS and/or 3-D techniques), little, if any, sample preparation is required for applications that would require extensive sample workup by conventional techniques. When SERS, RRS, SERRS, Raman microprobe or microscopy, stimulated Raman gain, or inverse Raman are utilized, the Raman Optrode invention may offer exceptional sensitivity as well, often far better than that which can be achieved by any of the conventional approaches to detection and analysis.

The Raman Optrode is significantly superior to the use of a conventional Raman spectrometer for the analysis of complex matrices, the analysis of samples which vary widely in composition, or the detection of trace levels of analytes. A conventional Raman spectrometer has no way of collecting or concentrating samples for analysis; it only has a probe or sampling accessory which is brought into contact with the sample, but is incapable of purposely interacting with constituents contained in the sample. At best, a Raman instrument might be coupled with a conventional sampling device such as a solid sorbent to concentrate the constituents in the sample. However, as discussed earlier, such prior art sorbents concentrate many or most of the sample constituents, thereby causing high background noise, reduced sensitivity, and increased false alarm rates. The Raman Optrode invention, however, is superior in that it has a bioconcentrator capable of specifically interacting with the analyte, isolating the analyte (either through physically separating the analyte from the bulk medium, or through the creation of unique signals that "isolate" the analyte from constituents unable to create a similar signal) and, if desired, specifically collecting and concentrating the analyte for much more sensitive and specific and rapid detection and analysis. A device in accordance with the present invention may be designed so that the bioconcentrator is an integral component within a Raman Optrode device; or may be designed so that the bioconcentrator is a separate item or device that is used as a sample collector, said sample collector being designed to be subsequently attached to or inserted into or held against a Raman spectrometer device for later analysis of the samples collected by the bioconcentrator.

While a prior art Raman spectrometer can utilize a roughened metal film to gain signal enhancement, it does not have any way of causing the analyte to adsorb onto or be held in intimate contact with the metal film. At best, a sample containing the analyte may be applied to the metal film, but only the signal from that portion of the analyte which adsorbs onto the metal or is within a few nanometers of the surface will be enhanced. In general, the bulk of the analyte will stay in the bulk medium, where its unenhanced signal will not be detectable. In addition, all other constituents in the sample will be applied to the metal surface at the same time, and their Raman signals will be similarly enhanced; since it is likely that many such constituents will be present in concentrations far in excess of the trace analyte, their signals will be enhanced far in excess of those from the trace analyte, thereby overwhelming the analyte signal. In the Raman Optrode invention, however, the bioconcentrator may be used to collect and concentrate most or all of the analyte from the sample, and it in contact with or in close proximity to the metal surface, thereby gaining considerably more sensitivity from surface-enhancement techniques than conventional approaches relying on nonspecific, reversible adsorption. In the Raman Optrode invention, sample constituents other than the analyte will remain in the bulk sample medium, where their unenhanced signals will not be detectable. Prior art approaches include the use of polymer or crown ether coatings to absorb the analyte and hold it in proximity to the metal surface to gain some improved sensitivity and specificity. The Raman Optrode sampling approach is superior in that it utilizes the binding between biological and analyte, a process much more specific and with much higher affinity for the analyte than polymers or crown ethers exhibit. Further, some degree of nonspecific adsorption and/or absorption is experienced with the synthetic coatings; whereas the bioconcentrator coating of the Raman Optrode interferes with adsorption onto the metal by other sample constituents; and techniques as are known by those versed in the art may be used to prevent or minimize adsorption onto the bioconcentrator.

While a prior art Raman spectrometer device may utilize RRS techniques, only lasers that generate resonance within the analyte may be selected to improve sensitivity and/or specificity. Often, a sample will contain other constituents that are chemically similar to the analyte; a laser that induces resonance in the analyte can be expected to induce resonance or pre-resonance in these related species. Generating stronger signals from these other species increases the background, and decreases sensitivity and increases the false alarm rate. Since other sample constituents are often present in greater concentrations than a trace analyte, the resonant or pre-resonant signals from these more concentrated constituents can be expected to overwhelm the resonant signal from the analyte. The present invention is superior in that it may utilize resonance induced in the bioconcentrator and/or bioconcentrator-analyte complex, as well as or instead of resonance induced in the analyte itself. If the bioconcentrator is chemically very different from species contained the sample (as would often be the case, e.g., in environmental samples, industrial process samples, workplace air samples, etc.), a wavelength that induces resonance in the bioconcentrator and/or its complexes is not likely to induce resonance or pre-resonance in the other sample constituents. Further, if 3-D techniques are used in the present invention, the Raman Optrode may induce resonance in both the analyte and the bioconcenlrator and/or bioconcentrator-analyte complex; there is no corollary approach that can be used with conventional Raman approaches. In addition, the Raman Optrode is superior in that it can be designed to monitor changes in the spectrum of the bioconcentrator which are only caused by binding at the bioconcentrator's active site; this attribute provides exceptional confidence that the unknown to which the Raman Optrode is responding is indeed the analyte of interest, and not an interferant.

The Raman Optrode is superior to prior art using vibrational spectroscopy for the identification of microorganisms for many different reasons. First, neither the German FTIR prototype microbe analyzer nor any other efforts to develop methods for identifying microorganisms have conceived any integrated mechanism for collecting, purifying and processing a sample. All prior art relies on cumbersome and time-consuming procedures such as plating and culturing isolated colonies, and then transferring these isolated, "purified" colonies to a spectrometer for analysis. The Raman Optrode is superior in that it uses a bioconcentrator to, in essence, collect and concentrate the target microorganisms from complicated samples, thereby enabling the ready analysis of complicated samples without any plating and culturing. Second, because prior art approaches do not provide any mechanism for specifically collecting and concentrating target organisms, all microorganisms in a given sample must be analyzed—once they have been plated and cultured—in order to detect the presence of the target analyte. The Raman Optrode, on the other hand, isolates only those microorganisms that are capable of binding with the bioconcentrator and, hence, only those microorganisms that are capable of binding with the bioconcentrator need be analyzed. Third, because the prior art does not provide any way of specifically isolating any given type of microorganism, the spectrum of any microorganism that is presented to the vibrational spectrometer—whether IR or Raman—myst be compared against the reference spectra of virtually all microorganisms that might be present in a given sample. In the case of very complicated or highly variable samples—such as environmental samples or clinical specimens—the number of different microorganisms that might be present are well into the hundreds of thousands. The effort required to develop such a database is exorbitant, while the algorithms required to sort through the reference database for comparison of the "unknown" sample would be extremely complicated. It is difficult to believe that a suitable algorithm can be developed that will identify "unknowns" with high reliability. The Raman Optrode is highly superior in that it provides a mechanism for specifically isolating only a small handful of microorganisms even from the most complicated and variable of samples, e.g., through the use of capture antibodies. Accordingly, the reference spectrum database for the Raman Optrode need only comprise the spectra of those microorganisms capable of being captured by the bioconcentrator; and the Raman Optrode can be developed much more easily, and its algorithms can be much more simple, accordingly. Fourth, because the prior art relies on the plating and culturing of microorganisms and the exhaustive comparison of the resulting spectra of thousands of "unknowns" against hundreds of thousands of reference spectra, the analysis of a single complex sample can take many days or weeks of work. The Raman Optrode is superior in that, with the "built-in" sampling/collection/concentration/purification effect of the bioconcentrator, analysis of even a highly complex sample can be accomplished very quickly and easily. Fifth, to conduct an analysis, prior art methods require sufficient biomass of the target analyte, concentrated at a single point within the spectrometer, to generate a signal. The only way to achieve that requirement is through plating and culturing. This not only requires additonal time, effort, chemicals, and equipment; it means that certain types of microorganisms that are not readily cultured, especially many viruses, cannot be detected or identified. Without exhaustive manual purification/sorting steps, other analytes such as pollens cannot be identified. Still other types of analytes, such as spores, can only be identified by inducing the germination of the spores, followed by culturing. The Raman Optrode is superior in that it can use the bioconcentrator to collect and concentrate the requisite biomass; and so can be used in the detection and identification of recalcitrant analytes such as viruses, and in the direct detection and identification of other analytes such as pollens and spores without manual sorting or forced germination.

The Raman Optrode is superior to the German FTIR invention in that it provides several additional approaches to enhance the sensitivity, specificity, and reliability of microbial detection and identification. Some bacterial constituents do not provide much taxonomically-significant information, while the presence and concentration of other constituents can vary widely. Because IR provides a combined spectral fingerprint of overlapping contributions from all sample constituents—microbial or otherwise—the contributions from individual bacterial components cannot be resolved, and variable constituents can therefore cause spectral variability and complicate the analysis. The Raman Optrode is superior in that it can exploit RRS, 3-D spectroscopy, and/or SERS, individually or collectively, to eliminate spectral background 'nonsense' from unimportant cell constituents, resolve overlapping contributions from different taxonomically important markers, and significantly enhance sensitivity. RRS enables selective probing of individual biological macromolecules in membranes, cells, and tissues, thereby enhancing specificity and sensitivity in the Raman Optrode. There is no corollary technique that can be used in a system such as the German FRIR microbe analyzer. The Raman Optrode can also be designed to use more than one laser wavelength to produce more than one 2-dimensional spectrum from each organism. For example, one laser wavelength can be used to generate an NRS spectrum, providing an overall "composite" fingerprint from the analyte; a second can be used to induce resonance in nucleic acids; and a third subsequently used to induce resonance in protein residues. Hence, the Raman Optrode can be designed to selectively probe key taxonomic markers, effectively 'resolving' some of the overlapping spectral information and thereby providing additional layers of specificity that are not available in an IR-based approach. Further, the Raman Optrode is superior in that it can utilize the SERS phenomenon to enhance sensitivity and specificity, and reduce spectral variability as well. As discussed above, some bacterial cell constituents such as RNA and dipicolinate vary widely in relative content during different points in the growth cycle or due to different environmental conditions. Such variability is observed primarily in the spectral Contributions from the cytoplasm constituents rather than those from the cell wall or membrane. The Raman Optrode is superior in that it can utilize SERS to selectively enhance signals from cell surface structures, thereby eliminating a major source of spectral variability. There is no corollary technique that can be used with the German invention. In addition, no prior art that utilizes Raman analysis has ever involved the use of SERS for identification of microorganisms. And, finally, the Raman Optrode is superior to the German FTIR invention in that Raman Optrode analysis is completely compatible with water, and so can be used for direct detection of solvated/suspended species, as well as dried organisms.

The Raman Optrode is superior to prior art in the biosensor field in that the Raman Optrode invention offers a transducer which is specific, i.e., the Raman Optrode monitors signals characteristic of and unique to the analyte, whereas the prior art monitors a nonspecific signal that has no direct correlation to the chemistry or structure of the analyte, e.g., a signal produced by a secondary chemical or reagent. Further, conventional biosensor techniques monitor the increase or decrease in a single signal for triggering an alarm. Not only can the Raman transducer of the present invention monitor a signal which comes directly from or is directly influenced by the chemistry of the analyte itself, but it can monitor many such signals, i.e., a process or device in accordance with the invention may compare a plurality of bands from the "unknown" against a plurality of reference or "known" bands, and require that each and every one of the "unknown" bands corresponds both in wavelength and relative intensity to the reference bands before an alarm or positive response is triggered. This means that a Raman Optrode has substantially superior specificity and a much lower false alarm rate than biosensors belonging to the prior art.

In addition, the Raman Optrode invention is superior in that it is capable of identifying the analyte which is present, not just detecting its presence as conventional biosensors do; and can even confirm that the analyte has bound at the active site of the biological component, which none of the prior art can do. This means that the Raman Optrode invention can use a single bioconcentrator to detect and identify and quantify a plurality of analytes; other biosensor technologies must utilize a different biological component for every analyte in order to identify and quantify a plurality of analytes. Further, the Raman Optrode can use a single transducer in combination with one or more bioconcentrators to detect and identify and quantify a plurality of analytes; prior art biosensors require a separate transducer for each analyte to produce quantitative information for a plurality of analytes. In addition, the ability to actually identify the analyte results in superior specificity and more confidence in the transducer response. Because no reagents or labeled analogs are needed for transduction, the Raman Optrode biosensor detection process can be much more simple and rapid; and the process can be less susceptible to fluctuations due to changes in temperature. In addition, because no reagents are required for a signal to be generated, there is no need for water; the Raman Optrode process can therefore be used to sample vapors directly from the air.

The Raman Optrode is also superior to all prior art biosensors in that it is possible to calibrate the Raman Optrode using one or more of a variety of internal calibration procedures; none of the prior art provides such a capability. This is a highly advantageous attribute, in that it allows the Raman Optrode to be designed for truly independent operation while providing accurate and precise quantitative information; and can be used to greatly simplify the design and operation of detection and monitoring devices, and of systems or processes for the rapid and reliable analysis of multiple discrete samples.

The only prior art in the biosensor field that can claim a "specific" transducer is a process documented in U.S. Pat. No. 4,411,989, Oct. 25, 1983, "Processes and Devices for Detection of Substances such as Enzyme Inhibitors", A. Grow. That process utilizes enzymes to capture one or more enzyme inhibitors (i.e., the analytes), coupled with an IR spectrometer as the transducer. Unlike the rest of the prior biosensor transducer art, the IR transducer does not measure enzyme activity or monitor the presence of reaction products or substrates. Instead, the transducer monitors the IR absorption spectrum of the enzyme itself, and "looks for" changes in the spectrum or in individual spectral bands which are directly associated with the enzyme-inhibitor complex, i.e., specifically caused by binding with the analyte itself. The patent notes that while the IR/enzyme invention is not bound by any theory, it is believed that the changes observed in the absorption of the IR light are due to the formation of a third substance, distinct from both the enzyme and the analyte, which has its own identifiable characteristics that are reflected in a distinctive IR absorption spectrum. The inventor believed that unique spectra could be produced for each enzyme-analyte complex because an inhibitor is capable of forming one or more permanent covalent bonds with the enzyme moiety, which might thereby substantially change the chemistry of the entire enzyme molecule. While the IR/enzyme process invention offers a number of advantages over the previous biosensor prior art, in that the transducer is specific and binding is required between the enzyme and the analyte for the enzyme spectrum to change, the invention is severely limited in its abilities and applications. Most importantly, many compounds will not inhibit any of the known enzymes; therefore, the IR/enzyme process cannot be used to detect the majority of chemical analytes. No microorganisms inhibit enzymes; therefore, the IR/enzyme process cannot be used to detect microorganisms. In addition, because the IR transducer generates information on all of the asymmetrical bonds in the enzyme, the IR spectrum produced from the enzyme-analyte complex is extremely complicated, with many overlapping bands which cannot be resolved instrumentally or mathematically; there is no way to probe selected moieties or bonds within the enzyme-inhibitor complex. Hence, it may be difficult to find an enzyme whose enzyme-analyte and enzyme-interferent spectra differ sufficiently to yield the specificity necessary for many applications. Further, due to the limited sensitivity of the IR absorption transducer, the IR/enzyme process may not have the level of sensitivity desired for many trace analyte detection applications. Because water interferes with the IR spectrum over broad wavelength ranges, its usefulness for analyzing aqueous samples is severely limited, and the IR/enzyme invention's intended primary application is the direct detection of airborne vapors. Finally, because IR spectroscopy is based on light absorption, the IR light must be introduced to the enzyme-inhibitor complex in such a way that the IR does not pass through any strongly absorbing materials between emission and detection, other than the enzyme-inhibitor complex. Very few materials are transparent to IR radiation; hence, very few can be used in designing a system for bringing the IR light into contact with the sample. In general, any material to be analyzed by IR spectroscopy is finely ground, mixed with potassium bromide, and pressed into a thin film through which the IR light is shone. Alternatively, a handful of different salts are transparent in some windows of the IR spectrum, and may be used as MIR plates, i.e., in the analysis of materials coated on the plates. The suitable salt crystals, however, are very brittle and easily broken, and therefore cannot be used in, for example, fiber optics. Further, many of the suitable salts are easily dissolved in water; materials to be analyzed must therefore be applied to the MIR plates in a nonpolar organic solvent and then dried. Hence, the configurations that are possible for any biosensor based on the IR/enzyme process are extremely limited.

The Raman Optrode invention is highly superior to the IR/enzyme invention. The underlying phenomena on which IR and Raman spectroscopy are based are significantly different, as are the procedures and instrumentation used to acquire the two types of spectral information. Hence, the Raman Optrode is fundamentally different in the types of information it can yield, the types of analyses which can be performed, and the ways in which it can be configured and used. For example, the Raman Optrode invention is not dependent upon covalent binding between the biological and the analyte, although such binding certainly may take place; instead, the Raman Optrode exploits a variety of intramolecular as well as intermolecular interactions that may occur when a biological and its ligand interact, including major changes to the biological's peptide backbone, sulfide bonds, hydrogen bonds, amino acid residue microenvironment, etc., which are far removed from the active site or the ligand, and which cannot be detected by IR spectroscopy. Hence, while the IR/enzyme invention is limited to the use of enzymes in the detection of enzyme inhibitors, the Raman Optrode can utilize virtually any type of biological as the bioconcentrator in the detection of virtually any analyte, including both chemicals and microorganisms, and even dead microorganisms and/or fragments or subcellular components of microorganisms, if desired, in addition to living cells. The Raman Optrode is also superior in that it can readily be used in monitoring or analyzing aqueous samples, since water does not interfere with Raman spectroscopy the way it does with IR spectroscopy. More importantly, because of the basic underlying differences between the two types of spectroscopy, the Raman Optrode invention can exploit a number of different techniques to simplify and clarify and enhance the resulting spectrum, probing individual bonds and functional groups and thereby providing exceptional specificity. For example, the Raman Optrode can utilize surface-enhancement, resonance, surface-enhanced resonance, and three-dimensional spectroscopy; there are no comparable techniques available for use in the IR/enzyme biosensor. Further, due to the availability of surface enhancement and resonance, the Raman Optrode can be considerably more sensitive than the IR/enzyme technology, often by several orders of magnitude. The Raman Optrode is further superior to the IR/enzyme biosensor in that the Raman Optrode can utilize Fiber optics components for configurations involving, for example, remote sampling or sampling arrays; a wide range of fiber optics capable of transmitting Raman signals over long distances (i.e., kilometers and even tens of kilometers) are available. Similarly, a wide range of rugged, inexpensive, water-insoluble optical waveguide materials are available for use with Raman. In addition, because the Raman Optrode is based on a light scattering phenomenon, rather than a light absorption phenomenon, Raman Optrode sampling can involve querying bioconcentrator surfaces directly, and even remotely; and so the Raman Optrode can be designed in many configurations which would be difficult or impossible to use in an IR/enzyme biosensor.

The Raman Optrode is superior to all of the prior art in the biosensor field, including the IR/enzyme invention, in that the Raman Optrode offers a means for monitoring the status of the delicate biological component, i.e., the bioconcentrator, and ensuring that there are no false alarms or failures to alarm due to any partial or complete denaturation, inhibition, loss, or destruction of the biological component. None of the prior art biosensor inventions have this ability. Further, the Raman Optrode is unique in its ability to detect changes in the reactive capacity of the bioconcentrator (e.g., due to changes in pH or temperature the presence or absence of solvents or co-factors or proteases), which allows the Raman Optrode to take these factors into account whenever accurate or precise quantitative measurements are needed. No other biosensor technology is capable of automatically adjusting the calculations made during quantitative analyses to account for changes in biological activity—or, indeed, to even detect that there are changes in the biological activity of the biological component due to factors other than the presence of the target analyte.

Raman Optrode technology is also more reliable than all other types of biosensors or related assays in that each and every bioconcentrator prepared for and/or used in the Raman Optrode can be nondestructively checked during production as well as during use to ensure that the bioconcentrator preparation is fully active, that any immobilization has been performed successfully, that no unwanted contaminants or by-products are present, and that no significant degradation or contamination has occurred during storage, as well as ensuring that the sample environment has not had any adverse effect on the perfonnance of the bioconcentrator. Other types of biosensor biological components are forced to rely on batch sampling and destructive testing to evaluate the success of the manufacturing process and/or any degradation due to storage, and cannot be monitored during use.

The present invention is superior to all of the prior art in the biosensor field in that the Raman Optrode may be used far more effectively with both antibody regeneration and reversibility techniques. When regeneration techniques are used, the Raman Optrode can be designed to monitor the status of the antibody, and to adjust the results of the quantitative analyte analysis accordingly, thereby eliminating any variability due to variations in the amount of antibody that is denatured in each regeneration cycle; and also thereby determining when the antibody preparation is degraded to the point that it must be replaced. Biosensors based on the priority are unable to do either; hence, their results are variable due to the variable amount of antibody degradation experienced in each regeneration cycle; and the antibody preparation must be discarded at a point long before its capacity is fully degraded in order to ensure that none of the cycles utilize an antibody that is too degraded.

Because Raman analysis can differentiate among crossreactive moieties, the Raman Optrode can also be coupled very effectively with reversibility techniques. The Raman Optrode is superior over the prior art when coupled with bioaffinity techniques, in that other bioaffinity sensors require the additional costs and complexity associated with producing a labeled high-weight analog. The Raman Optrode is already capable of distinguishing between the analyte and a high-weight analog, through the differences in their spectra, and does not require a specific label to be attached. Similarly, an RCRU-based Raman Optrode would not require the additional complexity and cost of developing and using the protocols to label the linked analog, since the Raman Optrode is already capable of determining whether the linked analog or the analyte itself is bound to the bioconcentrator, through the Raman spectral information. Even if the analyte itself is used as the analog, attaching the link to the analyte changes its chemistry and, hence, its Raman spectrum.

The Raman Optrode is superior to other techniques for the detection and identification of microorganisms in that it does not require any cell growth or pre-enrichment or culturing; and analyses can be completed within seconds rather than the several hours to several days required by prior art techniques. Further, the Raman Optrode can detect dead cells or parts of cells, as well as living cells, yet can differentiate between the living and nonliving analytes, which no prior art technique is capable of doing.

The present invention is also superior to prior art in the field of evaluating biologicals such as biotechnology products, in that Raman Optrode analysis determines the reactive capacity of the biologicals rather than measuring biological activity. Raman Optrode determination of reactive capacity is nondestructive; hence, unlike procedures or techniques for measuring biological activity, Raman Optrode reactive capacity analyses may be performned on an entire lot or batch of biological instead of on individual samples or aliquots. In addition, Raman Optrode reactive capacity analysis may be performed on a "real-time" basis, continuously during the processing of a biological; whereas prior art techniques for measuring biological activity are time-consuming and laborious, and the results will not be available for hours or even days. Further, Raman Optrode reactive capacity analysis does not require any additional reagents, as do prior art techniques for measuring biological activity. Finally, and perhaps most importantly, Raman Optrode reactive capacity analysis is superior in that it can provide information on the reason(s) for a change in (potential) biological activity, e.g., the mode by which denaturation occurred, changes in the oxidation state of a given biological, spin states of haems, and/or aggregation states, loss of co-factors, changes in the peptide backbone, etc., or some combination thereof, thereby enabling corrective measures to be taken; whereas the prior art for measuring (actual) biological activity simply determines that a change has taken place, but cannot provide any information as to the cause or reason.

The Raman Optrode is also superior to all conventional detection and/or monitoring and/or analysis technologies, including prior art biosensor technologies, in that a wide range of sampling configurations are possible with the present invention, making it possible to design Raman Optrode processes or devices for a much wider range of applications than are normally possible for processes or devices based on the prior art, especially other biosensor processes or devices, and to use sampling approaches that have significant advantages over conventional sampling approaches. For example, the Raman Optrode can utilize a sampling configuration similar in appearance to conventional solid sorbent sampling systems such as the quartz fiber bundle. In a preferred embodiment, for example, the Raman Optrode sampling system may consist of a long, fiber optic waveguide, "cladded" only with the SERS-active metal film and the bioconcentrator, and then bundled or coiled. This configuration of the present invention provides a high surface area and low pressure drop, such as those achieved by the quartz fiber bundle, for optimum high-volume sampling. The Raman Optrode sampling system is superior to the quartz fiber bundle, however, in that the Raman Optrode invention collects and concentrates the analyte molecules by a specific binding mechanism (i.e., interaction with the bioconcentrator), thereby minimizing the concentration of unwanted potential interferents; the quartz fiber bundle, on the other hand, utilizes a nonspecific adsorption mechanism, and concentrates many or most sample constituents as well as the analyte. In the Raman Optrode fiber optic, light from the laser can travel through the fiber via the evanescent wave of multiple internal reflectance (MIR) and interact with the bioconcentrator-analyte complexes on the fiber optic surface. Sensitivity is greatly enhanced, since the light interacts with the bioconcentrator-analyte complex dozens or even hundreds of times through MIR or the evanescent wave, enhancing the signal further with every interaction; there is no corollary for the quartz fiber optic. In the Raman Optrode, there is no need to flush the concentrated analyte off the fiber or transport it to the detector as there is with the quartz fiber bundle; instead, the analyte is analyzed in its bound form. Hence, there is no loss of the analyte after collection in the Raman Optrode as is experienced during desorption/flushing steps mandatory for the quartz fiber bundle. Furthermore, analysis can be continuous in the Raman Optrode fiber optic coil, whereas only batch sampling/analysis is possible in the quartz bundle. And, since the Raman spectrum can be used to monitor the bioconcentrator in the Raman Optrode, it is possible to directly and continuously determine whether the Raman Optrode sampling system is fully reactive and capable of binding its analyte(s); whereas poisoning or degraded adsorptive capabilities cannot be determined in a conventional quartz fiber bundle sampling system without with the use of external analyte standards for calibration.

As another example of the wide range of sampling configurations that are possible with the present invention, a dipstick is coated with an array of "spots", each spot containing a bioconcentrator immobilized on a roughened metal film. This dipstick is mmersed in a liquid sample, or used to swab a surface, thereby permitting a multitude of analytes within the sample or upon the surface to complex with the bioconcentrators on the lipstick. The dipstick is subsequently inserted into a read-out system comprising an imaging Raman spectrometer. The imaging Raman spectrometer is capable of simultaneously collecting individual spectra from each of the bioconcentrators in the array on the dipstick. The Raman Optrode dipstick thereby permits the simultaneous collection and analysis of individual spectra associated with each individual constituent present in the sample, each individual spectrum free of the interferences of spectra contributions from other sample constituents, thereby resulting in the simultaneous, specific detection and identification and quantification of a multitude of analytes within a single sample. Conventional Raman spectroscopy, on the other hand, would permit only the collection of a single, extremely complicated spectrum comprised of the overlapping spectra of all sample spectra, no matter what configuration of spectrometer was used. Further, each of the metal films underlying the various bioconcentrators in the present invention can be individually tailored, both in metal composition and roughness features, to adjust the signal enhancement due to SERS phenomena selectively and specifically and individually for the bioconcentrator that is immobilized thereon. This enables the present invention to exhibit a wide range of sensitivities and specificities for various analytes during a single sampling and analysis event. Conventional approaches to SERS analysis, on the other hand, comprise the use of a single metal-coated surface, so that the enhancement of the signal from one sample constituent is influenced by precisely the same metal surface with precisely the same characteristics as the enhancement of the signal from another sample constituent.

There are a multitude of other configurations possible with the present invention.

It will be further apparent from the following detailed description of the present invention, which is intended to be illustrative thereof rather than taken in a limniting sense, that a much improved process and apparatus are provided which offers a exceptional versatility and improved performance over the prior art methods and devices.

BRIEF DESCRIPTION OF THE DRAWINGS

FIGS. 4a–4c are diagrammatic illustrations, partly in section and partly in elevation, of a portable sampling system useable in accordance with this invention;

FIGS. 6a–6d are diagrammatic illustrations, partly in section and partly in elevation, of a bioconcentrator "badge" or "dipstick" sampling unit and its Raman read-out system which may be used in accordance with this invention;

DETAILED DESCRIPTION OF THE PREFERRED EMBODIMENTS

Figure 1:
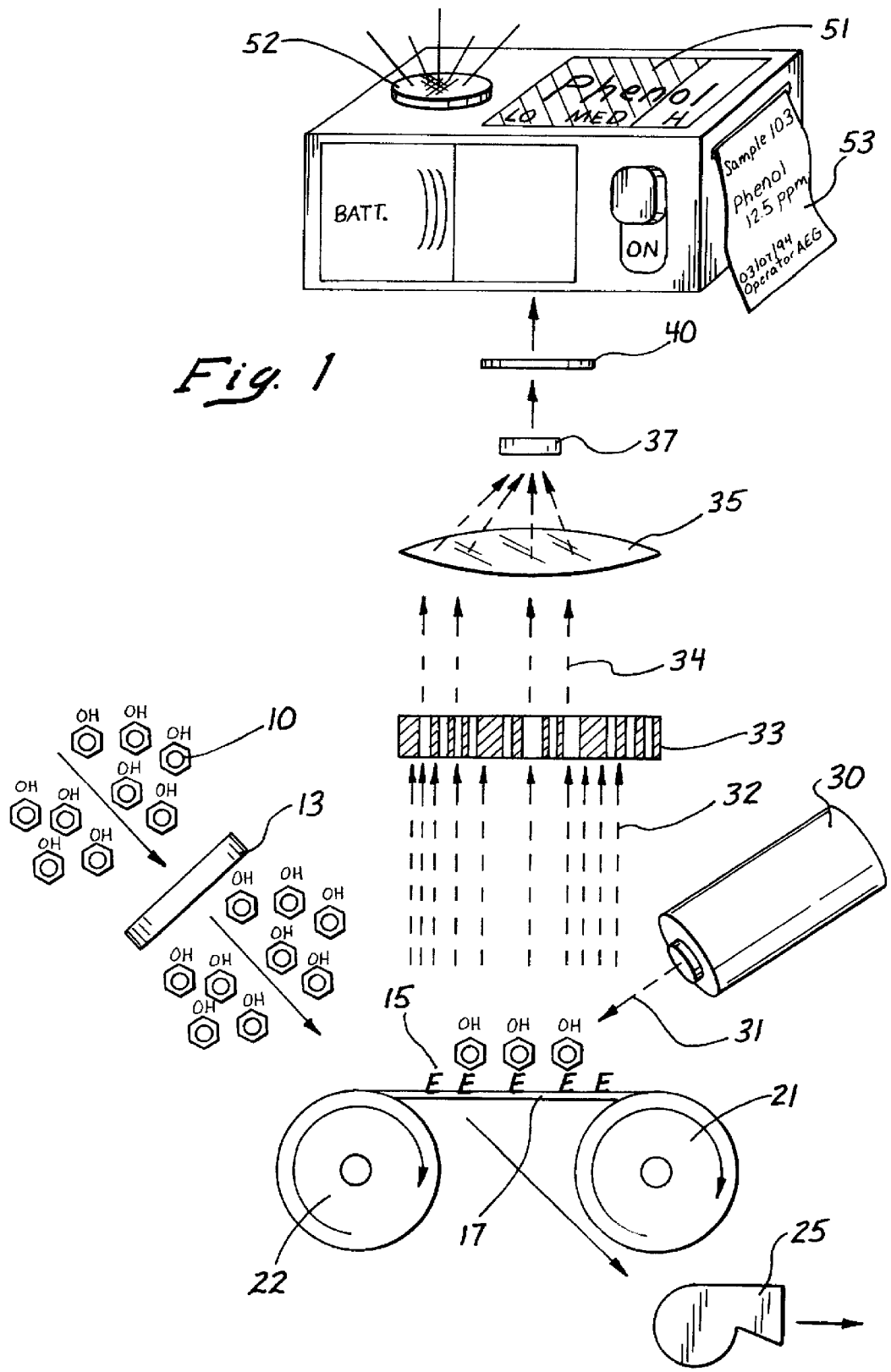
FIG. 1 is a diagrammatical illustration of one form of device in accordance with this invention.

In general, the present invention is a direct analysis procedure and device involving four steps. The first step involves bringing a sample into contact with a bioconcentrator in such a way that if any analyte is present in the sample, at least some of the analyte binds with the bioconcentrator, thereby forming a bioconcentrator-analyte complex. In the second step, the bioconcentrator and/or bioconcentrator-analyte complex are exposed to irradiating light, such as one or more laser wavelengths, suitable for generating a Raman scattering spectrum. Third, Raman spectroscopic techniques are then used to collect and process the spectral bands and focus them on a detector suitable for transforming the light signal into electronic signals. In the fourth and final step, the electronic signals are compared against one or more baseline spectra to determine the presence and/or identity, and, if desired, the quantity, of the analyte. In addition, if desired, the comparison may also produce information about the bioconcentrator itself, i.e., whether the bioconcentrator is fully reactive or has become degraded to the point that analyte analyses must be modified or the bioconcentrator must be replaced, said information then being used to adjust or modify the procedures used in the detection and analysis of the analyte. A baseline spectrum may be generated at the same time as analyte detection, simply by taking a Raman spectrum of the bioconcentrator immediately prior to bringing the sample into contact with the bioconcentrator. Alternatively, if more information is desired, the baseline may be a library of model reference Raman spectra, generated in advance from the bioconcentrator in reactive and nonreactive or partially reactive forms, and from "known" bioconcentrator-analyte complexes, and then stored in the Raman Optrode's memory for the purposes of such a comparison.

The apparatus, in accordance with this invention, generally includes a bioconcentrator; a method or mechanism or device for bringing the sample into contact with the bioconcentrator; a light source such as a laser suitable for generating Raman scattering from the bioconcentrator and/or the bioconcentrator-analyte complex and/or the amalyte; a Raman spectrometer suitable for processing the optical information, translating it into an electrical signal; and a signal analysis apparatus or procedure or mechanism suitable for storing the library of model reference spectra and for comparing and analyzing the "unknown" sample spectrum produced by the Raman spectrometer in such a way as to detect and/or identify and/or quantify the complexed analyte(s), and/or evaluate the status of the bioconcentrator itself.

The invention may also include a method or mechanism or device for generating an alarm, display, printout, signal to a computer or controller, or other form of announcing or presenting or transmitting or responding to the results of the Raman analysis. Ancillary components or subsystems may also be included as desired or necessary, such as devices or components for monitoring and/or adjusting temperature, pH, humidity, internal pressure (e.g., indicative of a clogged filter), etc.; batteries or other sources of electrical power; a keypad or other mechanism for entering data; a carrying case or housing; a mechanism or device for adding or measuring or monitoring internal standards for calibration procedures; and the like.

Turning now to the Drawings, reference is made to FIG. 1 which illustrates a preferred form of the present invention, for purposes of explanation. This form, for purposes of illustration, involves detection of phenol and/or substituted phenols in water, but it is to be understood that the invention is not limited to those analytes, nor to dissolved or suspended or hydrated analytes, nor to the configuration shown.

Thus, water containing the analyte(s), here phenol and substituted phenol molecules, is drawn through the invention by a mechanism such as a liquid a pump 25, passing preferably first through a filter 13 which removes suspended particulates such as dirt, pollen, and debris from the water, and then over or through or past a flexible tape 17, before being exhausted. The flexible tape 17, preferably porous and coated with a thin, rough film of silver, is supported on take-up and supply reels 21 and 22. A bioconcentrator 15, preferably in the form of the enzyme NADPH oxidoreductase, is immobilized in the silver film on the tape. As the liquid containing the analyte comes into contact with the tape, dissolved phenol molecules in the water bind to the enzyme on the tape, thereby causing at least some of the dissolved phenols to be collected and concentrated on the tape's bioconcentrator.

A suitable excitation source such as a laser 30 is positioned to project radiation 31 of a one or more predetermined wavelengths, here 568 nm, onto the bioconcentrator. As the laser radiation impinges on the bioconcentrator 15, a Raman scattering spectrum 32, unique to the enzyme-analyte complex, is produced. The unique emitted spectral radiation passes through an optical spectrometer subsystem, which may comprise, for example, a Hadamard transform liquid crystal spatial light modulator generally indicated at 33 that produces an encoded signal 34; optics generally indicated at 35 which collect and focus the encoded Raman signal; and a detector, generally indicated at 37. The detector 37 converts the encoded light signals into an electrical signal, the latter fed to a software processor 40 which compares the emitted radiation to a library of model reference spectra (as will be shown) to determine whether the emitted radiation conforms to that of a given enzyme-phenol complex, identifies the phenol that would cause such a spectrum to be generated, and optionally determines the amount thereof. Connected to the output of the processor 40 is a display subsystem which may be in the form of an alarm 52, and/or a display screen 51 indicating the identity of the particular phenol and the relative amount thereof. Optionally, a hard copy print-out 53 of the results may be provided, as illustrated. The entire assembly may be housed in a suitable package as will be apparent to those skilled in the art.

While the invention is in operation, the bioconcentrator is exposed to the light from the laser 30 on a continuous, semi-continuous, or periodic basis. The analyses performed by the software processor 40 determine not only whether the emitted spectral radiation conforms to that of an enzyme-phenol complex, but also whether the emitted spectral radiation conforms to that of a fully active bioconcentrator. If the emitted spectral radiation analysis determines that the bioconcentrator has been degraded, denatured, deactivated, digested, bound to another inhibitor material, or otherwise rendered incapable or less capable of binding phenols, then the tape 17 is advanced so that a fresh supply of bioconcentrator 15 is exposed to the water stream during subsequent analysis intervals.

If quantfification is desired as well as detection, an internal standard 67, shown here as $SO_4^{-2}$ coinunobilized with the bioconcentrator on the tape, may be used. During the Raman analyses, the internal standard 67 is irradiated at the same time and by the same light source as the bioconcentrator is irradiated, and the Raman scattering spectral band from the internal standard 67 is produced and collected and processed at the same time and by the same instrumentation as the Raman scattering spectral bands from the bioconcentrator-analyte complexes are produced and collected and processed (as will be shown). The ratio of the intensities of the 981 $cm^{-1}$ line from internal standard and a key line from an analyte's spectrum, in comparison with ratios of these lines in model reference spectra, may be used to quantify the amount of pollutant which has been captured by the application of quantitative spectral analysis methodologies as are known to those versed in the art.

Figure 2:
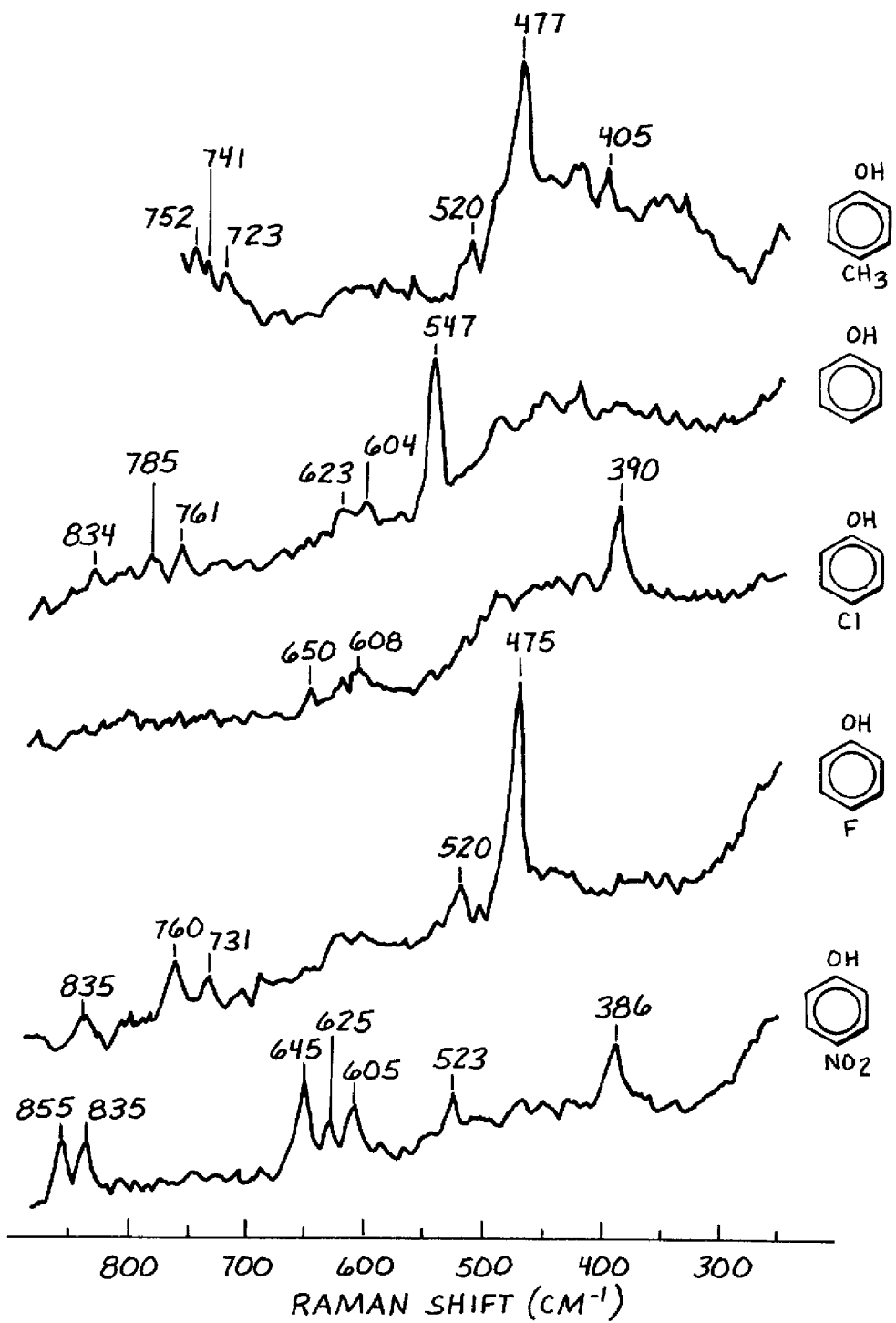
FIG. 2 is a reproduction of resonance Raman scattering (RRS) spectral information that may be used in the detection and identification of substituted phenols captured by an enzyme bioconcentrator.

Because the Raman spectrum of each enzyme-inhibitor, enzyme-substrate, or enzyme-co-enzyme complex is unique, a Raman Optrode can identify a plurality of analytes even when a single enzyme is used to capture the plurality of analytes and a single optical spectrometer subsystem is used to collect and process the resulting spectral information. For example, FIG. 2 illustrates model reference spectra that might be included in the library of a Raman Optrode designed for the detection and identification of phenol and substituted phenols, when the enzyme NADPH oxidoreductase is used as the bioconcentrator and a laser operating at 568 nm. As may readily be seen from these resonance Raman scattering spectra, the identity of an "unknown" phenol captured by the enzyme may be determined by comparison of the unique spectrum that is generated when said enzyme-"unknown" inhibitor complex is irradiated by a laser operating at 568 nm with the "known" NADPH oxidoreductase-phenol complex spectra in the library.

While the tape is described as being coated with an enzyme specific to substituted phenols, it may be coated with enzymes specific to other materials, even non-pollutant materials, instead. While the tape is described as being coated with an enzyme that will collect and concentrate a plurality of analytes; it certainly may be coated with an enzyme that will collect and concentrate a single analyte. The tape may also be coated with other types of bioconcentrator molecules, e.g., antibodies or hemeproteins, or a mixture thereof, or even nonprotein bioconcentrators, for the detection of a plurality of analytes varying more widely in chemistry and configuration than closely related analytes such as the substituted phenols. Because of the specificity of the bioconcentrator and the unique bands of the Raman spectrum associated with each antibody-antigen, antibody-hapten, enzyme-inhibitor, enzyme-substrate, enzyme-co-enzyme, or other protein-ligand complex, one or a plurality of analytes may be detected and identified and quantified at one time.

Figure 3A:
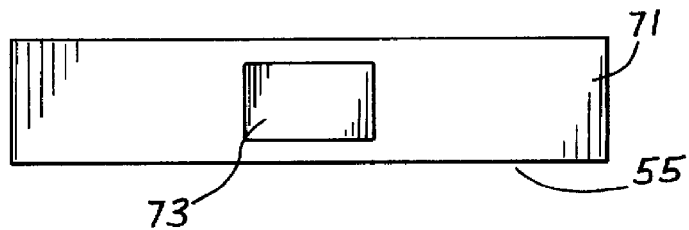
FIGS. 3a–3e are diagrammatic illustrations, partly in section and partly in elevation, of a removable cassette unit usable in accordance with this invention.
Figure 3B:
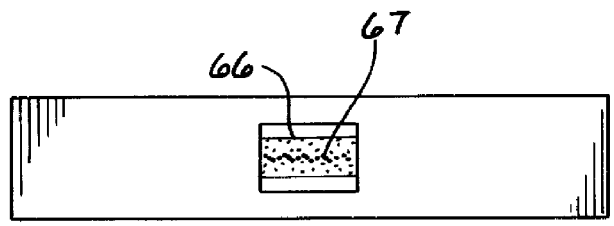

FIGS. 3a to 3e illustrate a removable cassette module 55 which may be used in accordance with this invention as a sampling subsystem within a detector device such as that illustrated in FIG. 1, or within other Raman Optrode devices or configurations, as will be shown. FIG. 3a illustrates the inlet side, FIG. 3e the exhaust side, and FIGS. 3b–3d cross sections of the removable cassette. The cassette 55 is mounted in a modular housing 56. In the cassette are a tape supply spool 62 and a take up spool 64, as shown. The cassette 55 includes a sample window 68 permitting exposure of a tape section 66 to the liquid, and an exhaust chamber 69 through which the liquid is drawn by the pump. The inlet side 71 of each cassette, as shown in FIG. 3a, includes a filter element 73 to remove particulate matter such as dirt, pollen and suspended debris. The removable cassette module is sealed into the Raman Optrode housing by an O-ring seal 76 and includes a location slot 78 for proper orientation of the cassette within the Raman Optrode housing.

Figure 3C:
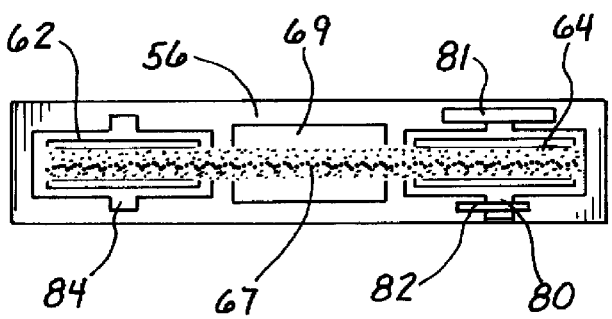
Figure 3D:
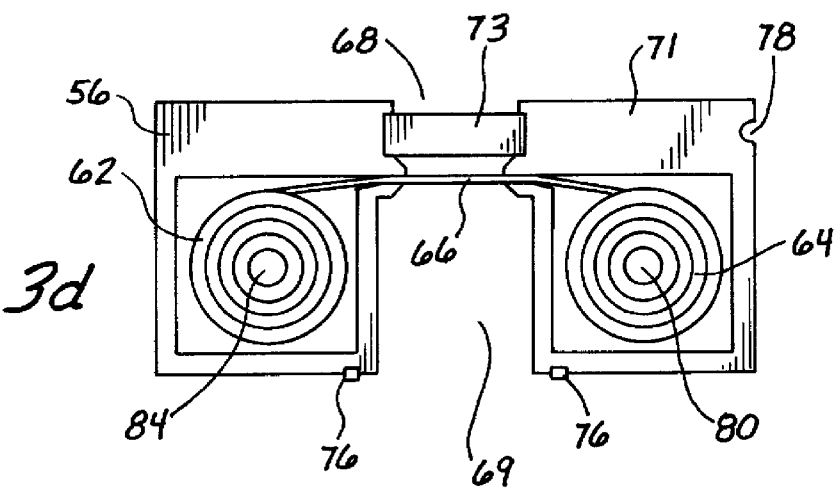
Figure 3E:
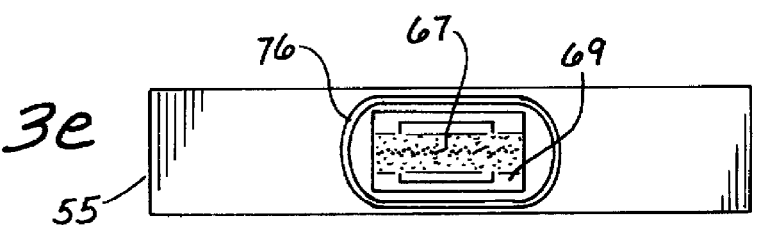

As shown in FIGS. 3c and 3d, the take up spool is mounted on a support rod 80, the latter including a spring biasing means 81 tending to wind up the take up reels. The other end of the rod 80 includes a rotation impeder 82 which fits in a notch of the rod. When the impeder is released, the spring causes the rod to rotate a predetermined amount to bring a fresh section of each tape under the window 68. As shown the tape supply spool is also supported by a support rod 84.

In operation, when the Raman spectral analysis indicates the presence of an analyte, visual and audible alarms are triggered, and the tape is advanced by a signal to the rotational mpeder 82 so that a fresh section of unexposed bioconcentrator is moved into the sampling window 68 for the next sampling cycle. Similarly, when the Raman analysis indicates that the bioconcentrator is denatured or degraded or saturated with analyte, the tape may be advanced so that a fresh section of tape bearing fully active bioconcentrator is exposed in the window. When all sections of the tape have been exposed and all bioconcentrator used or spent, then the operator may remove the disposable cassette and replace it with a new cassette.

While a single tape coated with one strip of immobilized bioconcentrator is shown, it is apparent that multiple strips or arrays of spots of immobilized bioconcentrators may be used on a single tape, and may be exposed to diffuse irradiation such that all strips or spots are exposed to the same irradiating wavelength at the same time and all resulting Raman bands are collected and processed at the same time, e.g., through the using of imaging Raman spectroscopy. It is also apparent that a tape containing a plurality of strips or spots of bioconcentrators may be scanned by a scanning Raman spectrometer instead; and that multiple tapes may be used and scanned, as desired, and may either be advanced at the same time using the same advancement mechanism, or at different times using different advancement mechanisms. While a separate and distinct strip or spot bearing a reference chemical, i.e., an internal standard, is shown incorporated into the tape, for use in quantitative analysis/calibration, it is also apparent that multiple strips or spots bearing multiple reference chemicals may be used instead; or that the internal standard may be mixed with the bioconcentrator; and that different reference chemicals may be used with different bioconcentrators, either mixed and co-immobilized with the bioconcentrators or immobilized on one or more separate strips or spots.

A means for encoding the cassette (e.g., a bar code, a pattern of electrical contacts, protruding pins, or the like, not shown) that corresponds to the bioconcentrator(s) immobilized on the tape therein [and, accordingly, corresponds to the analyte(s) that may be detected thereby] may be incorporated in the cassette, and the Raman Optrocle electronics and software designed such that the Raman Optrode can "read" the code, and automatically adjust or modify or tailor the Raman analyses that are performed when the cassette is inside the Raman Optrode housing, and alter the display or printout accordingly. For example, when "Code A" is on the cassette, it may indicate that NADPH oxidoreductase is immobilized on the tape, and that all measured spectra should be compared against model reference spectra of that enzyme and its phenol complexes. Any "positive" matches between measured and model spectra should cause the identity of the corresponding phenol to be shown on the display. However, when "Code B" is on the cassette, it might indicate, for example, that the enzyme cholinesterase is immobilized on the tape, and that all measured spectra should be compared against model reference spectra of that enzyme and its organophosphorus or carbamate complexes; and any "positive" matches between measured and model spectra should cause the identity of the corresponding pesticide or nerve agent to be shown on the display. The Raman Optrode might even be designed to process a code such that the laser is tuned to a different wavelength for irradiating the tape, the pump is operated at a different speed, the intervals over which spectra are collected and co-added are adjusted, the spectrometer is switched into a scanning or a 3-D operating mode, etc., depending on the bioconcentrator(s), their analyte(s), the configuration of the tape (e.g., the number of strips of bioconcentrators immobilized thereon), or even, perhaps, the type of sample to be analyzed (e.g., whether human blood or drinking water is to be analyzed for nerve agents).

A similar cassette may be used when sampling air, by replacing filter 73 with one compatible for filtering particulate matter from gases. Moreover, if desired, a humidifier may be incorporated into the cassette for those devices intended for sampling air in extremely dry environments, in order to ensure optimum binding kinetics. The humidifier (not shown) may be as simple as a water reservoir and a wick in contact with and leading from the water reservoir preferably to the filter 73, or to the section of tape in the sampling window.

As mentioned, the Raman Optrode sampling system or subsystem may take any of several forms. It is possible, in accordance with this invention, to immobilize the bioconcentrator on a surface that is not physically attached to or enclosed within the same device or housing as the light source, optics, detector, and/or electronics. Sampling (i.e., bringing some portion of the matrix to be analyzed into contact with the bioconcentrator in such a fashion that at least some portion of the analyte becomes bound to the bioconcentrator), may take place or be performed separately and independently from Raman read-out (i.e., the irradiation of the bioconcentrator-analyte complex, the spectroscopic analysis of the resulting Raman bands, and the translation into an identification of the captured analyte), using separate processes and/or devices for the sampling and the Raman read-out steps.

For example, at least one sample may be collected using a separate sampling process or device, at a location far removed from the site at which the Raman read-out equipment or device is kept; and the collected sample(s) may be labeled or encoded and stored for some period of time before being analyzed. FIGS. 4a to 4c illustrate a handheld sampling system 155 for collecting discrete samples of air. In a preferred form of the invention, this handheld sampling device is used in conjunction with the removable cassette 55 shown in FIG. 3, and a separate Raman read-out device (not shown). FIG. 4a illustrates a cross section, FIG. 4b the top view, and FIG. 4c the side view, of the handheld sampling system. The sampling system 155 comprises a housing 121 with a sampling window 127, a fan 131 and motor 133, and a gas passage 128 permitting flow of gas to the tape section 68 and out an exhaust port 129 as drawn by the fan. The sampling system also contains a cavity 135 with space and connectors 132 for power supply batteries 141; a means 142 such as a thermistor for measuring ambient temperature; electronics 143 for controlling the fan and the tape rotation impeder that advances the tape in the cassette; and means such as a slide switch 122 for turning the sampling system on and a push button 123 for starting each sampling cycle. The sampling system also contains a cavity 136 which holds the removable cassette 55. The removable cassette module is guided into position in cavity 136 by location guide 108 in the cavity and location slot 78 in the cassette, and sealed into the sampling system housing by O-ring seals 106 in the cassette cavity and 76 in the cassette. Doors 125 and 126 conceal and protect the contents of battery cavity 135 and cassette cavity 136, respectively.

Not shown is a means on the cassette for encoding the cassette, which indicates the types of bioconcentrators immobilized on the tape, i.e., the types of analytes which may be sampled and collected by and bound to the bioconcentrators. As shown in FIG. 4b, the sampling system has a display 151 that indicates the analytes which may be sampled by the cassette as indicated by the code; not shown is a means within the sampling system for reading the code and modifying display 151 accordingly. The sampling system may also have a display 152 that indicates the ambient temperature as measured by thermistor 142 and/or gives an indication that the power remaining in the batteries 141 is below a minimum level.

In operation, the operator inserts the cassette into the cassette cavity and then turns the sampling system on by moving the slide switch 122 to the "on" position. The operator then uses a means such as push button 161 to set the appropriate volume of sample to be collected. This push button 161 may affect, for example, the period of time during which a sample is to be collected (as shown), the speed at which the fan is to operate, or both. The period of time selected by the operator may be shown in display 153, and if incorrect or to be changed, may be reset using means 162. Once the sampling volume is set, the operator is ready to collect samples. Samples may be collected by positioning the sampling system such that sampling window 127 is in proximity to the air source to be sampled, and pushing the "sample" push button 123. When the "sample" push button 123 is pressed, the sampling system automatically starts the fan (thereby pulling air through the sampling window and tape, and bringing the analyte in contact with the bioconcentrator on the tape), and, after the fan has run for the time period set by the operator, turns the fan off again, and then advances the tape so that a fresh section of tape 68 bearing unbound bioconcentrator is exposed to sample entering the sampling window 127.

It is apparent that, if desired, a humidifier may be incorporated in either the cassette itself or the sampling system, for those applications in which the device is used in extremely dry environments. It is also apparent that the handheld sampling system may be readily designed to collect liquid samples instead of air samples, by replacing the fan/motor with a liquid pump and by designing the cassette such that the sections of tape that are not in the sampling window are protected from contact with the water (e.g., water cannot "wick" into neighboring sections of the tape or seep into the compartments in the cassette housing and protecting the tape spools.) In addition, it is apparent that a flexible probe may be added to the sampling system for directing or pulling air or liquid from the sample source to the sampling window.

Once all of the samples have been collected, the operator returns to the location at which the Raman "read-out" system (not shown) is located. The Raman read-out system comprises a light source, an optical spectrometer, and electronics and software for controlling the movement of the tape, analyzing Raman spectral information from each section of the tape, and providing a display or printout of the results of the analyses; and also comprises a tape cassette analysis accessory designed to hold the tape cassette in the correct alignment for tape sections in the sampling window 127 to be analyzed individually and sequentially. In a preferred form of the invention, said tape cassette analysis accessory may be similar in design to sampling accessories available for use with modern Raman analytical laboratory instruments for analysis of powders, crystals, liquids, submicroliter volumes of liquids, solids, flexible materials, fabrics, and gases. These sampling accessories usually employ kinematic mounting pins to allow rapid accessory interchange, with reproducible positioning of the accessory in the sample compartment to minimize or totally eliminate the need for aligning the optics. In a preferred form of the invention, then, the Raman read-out device is a commercial Raman laboratory instrument, and the tape cassette analysis accessory is similar in design to commercial Raman spectrophotometer sampling accessories. In addition, in accordance with the invention, a special software package may be used to control the analysis of the samples on the tape, determine the presence and identity of each pollutant, calculate the concentration of each pollutant, and advance the tape from sample to sample as each analysis is completed. The software may also cause a printout of the analyses to be generated and/or provide a display showing the identity and quantity of pollutants in each sample on the spectrometer's display screen.

In operation, once all the samples have been collected and the handheld sampling device returned to the laboratory housing the Raman spectrophotometer, the operator removes the tape cassette 55 from the sampling system 155, inserts the cassette into the Raman read-out accessory described herein, and programs the Raman spectrophotometer to automatically analyze each section of the tape and provide the type of information from each analysis that he prefers. If the cassette is encoded to indicate the bioconcentrators that are on the tape (and, therefore, the analytes that may be detected and identified by using said tape), then the Raman spectrophotometer read-out system also has a means for reading the code (which, in a preferred form of the invention, be designed into the Raman spectrophotometer sampling accessory); and the electronics and software are designed such that the Raman analyses are automatically adjusted accordingly (e.g., comparisons are performed against different sets of model reference spectra in the library and quantitative measurements performed against different calibration standards, etc.) and the display or printout changed to reflect the different analyte(s).

Figure 5A:
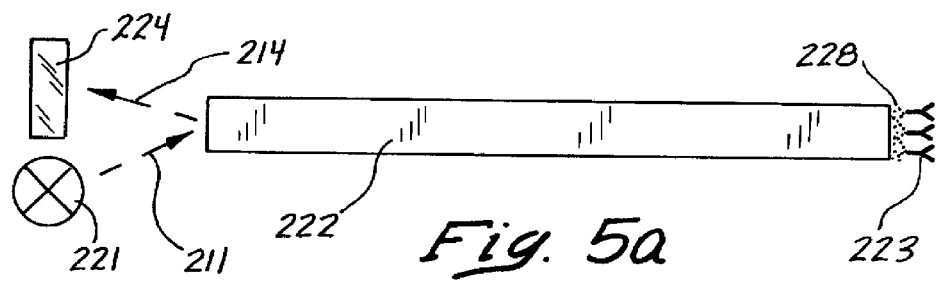
FIGS. 5a–5d illustrate diagrammatically the orientations in which fiber optic components are useable in accordance with this invention.
Figure 5B:
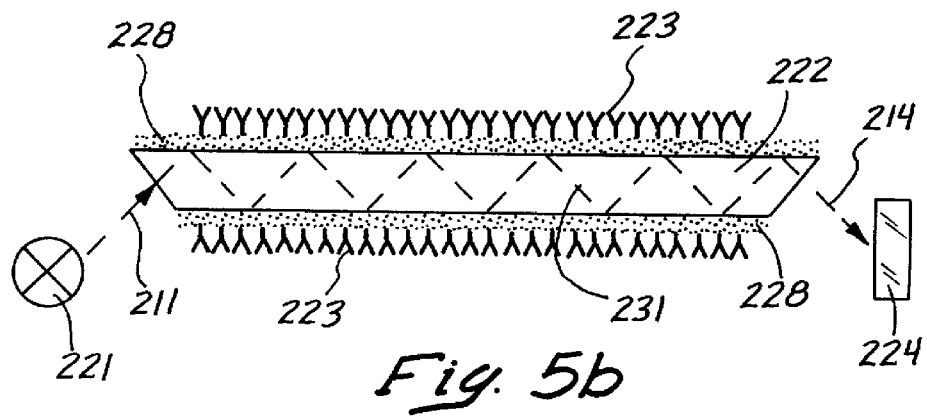

Optical waveguide materials or components may be used in a Raman Optrode, if desired; for example, the bioconcentrator may be immobilized on the surface of suitable waveguide materials, such as a fiber optic waveguide, or optical waveguide crystal or plate, etc. FIGS. 5a to 5d illustrate diagrammatically some of the configurations in which optical waveguide materials may be used in accordance with this invention. As shown in FIG. 5a, the bioconcentrator 223 may be immobilized at or on the tip of a fiber optic waveguide, for example; and the exciting light may travel from the light source 221 through the fiber optic 222 to the bioconcentrator 223, and the resulting Raman spectral information travel through the same fiber optic 222 from the bioconcentrator to the spectrometer 224. Alternatively, the bioconcentrator may be immobilized along part or most or all of the fiber optic or optical waveguide plate or crystal, as shown in FIG. 5b; and the exciting light may travel from the light source 221 through the waveguide material 222 as an evanescent wave 231 and interact with the bioconcentrator 223 on the waveguide surface(s) one or more times before the spectral information is collected and analyzed by the spectrometer 224. In either approach, a metal film 228 may be coated onto the waveguide surface before the bioconcentrator is immobilized on the metal, such that the exciting light penetrates the metal film before coming into contact with the bioconcentrator. It is apparent that the bioconcentrator may be a single biological component, or a mixture of a plurality of biologicals. If the optical waveguide is in the form of a plate or flat crystal, it is apparent that a plurality of bioconcentrators may be immobilized in strips along the surface of said plate or crystal (or on strips of metal film on the surface of said optical waveguide plate or crystal), and the Raman spectrum from each strip of bioconcentrator(s) may be collected and processed separately and independently.

Figure 5C:
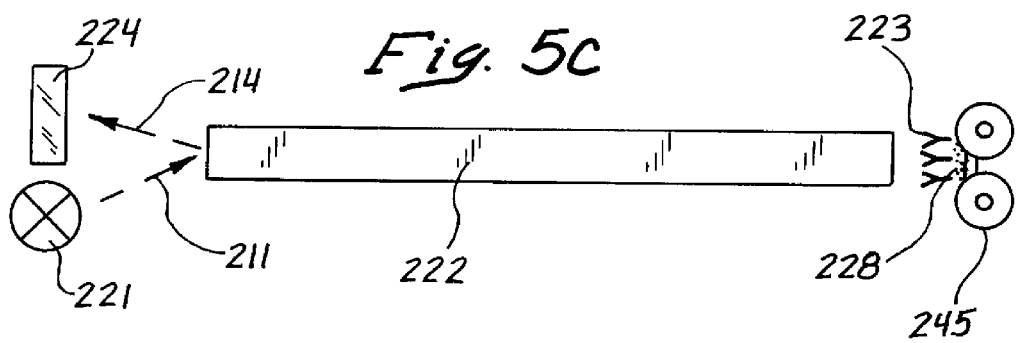
Figure 5D:
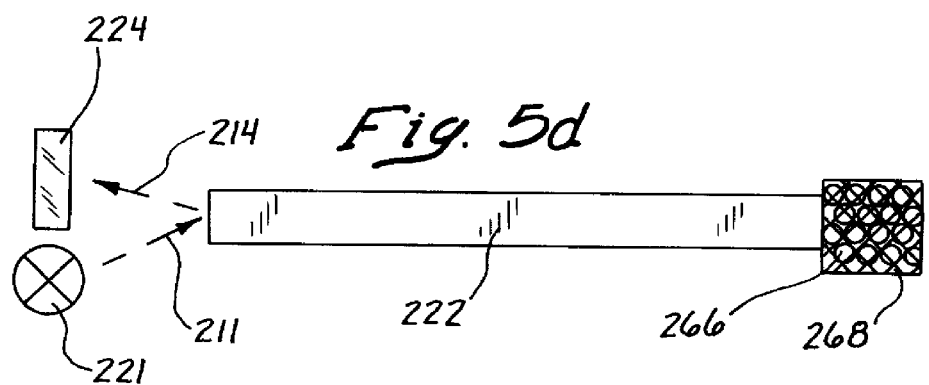

Alternatively, the bioconcentrator may be immobilized on a separate surface, such as an inflexible support surface, and interrogated by a fiber optic probe, as shown in FIG. 5c. It is possible, in accordance with this invention, to use a long flexible fiber optic probe, small in diameter, so as to reach into hard-to-access locations. The probe may, for example, be comprised of a fiber optic waveguide 222, with a small tape cassette 245 at its tip, illustrated diagrammatically in FIG. 5c. The probe is designed so that vapor or liquid samples are brought into contact with the tape. In yet another form, shown in FIG. 5d, the bioconcentrator may be immobilized on some surface other than a tape, for example, small beads 266 held at the tip of the probe by, for example, a wire mesh cage 268. Where a fiber optic waveguide is used, both the exciting light 211 traveling from the light source 221 to the bioconcentrator and the Raman scattered light 214 traveling from the bioconcentrator to the optical spectrometer 224 may travel in opposite directions through the same fiber optic probe, although different fibers may be used, if desired.

The sampling approaches shown in FIGS. 5a to 5d may be used in sampling subsystems within and part of an integrated Raman Optrode detection or monitoring system. Alternatively, the bioconcentrator on its solid support may be a separate sampling device or system, or may be used in a separate sampling device or system, and may be brought into contact with the sample/analyte(s) when separated in both time and space from a Raman read-out device or system.

Figures 6A, 6B, 6C, 6D:
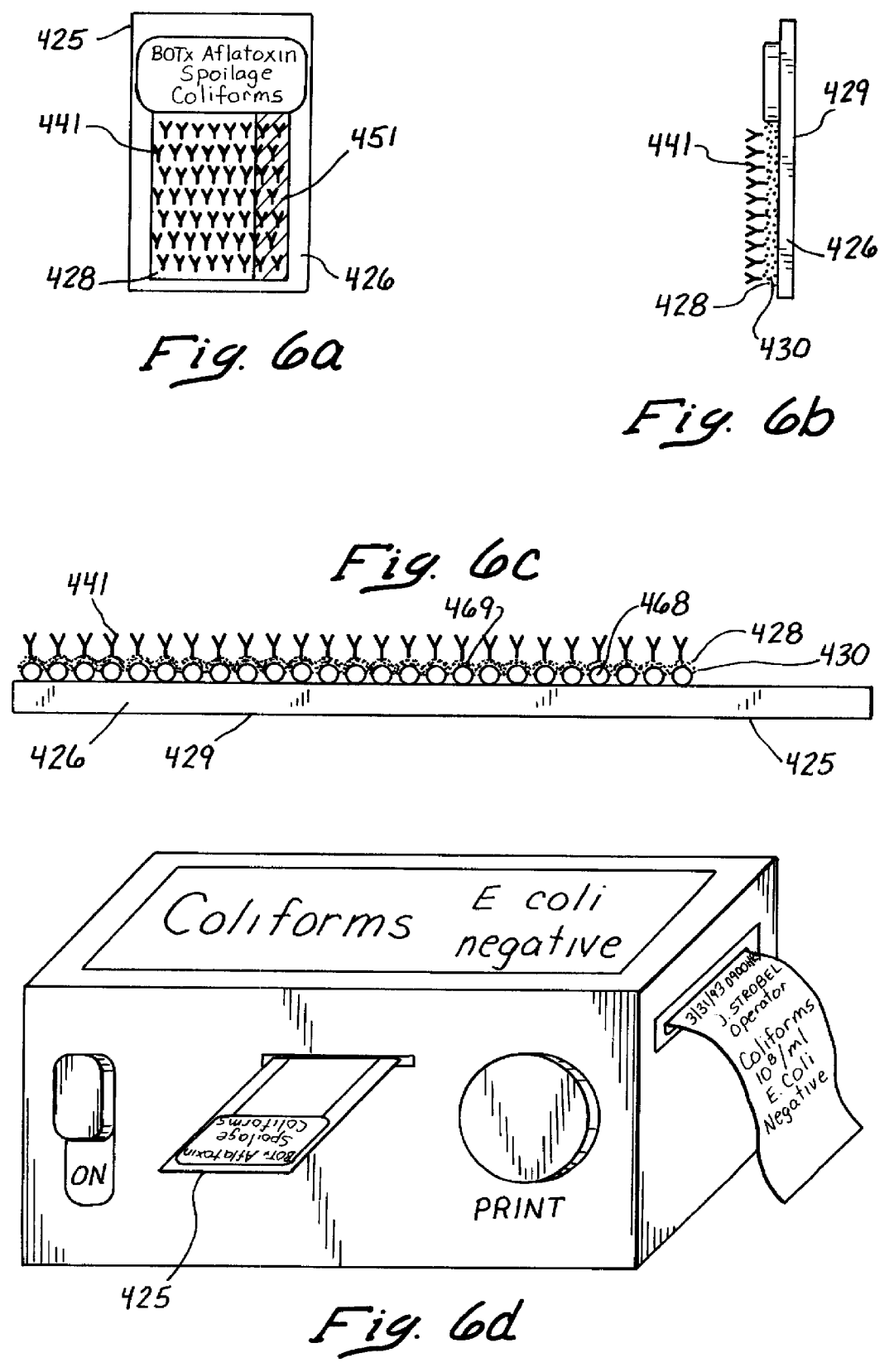

FIGS. 6a and 6b illustrate the top and side views, respectively, of a sampling device that may be used, for example, as a dosimeter badge or a dipstick or a swab or the like. Once the sample has been collected (i.e., the bioconcentrator on the device has been suitably brought into contact with the material to be analyzed), the sampling device may then be inserted into a Raman read-out system, as illustrated generally in FIG. 6d, for analysis of the captured analytes (i.e., irradiation of the bioconcentrator or bioconcentrator-analyte complex, and Raman spectrum collection, processing, and analysis). FIGS. 6a and 6b illustrate a sampling system 425 in the form of a relatively flat supporting member 426, having at least one surface 428 to which a bioconcentrator 441 is immobilized. The bioconcentrator may be any of the materials previously mentioned, or any combination thereof; and may be adsorbed, crosslinked, covalently bound to, or entrapped on the surface of the supporting member. The supporting member may be rigid or flexible and may even be porous, e.g., metallized filter paper; the supporting member may be transparent to the radiation to which it is exposed, e.g., an optical waveguide plate or crystal, thus allowing the radiation to be projected from the underside 429 of the bioconcentrator. A coating 430, such as one or more of the various metals and alloys Ag, Au, Cu, Pt, Li, Na, K, Al, In, W, AgBr, AgCl and $TiO_2$, may be used. A preferred manner in which to provide a roughened surface is illustrated in FIG. 6c in which the sampling system 425 includes a supporting member 426, already described. Here, at least a portion of the surface of the supporting member includes a plurality of microspheres 468. These microspheres may be, for example, polystyrene, polyvinyltoluene, polybutadiene, teflon, aluminum, platinum, or zirconium, having diameters in the range from 100 Å to tens of thousands Å; however, in general, roughness protrusions 5 to 500 nm may be preferred. The beaded surface is then coated with a sputter-deposited metal film 469, preferably silver, copper, or gold. The bioconcentrator may then be affixed to the roughened metal surface as already described. This form of the Raman Optrode sampling system may incorporate use of an optically transparent, impermeable cover 451 to prevent contact with a portion of the bioconcentrator by the analyte, as diagrammatically illustrated in FIG. 6a, for quantitative analysis purposes as previously described. Sampling systems in this configuration may be used, for example, as a dosimeter badge, disposable dipstick, sampling swab, sampling filter, and the like. The immobilized bioconcentrator may be exposed to at least one sample. For example, the badge may be worn for a period of time; the dipstick inserted into or used to stir a liquid or suspension; the swab (with or without a liquid) used to wipe or mop or scrub a surface; a liquid sample drained through the sampling filter; etc. After exposure to the material to be analyzed, the sampling device may, if desired, be labeled or coded and stored for later analysis. Sampling devices in this configuration may then be inserted into a sampling accessory in a Raman read-out system, illustrated diagrammatically in FIG. 6d, for analysis, or may be analyzed using a Raman read-out system with a fiber optic probe scanner (not shown), or the like, as will be apparent to those versed in the art. Such a sampling device would be useful for passive or active dosimetry, field sample analysis, blood or urine analysis, monitoring surfaces for microbial contamination, etc.

Figure 7:
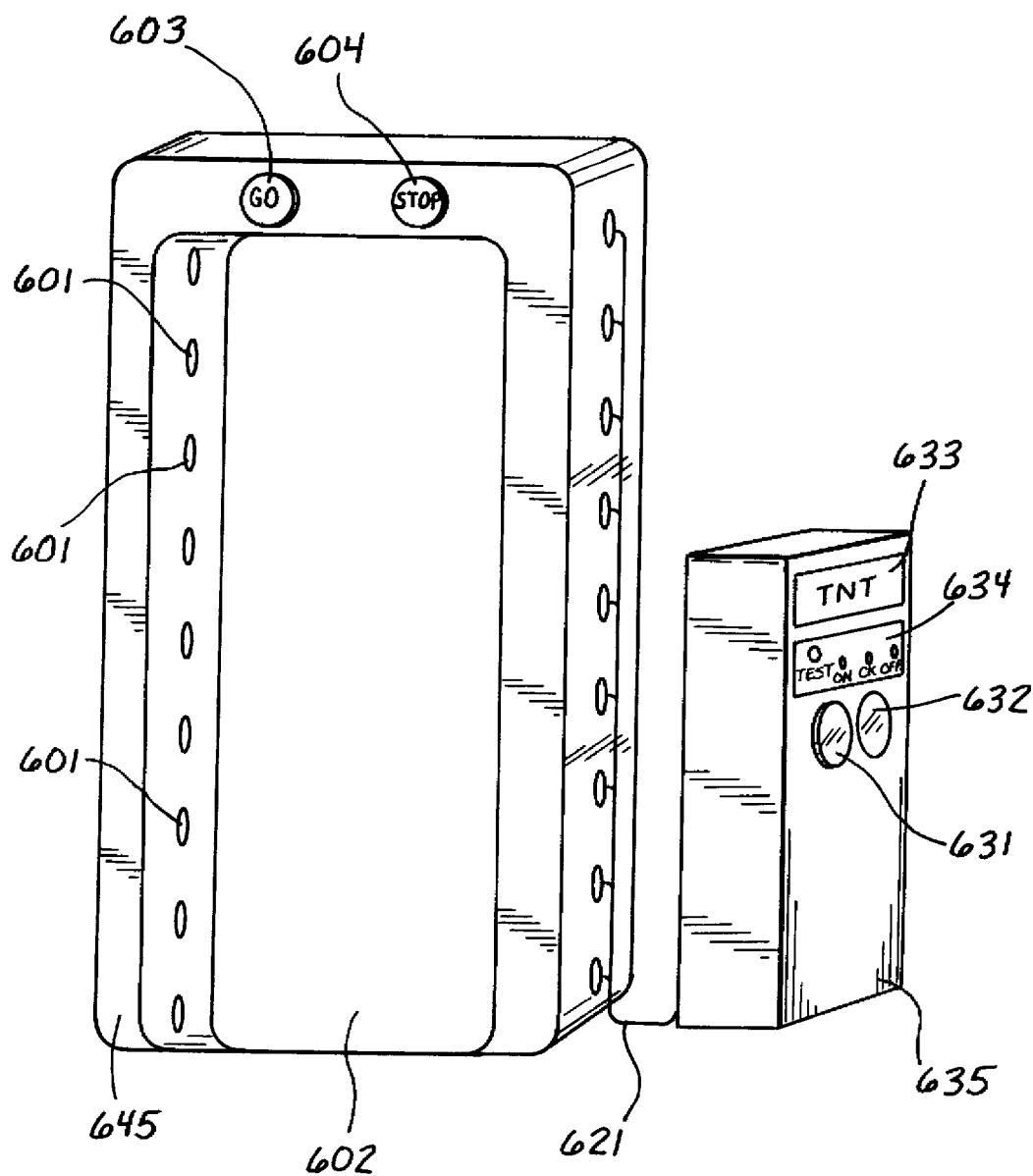
FIG. 7 is a diagrammatic illustration of a fiber optic array Raman Optrode in accordance with this invention.
Figure 8:
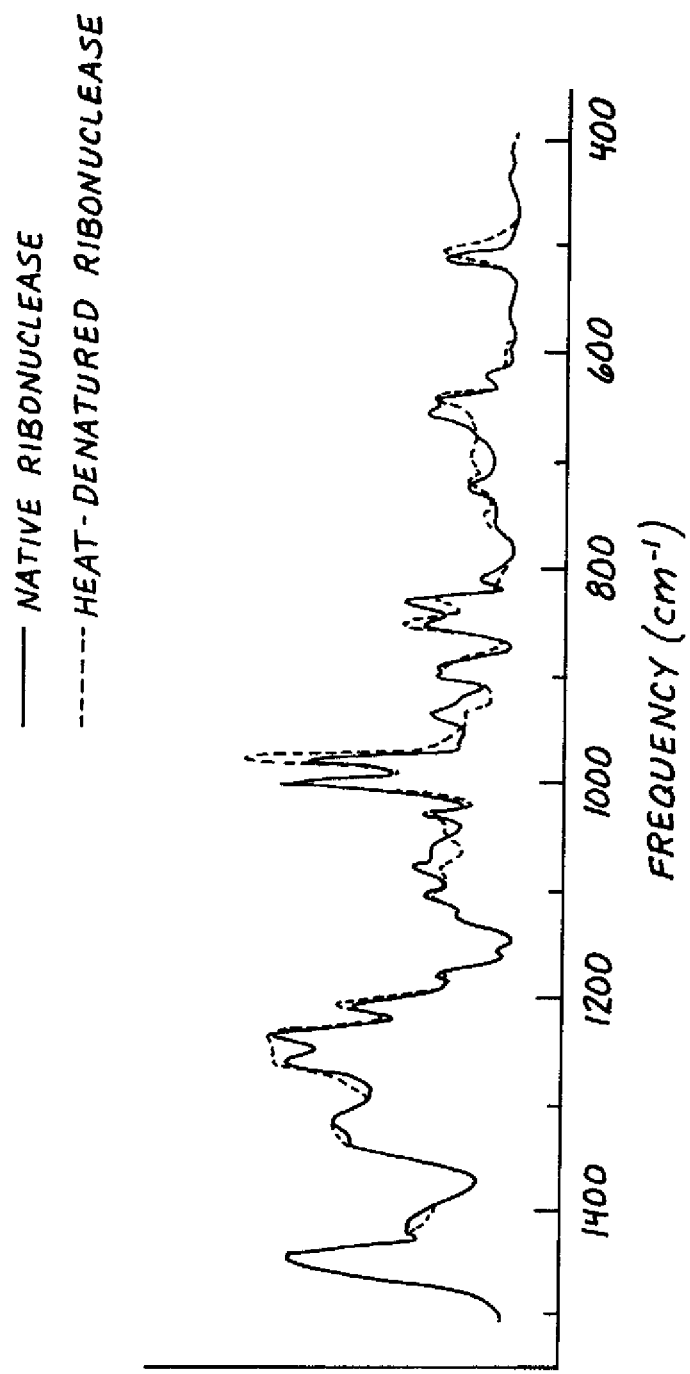
FIG. 8 is a reproduction of normal Raman scattering (NRS) spectral information that may be used in the Raman reactive capacity analysis of ribonuclease to detect enzyme that has become denatured by heat.

A single Raman spectrometer may be used with a plurality of sampling subsystems in accordance with this invention. In one such design, the plurality of sampling subsystems may be connected to the Raman read-out subsystem via a fiber optic cable array. FIG. 7 is a diagrammatic illustration of a configuration that might be used, for example, as a passenger screening portal for the detection of hidden contraband such as illicit drugs or explosive devices. The portal may consist, for example, of a booth 645 and an operator station 635. A plurality of sampling subsystems 601, each containing, for example, a removable tape cassette module, may be located at a series of individual sampling sites around the interior of the portal, as shown. Individual fans may be collocated with each sampling subsystem, such that air from the interior of the booth is pulled into contact with bioconcentrator(s) in each of the tape cassettes. Alternatively, a single fan may be coupled with an air vent array designed such that the single fim pulls an appropriate amount of the booth air through each of the cassettes and into contact with the bioconcentrator(s) contained therein. Each sampling subsystem 601 is connected to the Raman spectrometer, housed within the operator station 635, via a fiber optic cable array 621 that carries the Raman spectral signal from the bioconcentrator(s) in each sampling subsystem in the booth to the Raman spectrometer in the operator station. If desired, a central light source such as one or more lasers may be collocated with the Raman spectrometer in the operator station 635, and the exciting light dispersed and carried through the fiber optic cable array 621 to the individual sampling subsystems 601. Alternatively, a plurality of light sources may be collocated, e.g., one or more lasers each, with the sampling subsystems. Preferably, the Raman spectral signals traveling from the various sampling subsystems to the operator station are combined into a single light signal through the use of suitable optics within the Raman spectrometer subsystem before Raman analysis is performed. Alternatively, the plurality of Raman spectra from the plurality of sampling subsystems may be analyzed individually and sequentially.

In addition to the Raman spectrometer and, possibly, the light source, the operator station 635 may also be equipped with a control panel 634, visual 631 and/or audible 632 alarms, and/or a display 633 showing the presence/identity of any detected contraband; and the sampling booth may be equipped with "stop" and "go" lights 603 and 604. The display 633 may also show internal diagnostic information, as needed.

In operation, the passenger to be screened waits until the "go" light 604 flashes on. He then enters the booth 645 and stands in its interior 602. The operator then pushes the "on" button found in the control panel 634. This causes the "go" light 604 to go off and the "stop" light 603 to go on (thereby signaling to the next passenger in line to wait); causes transparent doors to slide into place over the entrance and exit to the booth; causes the fans located in the plurality of sampling subsystems 601 to be turned on, which pull the air inside the booth through the bioconcentrators in the sampling subsystems; and also causes the Raman spectral signals from the various sampling subsystems to then be analyzed. If the analysis indicates the presence of contraband, the identity of the contraband detected may be shown on the display screen, the visual and/or audible alarms may be sounded, and/or a signal may be sent to a warning system at Security Headquarters, etc. If the Raman analysis indicates that the passenger is not carrying any contraband, the transparent doors are automatically opened, allowing the passenger to leave the booth, and the "stop" light is turned off and the "go" light is turned on again, signalling the next passenger in line to enter the booth.

Finally, FIG. 8 illustrates model reference spectra that might be included in the library of a Raman Optrode designed for reactive capacity analysis for ribonuclease wherein the enzyme might be exposed to heat. As may be readily seen from these NRS spectra, the presence of denaturing heat may be readily detected, i.e., thermally denatured ribonuclease is clearly distinguishable from native ribonuclease when the NRS spectra of the two are compared. The relative intensities of the ratios $I_{832}/I_{852}$ and $I_{1000}/I_{972}$ may also be used in determining the enzyme reactive capacity.

Having described the invention in more detail, the following examples are given to illustrate the broad range of specific applications of the invention, including specific techniques and specific configurations which can be used to perform the invention. These specific examples are not intended to limit the scope of the invention described in this application.

For example, chemical warfare agents such as mustard vesicants can be detected by this invention, using DNA as the bioconcentrator and NRS techniques to monitor two baseline wavebands. Mustard vesicants are known to be capable of alkylating nucleic acids and polynucleotides; and it is also known that the guanine base and its methylated derivative have different and distinctive Raman spectra, with the methylated derivative lacking the strong band at 1488 $cm^{-1}$ seen in the native guanine base. The replacement of C(8)—H with C(8)—D shifts the 1488 band to 1645 $cm^{-1}$; from this it has been concluded that the 1488 $cm^{-1}$ band is the N(7)═C(8) double bond stretch. Thus, it has now been found that a shift of the Raman N(7)═C(8) double bond stretch band can be used to detect analytes capable of alkylating the guanine moiety in polynucleotides and nucleic acids. When DNA is exposed to methylnitrogen mustard, for example, the 1492 $cm^{-1}$ band decreases in intensity and shifts to 1530 $cm^{-1}$; this change may be attributed to methylation of the guanine moieties by the mustard. No changes in the Raman bands of any other bases are observed in DNA exposed to this agent. Therefore, in accordance with this invention, two NRS wavebands can be monitored, i.e., 1492 $cm^{-1}$ and 1530 $cm^{-1}$, to detect the presence of the agent in the sample.

In another example, NRS analysis of a receptor immobilized in a lipid membrane can be used to detect and identify agonists and antagonists. Alkali-treated subsynaptic membrane fragments from the *Torpedo marmorata* electric organ are rich in native functional acetylcholine receptor (AcChR), which can be used to detect and identify agonists such as carbamylcholine and antagonists such as (+)-tubocurarine. An argon laser tuned at 514.5 nm can be used to irradiate the receptor membrane preparation, and a Raman spectrometer used to scan the 400 to 1800 $cm^{-1}$ region. The presence of carbamylcholine in a sample to which the receptor preparation has been exposed can be detected when the relative intensity of the doublet $I_{879}/I_{1443}$ decreases; the relative intensity of the doublet $I_{702}/I_{710}$ increases and the peaks shift from 702/710 to 700/718; the doublet at 939/961 shifts to 942/967; the peak at 1084 $cm^{-1}$ increases in intensity and shifts to 1086 $cm^{-1}$; and there is no change in the triplet at 510/525/540. The presence of (+)-tubocurarine in the sample can be detected when the relative intensity of the doublet $I_{879}/I_{1443}$ increases; the relative intensity of the doublet $I_{702}/I_{710}$ increases and the peaks shift to 700/719; the doublet at 939/961 shifts to 935/957; the peak 1084 $cm^{-1}$ shifts to 1088 $cm^{-1}$ and becomes more intense; and the triplet at 510/525/540 broadens and shifts to 520/551/565.

In another example, microprobe Raman (in this case, confocal Raman microspectrometry) can be used to identify different types of leukocytes, e.g., different types of granulocytes. It is well known that many granules, containing highly specific enzymes, are present inside the granulocyte cytoplasm, and that the enzymatic content of the different types of granulocytes is unique to each type. Therefore, the Raman spectrum of the portion of the granulocyte cell containing the granule has now been found to be unique to the type of granulocyte. In this particular example of a Raman Optrode, the leukocytes are captured by a synthetic peptide bioconcentrator immobilized on a silica surface. However, antibodies specific against leukocytes could be used instead, and are a preferred bioconcentrator for this application. To detect and identify different types of leukocytes such as neutrophilic and eosinophilic granulocytes, a sample of human peripheral blood is applied to the immobilized synthetic peptide bioconcentrator and then rinsed. Spectra from the nuclei of the various types of granulocytes may be essentially identical; in order to ensure that the spectra are being taken from the cytoplasm rather than the nucleus, the line at 1094 cm$^{-1}$ can be used as an indicator of DNA, i.e., if the spectrum shows a strong line at 1094, the focus of the microprobe is moved. However, the spectra from the cytoplasm are strikingly different throughout the spectral window 600 to 1700 cm$^{-1}$. The captured neutrophilic granulocytes can be identified by a small doublet at 645/673 with the peak at 645 cm$^{-1}$ being the stronger; a moderately intense peak at 757 cm$^{-1}$ and a moderately strong doublet at 828/854; a doublet at 982/1004, with the 104 cm$^{-1}$ peak much more intense than the 982 cm$^{-1}$ peak; a moderately intense peak at 1108 cm$^{-1}$; a doublet at 1129/1208, a triplet at 1307/1332/1361, a singlet at 1502 cm$^{-1}$; a triplet at 1542/1590/1614 with 1590 cm$^{-1}$ being broad and 1614 cm$^{-1}$ being a small shoulder; and a moderate peak at 1667 cm$^{-1}$. The captured eosinophilic granulocytes can be distinguished from the neutrophilic granulocytes and identified by a small peak at 622 cm$^{-1}$; a small doublet at 645/675 with the peak at 645 cm$^{-1}$ being less intense; a very intense peak at 758 cm$^{-1}$; a weak triplet at 837/854/880; a relatively intense doublet at 982/1004 with the peak at 982 cm$^{-1}$ being only slightly less intense than the peak at 1004 cm$^{-1}$; a small peak at 1078 cm$^{-1}$; a moderate peak at 1119 cm$^{-1}$; an intense peak at 1212 cm$^{-1}$; a doublet at 1307/1340; a moderate peak at 1520 cm$^{-1}$; a very intense doublet at 1547/1614; and a small peak at 1662 cm$^{-1}$.

NRS is known to provide very complicated spectra of proteins, due to all the bonds and functional groups in the molecule or complex. However, RRS can enhance the signals from chromophoric bands to the point that they are the only features of the spectrum; the RRS spectrum is therefore much more simple with fewer bands. Vibrational modes directly associated with the chromophore have their intensities enhanced significantly, by factors as high as $10^6$. The spectrum resulting from RRS is thus much simpler and high selectivity can be obtained as well as greatly improved sensitivity. For many applications, therefore, RRS may be a preferred technique for use in a Raman Optrode process or device.

For example, RRS may be used with an enzyme bioconcentrator to detect and identify and quantify environmental pollutants such as halogenated phenols. As discussed previously, the enzyme NADPH oxidoreductase may be used as the bioconcentrator for detection of phenol and para-substituted phenols such as p-methylphenol, p-chlorophenol, p-fluorophenol, and p-nitrophenol, as shown in FIG. 2. The enzyme-analyte complexes may be irradiated with a laser operating at 568 nm, and the RRS spectrum collected and analyzed in the window 350–1050 cm$^{-1}$. Contributions to the RRS spectrum will be almost entirely due to the presence of pollutants binding to the enzyme. The presence of phenol can be determined, for example, by the formation of RRS peaks at 547, 604, 623, 761, 785, and 834 cm$^{-1}$; p-methylphenol by peaks at 405, 477, 520, 723, 7411, and 752 cm$^{-1}$; p-chlorophenol by peaks at 390, 608, and 650 cm$^{-1}$; p-fluorophenol by peaks at 475, 520, 731, 760, and 835 cm$^{-1}$; and p-nitrophenol by peaks at 386, 523, 605, 625, 645, 835, and 855 cm$^{-1}$. If quantification is desired as well as detection, a coimmobilized internal standard of $SO_4^{-2}$ may be used, and the ratios of the intensities of the internal standard line to the key lines in the analytes' spectra may be used to quantify the amounts of the pollutants which has been captured. The key peaks which may be used to quantify the pollutants are the 981 cm$^{-1}$ line from the internal standard; 547 cm$^{-1}$ from phenol; 477 cm$^{-1}$ from p-methylphenol; 390 cm$^{-1}$ from p-chlorophenol; 475 cm$^{-1}$ from p-fluorophenol; and 645 cm$^{-1}$ from p-nitrophenol.

In another example, an enzyme can be detected by RRS analysis, using a ligand as the bioconcentrator. In this example, a laser operating at 441.6 nm is used. Irradiation at this wavelength will not excite resonance in most proteins; because only normal Raman scattering would be observed from the protein itself under these conditions, a relatively high concentration of an analyte such as the enzyme carbonic anhydrase might normally be required for a Raman spectrum to be generated. However, the presence of very low quantities of the enzyme carbonic anhydrase can be detected in accordance with this invention if a chromophoric ligand bioconcentrator (i.e., an inhibitor in which resonance can be generated by a laser operating at this wavelength) is used as the bioconcentrator. Carbonic anhydrase is known to be inhibited by a number of sulphonamide derivatives; and a laser operating at 441.6 nm will induce resonance in sulphonamides. The presence of carbonic anhydrase may therefore be determined by monitoring for specific changes in the RRS spectrum of a sulphonamide bioconcentrator. For example, binding of the enzyme to the bioconcentrator 4-sulphonamido-4'-hydroxyazobenzene can be detected by a shift of the 4-sulphonarmido-4'-hydroxyazobenzene line at 925 to 922 cm$^{-1}$; the appearance of a band at 1123 cm$^{-1}$; and an increase in the relative intensities $I_{1413}/I_{1388}$ and $I_{1134}/I_{1138}$. The changes are attributed to an alteration in the structure of the sulphonamide on binding. Alternatively, binding of the enzyme to the bioconcentrator 4-sulphonamido-4'-aminoazobenzene can be detected by a shift of the 4-sulphonamido-4'-aminoazobenzene line at 928 to 926 cm$^{-1}$; the appearance of a band at 1125 cm$^{-1}$; and an increase in the relative intensities $I_{1426}/I_{1395}$ and $I_{1152}/I_{1145}$. Both sulphonamide derivatives have active groups (i.e., hydroxy and amino) at the end distal from the enzyme binding moiety which may readily be used to covalently immobilize the inhibitor on a solid substrate; and in a preferred form of the invention, the sulphonamide bioconcentrator is covalently immobilized.

Similarly, anti-dinitrophenol antibodies (anti-Dnp) may be detected and specifically identified by using a chromophoric hapten as the bioconcentrator, and a laser operating at 457.9 nm for exciting resonance in the hapten. (Potassium iodide must be mixed with the samples prior to analysis to quench fluorescence, unless SERS techniques are used.) Further, the anti-Dnp antibodies may be quantified, by measuring the ratios of (1) the increasing intensities of the new peaks that form or the decreasing intensities of the hapten peaks that shift, against (2) the intensities of hapten spectral wavebands that do not change in intensity when the antibodies bind. If, for example, 2,4-dinitroaniline is used as the bioconcentrator, the presence and identity of the mouse tumor antibodies MOPC 315 IgA and MOPC 460 IgA can be determined by monitoring the hapten line at 1337 cm$^{-1}$, which shifts to 1331 cm$^{-1}$ when MOPC 315 binds or 1325 cm$^{-1}$ when MOPC 460 binds; and the hapten line at 1279 cm$^{-1}$, which either shifts to 1268 cm$^{-1}$ when MOPC 315 binds or broadens when MOPC 460 binds. The hapten RRS lines at 1394 and 1355 cm$^{-1}$ do not change when either antibody binds, and may therefore be used for internal calibration and quantification of both. If only one antibody analyte is expected to be present, then the loss in intensity of the lines at 1337 and 1279 cm$^{-1}$ may be used for quantification of each; if either or both may be present, then the increases in intensities at 1331 and 1268 cm$^{-1}$ may be used to detect and quantify MOPC 315, and the increase in intensity at 1325 cm$^{-1}$ may be used to detect and quantify MOPC 460.

Furthermore, anti-dinitrophenol antibody fragments may be detected as well, using RRS analysis of the same chromophoric hapten bioconcentrator. For example, the Fab' fragment from MOPC 460 may be prepared by pepsin digestion of IgA monomer at pH 4.5. To determine the quantity of active fragments in a preparation, the wavebands at 1337, 1327, 1279, and 1273 cm$^{-1}$ are monitored. The active antibody fragment causes the line at 1337 cm$^{-1}$ to shift to 1327 cm$^{-1}$ and the line at 1279 cm$^{-1}$ to shift to 1273 cm$^{-1}$ when it binds to a 2,4-dinitroaniline bioconcentrator.

In a preferred form of the invention, the bioconcentrator is immobilized, and may be regenerated for additional analyses by rinsing the immobilized preparation with an analog such as 2,4-dinitrophenol. The dinitrophenol competes with the dinitroaniline for binding at the active site of the antibody, thereby releasing the antibody from the bioconcentrator, and permitting the antibody-analog complex to be rinsed away. Even if some small amount of the dissolved complex adsorbs in the vicinity of the immobilized bioconcentrator, the spectrum of the complex can be readily differentiated from the unique spectrum of the bioconcentrator-antibody complex.

In a "reverse" example, the antibody may serve as a bioconcentrator for the detection of dinitrophenyls. In a preferred form, suitable for the "real-time" monitoring of dinitrophenyls in solution, the bioconcentrator is comprised of the mouse tumor antibody MOPC 315 IgA coupled with Dnp-L-lysine through a flexible polypeptide link attached to the lysine moiety in the analog. As before, a laser operating at 457.9 nm is used for exciting resonance in the hapten and, if necessary, potassium iodide added for quenching fluorescence, if needed. When the sample stream does not contain any dinitroplienyls, the linked analog occupies the antibody's binding site, as may be determined by observing RRS peaks at 1382, 1338, and 1315 cm$^{-1}$. As the concentrations of one or more analytes increases, the analog is displaced, and its RRS peaks disappear. The presence of Dnp-NH$_2$ can be determined by the RRS spectrum of the analog disappearing and peaks at 1393, 1354, 1331, and 1268 cm$^{-1}$ appearing instead. The analyte Dnp-NHCH$_3$ will cause the appearance of peaks at 1371, 1340, and 1308 cm$^{-1}$; while Dnp-N(CH$_3$)$_2$ will cause the appearance of peaks at 1367, 1323, and 1306 cm$^{-1}$.

In an earlier example, a receptor immobilized in a membrane served as the bioconcentrator. Alternatively, a membrane itself may be a bioconcentrator, e.g., for detecting and identifying different types of bilirubins. For example, sphingomyelin liposomes may be used as the bioconcentrator, and RRS techniques used to detect and identify bilirubins such as IXα, IIIα, and XIIIα when the liposome-bilirubin complexes are irradiated at 514.5 nm and the resulting RRS spectra are analyzed in the 800–1600 cm$^{-1}$ window.

In yet another example, the invention may be used in the detection and quantification of a molecule labeled at a specific with a radioactive or stable label, i.e., to determine the success of a synthesis process. The enzyme thymidylate synthase (TSase) catalyses the reductive methylation of 2'-deoxyuridylate (dUMP) to thymidylate (dTMP), using the co-factor 5,10-methylenetetrahydrofolate (CH$_2$-H$_4$folate) as the methylating agent. Nucleotide analogs have been found to effectively inhibit TSase action; in particular 5-fluoro-2'-deoxyuridylate (FdUMP) has been shown to form a covalent ternary inhibitor complex with TSase and CH$_2$-H$_4$folate. RRS techniques may be coupled with TSase as the bioconcentrator and a laser operating at 337 nm in Raman Optrode detection and quantification of isotopically labeled CH$_2$-H$_4$folate, even in the presence of the unlabeled co-factor. For example, both $^{13}$C at paba-benzoyl position and D at the 3,5-positions on paba ring on the p-aminobenzoylglutamate (paba-glu) moiety of the co-factor produce large changes in the RRS spectra of the unlabeled co-factor complexed with the enzyme in the window from 600–1600 cm$^{-1}$.

In another example of the invention, microprobe RRS may be used in the Raman Optrode detection and identification of bacteria, such as *Rhodopsetidomotias capsulata, R. spheroides*, and *Rhodospirillum tenue*, with a synthetic polypeptide used as the bioconcentrator. In this example, polylysine hydrobromide is immobilized on a glass substrate by adsorption. Aqueous suspensions of bacteria are introduced to the bioconcentrator; and RRS spectra are obtained by excitation at 488 nm of bacteria captured by the bioconcentrator. A microprobe Raman system may generate and process spectra from as small a sample as a single microbial cell, using this invention. *R. capsulata* may be identified by the formation of bands at 953, 1002, 1059, 1151, 1189, 1459, 1514, 1586, and 1628 cm$^{-1}$. *R. spheroides* may be identified by the formation of bands at 956, 1001, 1153, 1189, 1257, 1389, 1425, 1515, and 1585 cm$^{-1}$; and *R. tenue* identified by bands at 957, 1002, 1046, 1087, 1149, 1187, 1199, 1282, 1355, 1440, and 1509 cm$^{-1}$. Note that a relatively nonspecific bioconcentrator such as a synthetic polypeptide is preferred only under certain circumstances, e.g., if the sample is reasonably well characterized, and there are only a handful of different species of microorganisms that might be present; or if many different microorganisms might be present and the Raman Optrode analysis is intended for the detection and identification of any or all of them (i.e., it would be impractical to use a different bioconcentrator for every bacterium of interest). However, for most applications, a preferred form of this invention would be to use antibodies raised against the specific microorganism(s) of interest as the bioconcentrators for bacterial analytes.

Similarly, viruses may exhibit unique NRS and may exhibit unique RRS spectra when irradiated at wavelengths that resonate with protein and/or nucleic acid components. For example, when captured and irradiated at 514.5 nm, the filamentous bacteriophages fd, If1, IKe, Pf1, Xf, and Pf3 may be detected and identified from discrete Raman bands in the spectral region 600–900 cm$^{-1}$ which are assignable to molecular vibrations of protein aromatic side chains and of the encapsidated, single-stranded DNA genomes. Viral analytes may be captured by, for example, antibody, lectin, or pathogen adhesion factor bioconcentrators in accordance with the Raman Optrode invention. Many different antibodies specific against a wide variety of human, animal, and plant pathogens rickettsial as well as bacterial and viral, may be procured from sources such as those listed in Linscott's Directory ("Linscott's Directory", 40 Glen Drive, Mill Valley, Calif. 94941.) In a preferred form of the invention, the antibodies are immobilized on a solid support surface, and the material containing the analyte microorganisms is brought into contact with the surface. In an alternative form, antibodies are added to and mixed with a liquid sample, where they bind with any target analyte microorganisms. The liquid sample is then passed over Protein A or Protein G immobilized on a solid support surface; the Fc portion of the complexed antibodies bind to the immobilized Protein A or Protein G, thereby also causing the microorganisms complexed to the antibodies to be captured. Alternatively, pathogen adhesion factors may be used as the bioconcentrators in the detection and analysis of bacterial, viral, and rickettsial diseases.

While the present invention may be practiced using NRS or RRS, surface-enhancement techniques, whether coupled with NRS to produce SERS, or with RRS to produce SERRS, may offer advantages for certain applications. Typically, SERS provides the same information as NRS but at a much better level of sensitivity; reports in the literature indicate that SERS may enhance a Raman signal by as much as a factor of $10^9$. The enhancement effect is related to molecules which are relatively close to or in direct contact with a roughened metal surface, thereby eliminating interference from signals from the bulk material. In addition, SERS quenches the fluorescence that might otherwise interfere with Raman analysis of certain molecules or mixtures, making it possible to work with additional analytes or with additional laser excitation wavelengths or throughout a broader spectral window. The literature reports that, in general, the SERS active metals include, but may not be limited to, Ag, Au, Cu, Pt, Li, Na, K, Al, In, W, AgBr, AgCl and $TiO_2$; silver has its optimum enhancement in the blue/green region of the visible spectrum, while gold and copper have optimum enhancements in the red. Theoretical calculations predict that large enhancements are achievable throughout the ultraviolet, visible, and near-infrared spectral regions. Surface protrusions ranging from 100 Å to tens of thousands Å ay be effective in producing the SERS phenomenon; however, in general, roughness protrusions 5 to 500 nm may be the best for producing strongly enhanced signals. All of these surfaces may be used in accordance with the present invention. In a preferred form of the present invention, however, silver is used, roughened to protrusions of about 200 nm. A preferred form of preparing roughened surfaces is through the use of microspheres deposited on a supporting surface, such as a paper tape or an ATR crystal, and then coated with a sputter-deposited thin metal film. The microspheres may be made from, for example, polystyrene, polyvinyltoluene, polybutadiene, teflon, aluminum, platinum, or zirconium. A final thickness of, e.g., silver, may be about 2,000 A for optimum results. However, other degrees of roughness and/or other metals, especially gold, copper, tungsten, or platinum, may provide superior results for some applications; and other methods for producing the roughened metal surface, other types of supporting materials (including for example, but not limited to, plastic, metal, or glass), and other configurations (including for example, but not limited to, small beads, optical fibers, or parallel plates) may be used in accordance with this invention. In addition, the metal surface may be treated to cause the electrochemical formation of an oxide layer, which may enhance the signal even further under some circumstances. SERS and SERRS can be used as well as NRS and RRS in accordance with this Raman Optrode invention for directly monitoring/detecting substances in the air, without any requirement for a liquid scrubbing step.

In a preferred form of the invention, the bioconcentrator is immobilized on the SERS-active surface by covalent bonding, preferably by thiol-disulfide exchange, although any other suitable immobilization procedures as are known by those versed in the art may be used instead, including, for example, other covalent linkages, adsorption, adsorption coupled with cross-linking, entrapment, etc. Molecules or moieties within the molecule do not have to be directly in contact with the roughened metal surface to exhibit the SERS effects. However, the enhancement factor decreases sharply as the distance frorrm the surface increases, i.e., the enhancement factor is known to drop an order of magnitude within about 5 nm of the surface. By way of example, a typical IgG antibody is ~6 nm by 10 nm; therefore, if an antibody were to be immobilized by covalent bonding between the SERS-active surface and the Fc portion of the antibody, and the antibody were to "stand upright" after immobilization, the antibody active sites would be outside the 5 nm range for maximum SERS effect. However, it is known that immobilized antibodies which are well-spaced tend to "lean over" and thus would present the active site near the surface; literature reports that the calculated thickness for immunoglobulin absorbed on silver is 50 A. Even so, in some cases it is preferred to attach an antibody fragment, rather than an entire antibody molecule. Not only does this optimize the SERS effect, but it may also improve the stability of the bioconcentrator preparation. The $F(ab)_2'$ fragment may be prepared by pepsin digestion, cleaving the antibody just below the hinge, while the Fab' fragment may be prepared by papain digestion.

In yet another example of the Raman Optrode invention, microorganisms or living cells may be detected and identified through the use of SERS analysis and nucleic acid probe bioconcentrators. It has been shown that single-stranded poly(A) adsorbed on a roughened silver surface will give rise to two intense bands in the SERS spectrum at 735 and 1334 $cm^{-1}$ when irradiated at 514.5 nm. Addition of poly (U), leading to the formation of a double helix, essentially eliminates both bands; but the addition of poly(C) [which will not form a double helix with poly(A)] has minimal effect on the single-strand poly(A) SERS spectrum. Therefore, the degree to which a single-stranded nucleic acid will form a double helix with a nucleic acid probe can be determined by analyzing the bands associated with the adenosine bases. Calf thymus DNA from Sigma, thermally denatured to single-stranded nucleic acids, gives rise to intense SERS signals at 734 and 1134 $cm^{-1}$; double-helical native DNA yields band which are much less intense. To use the Raman Optrode for the detection and identification of microorganisms or living cells, then, single-stranded nucleic acid probe bioconcentrators would be prepared from "known" microbial or cellular DNA by methods which are known in the art; and the bioconcentrators then covalently immobilized on a roughened silver surface, and their spectra entered into the library. To identify the microorganism or cellular material in an "unknown" sample, an aliquot of the sample would be treated in a fashion suitable for disrupting any cellular content, e.g., lysing all microbes or cells, and then using suitable restriction endonuclease enzymes to digest any sample nucleic acid content, using procedures such as are known to those versed in the art. An aliquot of the digested sample preparation would be deposited on the immobilized bioconcentrator on the roughened silver surface and allowed to hybridize. This may be done with or without separation of the nucleic acid fragments produced by enzymatic digestion (e.g., with chromatographic or blot techniques), depending on the microorganisms of interest, the probes which have been developed, and the type of sample to be analyzed. The degree to which single-stranded DNA from the sample binds and forms a double helix with the immobilized bioconcentrator may be determined by measuring the change in intensity of the Raman lines from the adenosine bases in the probe. In a preferred form of the invention, after analysis is complete, the single strand nucleic acid from the microorganism is stripped away from the immobilized nucleic acid probe bioconcentrator, and the "renewed" probe is used again.

Earlier, NRS analysis of a nucleic acid bioconcentrator was cited as an example of a Raman Optrode approach to the detection of the chemical warfare agent mustard. When NRS is used, only two bands of the bioconcentrator baseline spectrum are affected and can be monitored to detect the presence of, for example, methylnitrogen mustard. SBRS techniques using a charged silver electrode to orient the immobilized DNA might be a preferred approach, as a means to gain additional specificity as well as additional sensitivity. For example, at the adsorption potential of −0.2 V vs. Ag/AgCl, which corresponds to a highly positively charged surface, the SERS spectrum of adsorbed DNA is characterized by a strong band at 236 $cm^{-1}$, attributable to the electrostatic interaction of negatively charged phosphate groups with the positively charged silver surface. This band, which is not seen when the immobilized bioconcentrator is monitored on a neutral silver surface, decreases in intensity after the reaction of the DNA with alkylating agents, due to a decrease in the interaction of the phosphate groups with the silver surface. The methylated DNA also shows new SERS bands at 656, 700, and 1360 $cm^{-1}$, which correspond to characteristic vibrations of methylated guanine residues; and decreased intensities of the bands at 1200 $cm^{-1}$ and 1300 $cm^{-1}$, related to a conformational change of DNA at the location of modified guanine-cytosine nucleic base pairs. Thus, by using a positively charged roughened silver surface, six bands may be monitored in accordance with this invention for the detection of vesicant agents, instead of the two that are affected and may therefore be monitored using NRS techniques.

When surface enhancement, already discussed, is coupled with RRS to produce SERRS, it results in an enhancement factor which is an addition of the enhancements achieved by RRS or SERS alone. The extraordinary sensitivity and specificity which can be achieved by SERRS may have significant advantages for some applications of the Raman Optrode invention.

For example, as previously discussed, when the 514.5 nm line of an argon ion laser is used to irradiate DNA, only NRS scattering is produced. Therefore, a relatively large amount of nucleic acid must be used to produce a signal strong enough for analysis when this wavelength is used for excitation, even when SERS techniques are employed. However, by inducing resonance in an analyte bound to a DNA bioconcentrator and by using Raman microscopy as the transducer, very small amounts of DNA may be used as a bioconcentrator, and exceptionally low concentrations of various antitumor drugs may be detected. In this particular example of the invention, a stock solution of the calf thymus DNA (Sigma Chemical Co. type I) is prepared in phosphate buffered saline. The calf thymus DNA suspension is mixed with the sample to be analyzed, and then with a fresh silver hydrosol aggregate suspension. A microliter of the resulting adsorbed DNA/DNA-analyte complex suspension placed in a capillary tube in the microprobe; and the SERRS spectrum obtained in the window 350–2000 $cm^{-1}$. The DNA itself does not give any appreciable spectrum under these conditions. If, however, the antitumor drug adriamycin is present in the "unknown" sample, even at concentrations below 1 molecule per 1000 base pairs, the presence and identity of the adriamycin may be determined by strong increases in the intensities of wavelengths at 353, 448, 1226, 1255, 1318, 1464, and 1642 $cm^{-1}$. If the "unknown" contains berenil (an anti-trypanosomal agent), the agent's presence and identity may be determined from detecting the formation of strong peaks 1598, 1473, 1431, 1398, 1349, 1309, 1188, 1164, and 770 $cm^{-1}$; while the antitumor ellipticine bound to DNA gives strong peaks at 1617, 1406, 1273, 1027, 878, 587, 481, and 380 $cm^{-1}$. The antitumor agent meta-amsacrine, as well as the drugs distamycin and mitoxantrone, may be similarly detected and identified.

In another example of using SERRS in the present invention, the protein cytochrome P-450 is used as the bioconcentrator in the detection and identification of one of its substrates, the drug benzphetamine. The protein, isolated from rabbit liver microsomes and reconstituted and immobilized in a phospholipid membrane on a roughened silver surface, is irradiated with a laser operating at 406 nm. When an "unknown" sample is introduced to the immobilized protein preparation, the controlled substance may be detected by observing an increase in intensity of the 254 $cm^{-1}$ band; a small decrease in intensity of the band at 676 $cm^{-1}$ compared to the doublet at 349 and 384 $cm^{-1}$; a shift in the frequency of the 720 $cm^{-1}$ band to 724 $cm^{-1}$; a relative decrease of the intensity of the line at 1500 $cm^{-1}$ with respect to the line at 1491 $cm^{-1}$; and a frequency down-shift of the peak at 1578 $cm^{-1}$ by 3 $cm^{-1}$ to 1575 $cm^{-1}$. Further, changes in the oxidation state of the enzyme bioconcentrator can also be detected. When irradiated at 406 nm, oxidized P-450($Fe^{3+}$) can be identified by strong bands at 1491 and 1370 $cm^{-1}$, whereas reduced P-450($Fe^{2+}$) can be identified by bands at 1343 $cm^{-1}$ and 1359 $cm^{-1}$.

In a strongly basic environment, cytochrome P-450 is converted to the biologically inactive form P-420, which is believed to be the first step in any denaturation of the enzyme. When irradiated at 514.5 nm, the active and inactive forms immobilized on the roughened silver surface may be clearly differentiated, with the spectrum of cytochrome P-420 giving rise to a new band at 1627 $cm^{-1}$ and a large relative decrease in the intensity of the 1400 $cm^{-1}$ band system characteristic of cytochrome P-450. Hence, the status of the cytochrome P-450 bioconcentrator may be monitored during SERRS-based Raman Optrode detection of benzphetamine by periodically irradiating the bioconcentrator at the second wavelength, i.e., at 514.5 nm.

The previous examples of Raman Optrode processes describe approaches in which a single laser wavelength is used to excite Raman scattering. However, for some applications, a preferred form of this invention would be to collect and analyze two or more spectra generated through irradiation by two or more laser wavelengths, i.e., to generate "three-dimensional (3-D) spectra." Two or more lasers might be used; alternatively, a single laser might be used and alternately tuned to two or more different lines during spectral analysis. 3-D analysis would offer a number of advantages for certain applications, e.g., when exceptional specificity is desired, or when the Raman Optrode is intended to detect low concentrations of multiple analytes that do not possess many chromophores in common.

For example, the enzyme dihydrofolate reductase may be used as the bioconcentrator for the 3-D RRS analysis and detection of niethotrexate, a drug used for the treatment of childhood leukemia. Dihydrofolate reductase catalyzes the NADPH-linked reduction of dihydrofolate to tetrahydrofolate. Methotrexate, which is structurally similar to folate and contains p-aminobenzoyl and pteridine groups, both of which are resonance-active chromophores, inhibits this enzyme. Resonance can be excited in p-aminobenzoyl and pteridine groups by irradiation at 324 and 350 nm, respectively. When the bioconcentrator is irradiated at 324 nm, the presence of methotrexate can be determined by the loss of the 1685 $cm^{-1}$ Raman band, which can be observed in the NADPH-enzyme binary complex but is absent from the NADPH-methotrexate-enzyme ternary complex. When the irradiating light is changed to 350 nm, the presence of the drug can be confirmed by the presence of a strong band at 659 cm$^{-1}$, which is present only in the drug-enzyme complex.

In another example, 3-D RRS may be coupled with a nucleic acid bioconcentrator for the highly specific detection of the drug actinomycin D, an antibiotic effective against many gram-positive and gram-negative organisms. The drug is highly toxic to humans and is known to inhibit the transcription process. In this example of the invention, specific changes in the RRS spectra of both the drug and the bioconcentrator are monitored, thereby providing exceptional confidence in the identity of the captured analyte. First, by UV excitation at wavelengths of 300 and 280 nm, the 1582 cm$^{-1}$ line of adenine and the 1492 cm$^{-1}$ line of guanine in the DNA bioconcentrator can be seen. When the actinomycin-DNA interaction takes place, the intensity of the 1492 cm$^{-1}$ line decreases significantly, indicating that guanine bases are disturbed by actinomycin, while the 1582 cm$^{-1}$ line remains unchanged (and may, accordingly, be used for quantitative analysis). Next, laser excitation at 458 nm is used to excite resonance in the actinomycin chromophore. At this last wavelength, unbound antibiotic gives resonance-enhanced Raman bands at 1505, 1489, 1405, 1385, and 1265 cm$^{-1}$. Of these, the 1385, 1489, and 1505 cm$^{-1}$ bands are sensitive to interaction with DNA. In particular, large intensity changes are observed for the 1489 and 1505 cm$^{-1}$ lines when actinomycin D binds to the bioconcentrator.

In yet another example of the invention, 3-D RRS may be coupled with an antibody concentrator for the highly specific detection and identification of bacteria. Monoclonal IgG antibodies raised against *Staphylococcus epiderinidis* (Caltag Laboratories Inc, San Francisco, Calif.) may be used as the bioconcentrator, immobilized on a glass slide, and a few drops of the liquid sample to be analyzed applied to the surface, incubated, and rinsed prior to Raman analysis. Irradiation at 251 nm and 242 nm may be used to excite resonance primarily in the bacterial DNA with contributions from the aromatic amino acids, irradiation at 231 nm to excite resonance primarily in the bacterial protein tryptophan and tyrosine peaks; and irradiation at 223 nm to excite resonance primarily in the bacterial protein amino acid peaks. The three RRS spectra may be collected and analyzed from the region 900–1800 cm$^{-1}$ by comparison against the library of model reference spectra for the exceptionally specific identification of the captured bacteria. In a preferred embodiment, the antibodies are immobilized on a roughed metal surface on an optical waveguide, and the exciting light introduced and the resulting spectra collected through the optical waveguide, i.e., SERRS is used for even more specificity and sensitivity in the 3-D analysis of the target microorganism(s). Analysis of the organism may thereby be simplified and its reliability improved through use of SERS to enable the selective query of surface taxonomic markers while also enabling the use of a wide range of laser wavelengths to selectively enhance the signals of a wide range of taxonomic markers without interference from fluorescence. Further, if desired, heat-killed *S. epidennidis* may be detected and identified, as well as viable bacteria, and may be differentiated from the viable microbes, for example, by comparing the measured RRS spectrum of the complexed cells with a model reference spectrum obtained at 231 nm excitation. Cell fragments from the *S. epidennidis* bacterium may be detected by noting the presence of the appropriate amino acid lines in the spectra taken at 231 and 223 nm, and the absence of lines associated with bacterial DNA in the spectra taken at 251 nm and 242 nm.

In yet another example of the invention, a series of different categories of bioconcentrators that are specific for different chemical and biological warfare agents may be immobilized on the surface of a dipstick. For example, monoclonal antibodies against the spores from *Bacillus anthracis* (USAMRIID) may be immobilized at one locaition on the roughened metal surface of the dipstick, the enzyme acetylcholinesterase from *E. electricus* (Sigma) at a second, enriched preparations of the acetylcholine receptor in membrane fragments from the *Torpedo marmorata* electric organ at a third, and the ganglioside GT1b (Calbiochem) at a fourth. The dipstick may then be inserted into samples collected by a bioaerosol liquid impactor, rinsed, and inserted into an imaging Raman microprobe. Anthrax spores captured by the antibodies, chemical warfare nerve agents captured by inhibiting the acetylcholinesterase; (+)-tubocurarine (the active ingredient in curare) bound to the acetylcholine receptor, and botulinum toxins bound to the immobilized ganglioside can be detected and identified simultaneously by the imaging Raman system.

In a preferred form of this invention, the spectrum library contains spectra of the fully reactive and partially denatured or deactivated or poisoned or spent bioconcentrator; and the measured spectrum is compared against the model spectra of reactive and partially denatured or deactivated or poisoned or spent bioconcentrator to determine whether a sufficiently large percentage of the bioconcentrator is reactive and capable of binding its analyte(s). Denaturation or deactivation of the bioconcentrator may occur through temperature fluctuations, changes in pH, or the presence of solvents or surfactants in a liquid sample, and may be determined through Raman spectral analysis in accordance with this invention as previously described. For example, chemically denatured IgG antibodies (e.g., exposed to alkaline solutions) may be detected by shifts in the amide III and amide I' lines from 1240 to 1248 cm$^{-1}$ and from 1667 to 1656 cm$^{-1}$, respectively, with decreasing intensities; the tryptophan band at 1573 cm$^{-1}$ increasing in intensity, and the bands at 1359 and 879 cm$^{-1}$ decreasing in intensity; the tyrosine band intensity ratio of the $I_{856}/I_{830}$ decreasing from 10:7 to 9:10; and a strong peak appearing at 939 cm$^{-1}$.

A wide variety of Raman Optrode reactive capacity analyses may be performed on a wide variety of biological components and biotechnology products as well, using a wide variety of Raman spectroscopy techniques, in accordance with this invention.

For example, in solid phase peptide synthesis, a polymer support-resin is used in the synthesis of a polypeptide with a well-defined chain length and secondary structure. However, problems may be encountered; contributing factors are believed to be interaction between the growing peptide chains attached to the resin, e.g., beta sheet formation, and/or incomplete removal of the protection group. Due to the immobilized form of the synthesized biological, it is impossible to analyze the chain during synthesis using conventional approaches. However, Raman Optrode reactive capacity analyses may be used in accordance with this invention to monitor the synthesis process in situ, tracking the secondary structure and the presence or absence of protection groups while the synthesis reactions are under way and thereby permitting corrective procedures to be implemented during processing. For example, the conformation of a growing polylysine chain is affected by local microenvironmental changes in pH, ionic concentration, and temperature which may not be detectable by measuring the pH, ionic concentration, and temperature of the bulk medium. However, in accordance with this invention, RRS techniques may be used to monitor and control the growing polypeptide in situ by irradiating the polypeptide at 218 nm. Polylysine in a random coil form can be detected by the observation of strong peaks at 1258, 1386, 1559, and 1655 $cm^{-1}$; the α-helix form can be detected by the strong peaks at 1548 and 1644 $cm^{-1}$, and broad, weak peaks 1275 and 1348 $cm^{-1}$; and β-sheet formation can be detected by strong peaks at 1244, 1559, and 1661 $cm^{-1}$, and a moderately strong doublet at 1359 and 1400 $cm^{-1}$. Quantitative analyses may be accomplished by using $NaClO_4$ as an internal standard, and comparing key bands from the polylysine spectrum against the 932 $cm^{-1}$ band from the $ClO_4-$. At alternating steps in the synthesis process, a laser operating at 1064 nm may be used for NRS detection of the incomplete removal of the protection group, by monitoring the band at 1025 $cm^{-1}$.

In another example, Raman Optrode reactive capacity analyses may be used in the nondestructive detection of thermal or chemical denaturation of, e.g., enzymes such as lysozyme. NRS and/or RRS techniques may be used to monitor this enzyme's reactive capacity. Thermal denaturation of lysozyme may be measured by monitoring the amide I band (which shifts to a higher frequency and decreases significantly in intensity upon heating), and the amide III bands (which move to a lower frequency and decrease significantly in intensity) in the NRS spectrum. The effect of heat denaturation on side chains is mainly to disrupt those side chains involved in hydrogen bonding and hydrophilic and hydrophobic interactions. The covalently linked side-chain disulfide bridge is not roken by heat treatment; the lysozyme S-S stretching vibration band at 509 $cm^{-1}$ does not change even when heated to 76° C. Hence, this particular band may be used in quantitative assessments of the enzyme's reactive capacity, in accordance with this invention.

If more sensitivity is desired, ultraviolet resonance Raman scattering (UV-RRS) techniques may be used. When the lysozyme is irradiated at 231.5 nm, decreased reactive capacity due to thermal denaturation may be detected by the 1178 $cm^{-1}$ peak decreasing slightly in intensity and shifting to 1176 $cm^{-1}$; the 1240 $cm^{-1}$ peak shifting to 1248 $cm^{-1}$; the shoulder at 1340 $cm^{-1}$ disappearing; the peak at 1456 $cm^{-1}$ shifting to 1461 $cm^{-1}$; and the small peak at 1681 $cm^{-1}$ disappearing.

The enzyme exhibits different denatured forms, the form that is produced depending on the process that caused the denaturation. The causative factor(s) in lysozyme denaturation can therefore be determined by the appropriate analysis of the resulting Raman spectrum, in accordance with this invention. For example, chemical denaturation of lysozyme such as that caused, e.g., by exposure to reagents such as dimethyl sulfoxide, guanidine hydrochloride, urea, sodium dodecyl sulfate, and LiBr, may be detected by measuring the intensity of the amride III Raman band at 1260 $cm^{-1}$ relative to the intensity of the amide III band near 1240 $cm^{-1}$ (i.e., the ratio $I_{1260}/I_{1240}$) in the NRS spectrum of the enzyme. Exposure to other reagents may result in actual chemical modification, rather than simple alterations in the conformation, e.g., disulfide bond cleavage, which may be determined by the disappearance of the 507 $cm^{-1}$ S—S stretching vibration band, and large shifts in the amide I band from 1672 to 1660 $cm^{-1}$ and in the amide III bands from 1254 to 1243 $cm^{-1}$ and from 1271 to 1263 $cm^{-1}$.

In another example of Raman Optrode reactive capacity analysis, thermal denaturation of insulin stored in crystalline powder form may be monitored by NRS techniques. The native insulin has a major band at 1662 $cm^{-1}$ with a shoulder at 1680 $cm^{-1}$; a major band at 1270 $cm^{-1}$ and the rather weak shoulders at 1288 $cm^{-1}$ and 1239 $cm^{-1}$; and bands at 1303, 1269, and 1284 $cm^{-1}$. Denatured insulin may be detected by the native 1662 $cm^{-1}$ band shifting to 1672 $cm^{-1}$; a new band appearing at 1230 $cm^{-1}$; strong bands appearing in the region of 946 $cm^{-1}$ and 934 $cm^{-1}$; the intensity of the native S—S stretching vibration at 515 $cm^{-1}$ increasing; the C—S stretching vibration at 670 $cm^{-1}$ changing to 668 and 680 $cm^{-1}$; and the native C—S stretching vibration at 668 $cm^{-1}$ shifting to 657 $cm^{-1}$, with an intensity decrease. The S—S stretching vibration at 516 $cm^{-1}$ does not change, and, in accordance with this invention, may be used in quantitative analysis. Hence, the degree of storage degradation that has occurred may be determined nondestructively in accordance with this invention.

Insulin is a small (5.7 kilodalton) protein with two chains, A and B, linked by two disulfide bridges. At lower concentrations insulin is known to exist in different aggregation states, monomer, dimer, tetramer, and hexamer, depending on its concentration, pH, $Zn^{2+}$ binding, and ionic strength. Aggregation states may be readily determined, in accordance with this invention, by RRS techniques. For example, when the solution is monitored under irradiation at 218 nm, the 1617 $cm^{-1}$ band increases in intensity when compared to the 1605 $cm^{-1}$ band as the monomer shifts to the dimer.

It is known that heat denaturation of ribonuclease (RNase) proceeds via a stepwise unfolding rather than a transition between two states. Thermal denaturation may be detected by monitoring the ratios $I_{832}/I_{852}$ and $I_{1000}/I_{972}$, and the band near 510 $cm^{-1}$ in the NRS spectrum of the enzyme. The NRS spectrum for native, fully reactive RNase shows a ratio $I_{832}/I_{852}$ of 1.0/0.8, but by the time the enzyme is completely denatured, the ratio is reversed, i.e., $I_{852}/I_{832}$ is 1.0/0.8. Similarly, the relative intensities of the two strong bands near 1000 $cm^{-1}$ are reversed by the time heat denaturation of the enzyme is total. Changes in the frequency and half-width of the band near 510 $cm^{-1}$ may also be iused in determining the enzyme reactive capacity, with the band shifting down in frequency and becoming broader upon denaturation.

As discussed previously, Raman spectral analysis is compatible with analytes in many different physical states and types of sample matrices. Accordingly, processes or devices in accordance with this invention may take many different forms and configurations. Some examples of processes or device which can be used to perform the invention are given below. These specific examples are not intended to limit the scope of the invention described in this application.

As one example, a thin film of roughened metal may be coated on a badge, and antibody specific for a hazardous material such as a toxic pesticide may be immobilized on the metal film. The badge may be designed to be worn as a passive dosimeter by a factory worker. Part of the badge may be covered with an optically transparent, impermeable film. Further, each badge may be encoded with a specific identification unique to the badge and to the worker to whom the badge is assigned. At the beginning and end of the work shift, the badge may be inserted into a Raman spectrometer read-out system (containing the light source, spectrometer, and analysis hardware and software), which may compare the spectra of the exposed and the shielded antibodies during quantitative manipulations. The read-out system may also have internal calibration, means for reading the badge identification code, extra memory, and an internal clock. At the beginning of the day, the Raman read-out system measures the quantity of fully reactive antibody on the unshielded section of the badge, and provides a warning if there is insufficient activity for the badge to be worn for a full shift. It stores the spectrum of the badge in memory, correlated to the identification code. At the end of the day, the Raman read-out system produces a new spectrum and compares it against the one in memory. By comparing the difference spectrum against model reference spectra, the quantity of pesticide which has become bound to the antibody during the day may be determined. In addition, the read-out system may measure the time interval during which exposure took place, and calculate the time-averaged exposure of the worker to the pesticide on that day. Further, the day's spectra may also be compared against those obtained on previous days (or against data generated with other badges worn by the same worker), and the individual's cumulative exposure thereby calculated as well as his time-averaged daily dosage.

In another form, an enzyme which is inhibited by chemical warfare agents, such as cholinesterase, may be immobilized on a roughened metal surface at the tip of a fiber optic. During operation, the coated tip of the fiber optic may be inserted into a charcoal filter bed. The excitation light may travel through the fiber to the coated tip, and the scattered light travel back to a Raman spectrometer through the fiber. The device may therefore be used to detect potential breakthrough in the charcoal filter bed. Since several different nerve agents will bind to cholinesterase, but each one will generate a different spectrum when bound, the device will not only detect agent breaking through, but will also provide information on the identity of each nerve agent which is present.

In another form, a water analyzer may be provided in which a flow-through cell has receptors immobilized in an optically transparent cell. When the concentration of toxins in the water rises, the toxin molecules bind to the receptors as water flows through the cell. As the concentration of toxins in the water subsequently decreases, the receptors release the toxin molecules. The presence and identity and quantity of each toxin may be determined by a Raman spectrometer incorporated into the device; the software in the system may do all calculations and data interpretation and manipulation, so that the information on each toxin shows on an LCD display. The device may be used to measure toxic effluents from an industrial process plant, for example; or to measure the purity of a public water supply.

In yet another form, lectins may be immobilized on a disposable dipstick. The dipstick may be inserted into a vial containing a blood or urine sample, and then inserted into a Raman spectrometer device. The spectrum of the lectin-ligand complex may then be obtained to detect the quantity of various sugars, including glucose, present in the sample.

An air monitor for nonvolatile drugs may have a liquid scrubber which collects/concentrates vapors and aerosol particulates, the liquid dissolving any drugs adsorbed onto or forming particulates captured by the scrubber. This liquid may be periodically drained and mixed with a sol-gel solution containing several different receptors, each one specific for a different category or class of drugs. The mixed solution may then be cycled through a flow-through cell in a Raman spectrometer, which has the optics and software necessary to measure changes in the SERS or SERRS spectra of all of the receptors and thereby identify all of the different drugs which are present.

As an example of using Raman Optrode technology to detect and identify microorganisms or cells through the use of nucleic acid probes, suitable probes may be immobilized at the tips of fiber optics in a bundle. To use the Raman Optrode, the sample may be treated to lyse any cellular material and to enzymatically digest the DNA and/or RNA content into nucleic acid fragments. The Raman Optrode bioconcentrator fiber optic tip may then be dipped into the pre-treated sample and hybridization allowed to take place. The fiber optic is attached to a light source and spectrometer; the excitation wavelength(s) travel through the fiber optic to the probes at its tip, and the resulting spectra travel through the fiber optic to the spectrometer, which collects, processes, and analyzes the spectra to detect hybridization between the sample and each different probe at the end of each fiber. Once analysis is completed, the fiber optic tip may be heated with, rinsing to regenerate the single-stranded nucleic acid probes. Because the spectra can be used to confirm that the are completely regenerated and all sample strands have been removed, the fiber optic probe can be safely re-used indefinitely.

Alternatively, pathogen adhesion factors may be immobilized on an Attenuated Total Reflectance (ATR) crystal surface coated with a roughened metal film, and a blood sample applied to the surface. Viruses in the blood sample bind to the pathogen adhesion factors. Two or more exciting light wavelengths may then be launched sequentially into the ATR crystal in series, and the resulting 3-D SERRS spectral information captured through the evanescent wave phenomenon. The 3-D SERRS spectra may then be used to detect the presence of the viruses, and to identify each type, as the viral coatings and nucleic acids for each genus generate distinct, unique spectra.

In yet another configuration, a sampling device may be used to collect samples from various bodies of water or various locations in a pond or stream. The sampling device may contain a spool-mounted tape cassette, a liquid pump, a sampling probe, batteries, and a thermistor, and hardware and software for entering and recording sample identification information; and the tape may bear a number of different strips, each strip being coated with a different metal film and a different mixture of antibody fragments, enzymes, and receptor subunits. The operator enters information concerning the sample, and may then dip the sampling probe into the water to be analyzed and push a button. Pushing the button may cause the sampling device to pump a given quantity of water through the section of the tape in the cassette window, to record sample identification information on the tape next to the strips of bioconcentrators in the sampling window at that time, and then to advance the tape so that a fresh section showing the various strips is in the sampling window of the cassette. After all of the samples have been collected, the operator may return to the laboratory and place a sampling accessory into a multichannel scanning Raman spectrometer. The tape cassette analysis accessory is designed to accommodate the tape cassette. The operator may then remove the cassette from the sampling device and insert it into the accessory within the Raman spectrometer. The multichannel scanning spectrometer may be programmed to scan the strips at one or more sequential spectral bands; and, if a strong signal is seen at a particular location on a given strip, to then focus on that location and generate and analyze one or more full SERS spectra. If a full SERS spectrum corresponds to that of a priority pollutant (chemical or microbial) in the spectral reference library, then the Raman spectrometer may be designed to print out the identity and quantity of the pollutant next to the sample identification code (as entered by the operator in the field). Once the analysis of a given section of tape is completed, the Raman spectrometer tape cassette analysis accessory may be designed to automatically advance the tape to the next section and go through the analysis cycle again, continuing until all sections of the tape have been analyzed or all samples with recorded identification have been processed.

In yet another configuration, antibody bioconcentrators may be immobilized on the uncladded surface of a thin, flexible, fiber optic in a coil or bundle, coupled to a long, cladded fiber optic cable. Exciting light traveling down the cable is launched into the coil at an angle, to travel through the coil by the evanescent wave of multiple internal reflection, thereby causing the light to interact repeatedly with the bioconcentrators on the surface of the coil. As the evanescent wave reaches the end of the coil, it is transferred back into the cable for transport to a Raman spectrometer. By using an evanescent wave, exceptional sensitivity may be attained. Such a configuration may be used for remote sampling of extremely dilute analyte concentrations, e.g., for groundwater monitoring. In a preferred form of the invention, the antibody bioconcentrators would be modified to be "reversible competitive recognition units" (U.S. Pat. No. 5,156,972, Oct. 20, 1992, "Analyte Specific Chemical Sensor with a Ligand and an Analogue Bound on the Sensing Surface", D. Issachar), thereby enabling continuous "real time" monitoring in the groundwater borehole. Alternatively, the more conventional antibody regeneration processes. such as temperature perturbation, chaotropic reagents, or solvent polarity adjustment, may be considered for use in suitable remote monitoring applications.

If desired, a groundwater monitoring system might be designed with a fiber optic array, similar in some aspects to the passenger screening portal described earlier. Sampling devices (in this case, the fiber optic coils) are located in various groundwater monitoring boreholes, and may also be located at various depths within each borehole. A fiber optic cable may be used to transport exciting light to each protein-coated coil, and to transport the resulting Raman spectra from each protein-coated coil to a single, centralized Raman spectrometer. In this example, instead of combining the spectral signals for processing and analysis, the spectral signals from each coil are analyzed separately, either sequentially or simultaneously through the use of, for example, a multichannel spectrometer with a detector array, with the spectral signals from a given fiber optic collected, dispersed, and focused on a row of detectors in the detector array. In the event the spectrum of a bioconcentrator-ligand complex matches that of a bioconcentrator-pollutant complex, the centralized Raman spectrometer might transmit a warning signal to a remote operator station, indicating the location of the borehole and the depth at which the pollutant was detected.

In yet another example, powdered enzyme may be packed loosely into a small capillary tube and held in place by glass wool plugs. Air may be pulled through the tube, with the vapors of any of the enzyme's inhibitors binding to the bioconcentrator. The capillary tube may be returned to the laboratory, the glass wool plugs removed, and the powdered enzyme tapped into a typical Raman spectrometer powder/solids sampling accessory for Raman analysis and detection and identification of the captured inhibitor(s).

A Raman Optrode for the automated detection and identification of blood antibodies may comprise a carousel for sample vials; a needle sample injector; a second carousel containing small transparent boats coated internally with a roughened metal film and an immobilized layer of antigens; a Raman spectrometer subsystem; and a printer. Sealed vials with rubber stoppers containing the blood samples may be placed into the first carousel. The needle sample injector may automatically pierce the rubber stopper in the first vial, remove an aliquot of sample from the vial and transfer it to the first SERS-active plate on the second carousel, and then pull and expel an aliquot of rinsing liquid into a waste reservoir before piercing the stopper in the next vial. Meanwhile, the antibodies in the sample removed from the first vial incubate with the immobilized antigen layer in the boat while the second carousel rotates, bringing the first SERS-active boat containing the blood sample into the Raman spectrometer subsystem. When the boat reaches the Raman read-out station, 3-D SERRS analysis for the detection and identification of the blood antibodies may take place, with the exciting light being launched through the bottom of the transparent boat and metal film before comning into contact with the antigen-antibody complexes, and the resulting spectra recaptured through the evanescent wave phenomenon. When analysis is completed, the results indicating the antibody content of each sample may be provided in a printout.

A Raman Optrode for the reactive capacity analysis of insulin may consist of a Raman spectrometer subsystem with a carousel for the introduction of vials as the sampling accessory. The insulin is stored in optically transparent vials. When the insulin is to be shipped, the vials are first loaded into the carousel. The moving carousel exposes each vial in turn to irradiation. The resulting Raman spectrum of the stored insulin is compared against reference model spectra of crystalline powder insulin of known activities. When a vial containing an unacceptably high percentage of denatured insulin is detected, the Raman system sounds an alarm, or may, if desired, be designed to eject that vial from the carousel and/or place a mark on the vial indicating the status of its contents. The system may also be designed to place a mark on each vial indicative of the date on which the insulin in that vial was last analyzed.

A Raman Optrode for the reactive capacity analysis of a polypeptide undergoing solid phase synthesis may consist of an array of removable fiber optics. The surface of each fiber optic has been functionalized for the attachment of a resin film such that polypeptides are growing on the surfaces of the fiber optics. The irradiating light is brought into contact with the polypeptide and the resulting Raman spectrum is captured by the evanescent wave phenomenon. The Raman Optrode is designed to automatically adjust the processing steps on the basis of the spectral information, e.g., to continue incubation with reagents for the removal of protective groups until the spectral information indicates that deprotection is complete, inject acid, base, or buffer if the pH changes, etc.

While the above detailed description of this invention and preferred forms thereof have been described, various modes of practicing this invention will be apparent to those skilled in the art based on the above detailed disclosure. These and other variations are deemed to come within the scope of the the present invention. Accordingly, it is understood that the present invention is not limited to the detailed description.

What is claimed is:

1. The process for any one of at least the detection, identification and quantification of one or more analytes by Raman spectroscopy comprising the steps of:

provididng a bioconcentrator which binds with at least one analyte, bringing into contact with said bioconcentrator at least one analyte to effect binding of the at least one analyte on to the bioconcentrator to form a medium to be analyzed consisting essentially of said bioconcentrator and said at least one analyte and wherein at least some of said at least one analyte is bound to said bioconcentrator, irradiating the said medium containing said bioconcentrator and the bound at least one analyte thereon with light from a source wherein said light produces Raman scattering from the irradiated bioconcentrator and the at least one analyte bound thereto, wherein the Raman scattering is not produced by a reporter attached to either the bioconcentrator or the analyte, collecting and processing the Raman scattering emanating from said bioconcentrator and the at least one analyte on said bioconcentrator, and analyzing the processed Raman scattering to determine the presence and/or identity of the at least one analyte.

2. The process as set forth in claim 1 wherein the bioconcentrator is located on a support member and wherein the bioconcentrator is selected from the group consisting of: molecules, macromolecules, complexes, fragments of a molecule, and fragments and subunits of a complex, all derived from a biological source; ligands that will bind molecules, macromolecules, complexes, fragments of a molecule, subunits of a complex, and fragments of a complex, all derived from a biological source; wherein said molecules, macromolecules and complexes are selected from the group consisting of enzymes, enzyme cofactors, coenzymes, antibodies, antibody fragments, hemeproteins, natural and synthetic peptides, glycosphingolipids, lectins, lipids, phospholipids, carbohydrates, saccharides, gangliosides, nucleic acids, fragments of nucleic acids, pathogen adhesion factors, receptors, receptor subunits, liposomes, membranes, organelles, cells, tissues, complexes containing said molecules or macromolecules, and wherein said ligands are selected from the group consisting of enzyme substrates, enzyme inhibitors, antigens, antigen analogues, haptens, receptor agonists, receptor antagonists and sugars.

3. The process as set forth in claim 1 wherein said light is from a laser.

4. The process as set forth in claim 1 wherein said collecting and processing step includes the use of a Raman spectrometer in said processing.

5. The process as set forth in claim 4 wherein said spectrometer is an imaging spectrometer.

6. The process as set forth in claim 1 wherein the step of analyzing the processed Raman scattering includes the step of comparing the Raman spectrum of said medium containing said bioconcentrator and said bound analyte against the Raman spectrum of a reference standard having a known Raman spectrum corresponding to that of the same bioconcentrator and bound analyte.

7. The process as set forth in claim 1 wherein the analyte is in solution.

8. The process as set forth in claim 1 wherein the analyte is airborne.

9. The process as set forth in claim 1 wherein said at least one analyte comprises multiple analytes.

10. The process as set forth in claim 9 wherein said multiple analytes are bound on one bioconcentrator.

11. The process as set forth in claim 10 herein said multiple analytes are bound at different locations on said bioconcentrator.

12. The process as set forth in claim 1 wherein said steps are conducted at the same physical location.

13. The process as set forth in claim 1 wherein said step of bringing into contact with said bioconcentrator is conducted at one location and said steps of irradiating, collecting and analyzing are conducted at a different location from said step of bringing into contact with said bioconcentrator.

14. The process as set forth in claim 1 wherein said step of irradiating is performed continuously for real time analysis of the at least one analyte.

15. The process as set forth in claim 1 wherein said collecting and processing step is carried out by a Raman spectrometer selected from the group consisting of: dispersing spectrometers, multichannel spectrometers, Fourier transform spectrometers, Hadamard transform spectrometers, stationary transform spectrometers, acousto-optic tunable filter spectrometers, integrated optic acousto-optic tunable filter spectrometers, fiber optic spectrometers, fiber optic array spectrometers, microscope spectrometers, imaging spectrometers, and imaging microscope spectrometers.

16. The process as set forth in claim 1 wherein said Raman scattering is selected from the group consisting of: normal Raman scattering, surface enhanced Raman scattering, resonance Raman scattering, surface enhanced resonance Raman scattering and Raman evanescent wave scattering.

17. The process as set forth in claim 2 wherein said support member includes a roughened metal surface.

18. The process as set forth in claim 1 wherein said bioconcentrator is maintained stationary.

19. The process as set forth in claim 1 wherein said bioconcentrator is moved.

20. The process as set forth in claim 1 wherein a portion of the bioconcentrator is protected against contact with the analyte, and the analysis step includes the step of comparing one or more of the wavebands associated with the protected portion of the bioconcentrator with the Raman spectral signal of one or more wavebands emanating from the unprotected portion of the bioconcentrator and the bound at least one analyte.

21. The process as set forth in claim 2 wherein a chemical having a known Raman spectrum is located on said support member, and wherein said step of analyzing the processed Raman scattering includes the step of comparing the Raman spectrum of the bioconcentrator and the at least one analyte bound thereto against the Raman spectrum of said chemical.

22. The process as set forth in claim 1 wherein said analyzing is accomplished by comparing at least one waveband in the Raman spectrum of said medium containing said bioconcentrator and the at least one analyte bound thereto, said waveband being known to remain unchanged when the binding of the at least one analyte to the bioconcentrator is effected from the same waveband in the Raman spectrum of the unbound bioconcentrator, to at least one other waveband in said Raman spectrum of said medium containing said bioconcentrator and the at least one analyte bound thereto, said at least one waveband being known to change when the binding of the at least one analyte to the bioconcentrator is effected from the same at least one other waveband in the spectrum of the unbound bioconcentrator.

23. The process as set forth in claim 1 wherein there are several bioconcentrators located on one support member, and an analyte is bound to each bioconcentrator and wherein the Raman spectrum from each bioconcentrator is analyzed.

24. The process as set forth in claim 1 wherein said analyzing comprises:

determining the spectrum of the bioconcentrator, setting the values of the bioconcentrator to zero and comparing the value of the Raman scattering spectrum from the analyte bound to the bioconcentrator to said zero value.

* * * * *